US008093361B2

(12) United States Patent
Ochiai et al.

(10) Patent No.: US 8,093,361 B2
(45) Date of Patent: Jan. 10, 2012

(54) ANTI-PERP ANTIBODY

(75) Inventors: Atsushi Ochiai, Chiba (JP); Norihiko Shiraishi, Tokyo (JP); Yoko Kato, Tokyo (JP); Toshio Ota, Tokyo (JP); Susume Sekine, Tokyo (JP); Kenya Shitara, Tokyo (JP); Akiko Furuya, Tokyo (JP); So Ohta, Tokyo (JP); Emi Hosaka, Stuttgart (DE); Yuka Sasaki, Tokyo (JP)

(73) Assignees: Kyowa Hakko Kirin Co., Ltd, Tokyo (JP); Japan as represented by President of National Cancer Center, Tokyo (JP)

( * ) Notice: Subject to any disclaimer, the term of this patent is extended or adjusted under 35 U.S.C. 154(b) by 740 days.

(21) Appl. No.: 11/628,745

(22) PCT Filed: Jun. 7, 2005

(86) PCT No.: PCT/JP2005/010405
§ 371 (c)(1),
(2), (4) Date: Sep. 12, 2007

(87) PCT Pub. No.: WO2005/121338
PCT Pub. Date: Dec. 22, 2005

(65) Prior Publication Data
US 2009/0258007 A1 Oct. 15, 2009

(30) Foreign Application Priority Data
Jun. 7, 2004 (JP) ................. 2004-168116

(51) Int. Cl.
C07K 16/00 (2006.01)
C12P 21/08 (2006.01)
A61K 39/395 (2006.01)
A61K 39/00 (2006.01)
C12P 21/04 (2006.01)
G01N 33/53 (2006.01)
G01N 33/574 (2006.01)

(52) U.S. Cl. ............. 530/387.9; 530/387.1; 530/387.3; 530/387.7; 530/388.1; 424/130.1; 424/133.1; 424/138.1; 424/139.1; 435/69.6; 435/7.1; 435/7.23

(58) Field of Classification Search .......... None
See application file for complete search history.

(56) References Cited

U.S. PATENT DOCUMENTS
5,714,350 A 2/1998 Co et al.
2006/0286090 A1 12/2006 Attardi et al.
2009/0169547 A1 7/2009 Sahin et al.

FOREIGN PATENT DOCUMENTS
WO 01/10883 A1 2/2001
WO WO 01/90353 A1 11/2001
WO WO 02/060317 A2 8/2002
WO WO 03/057160 A2 7/2003
WO 2005/121338 A1 12/2005

OTHER PUBLICATIONS

Paul, Fundamental Immunology, 3rd Edition, 1993. pp. 292-295.*
Attardi, Reczek, and Cosmas. PERP, an apoptosis-associated target of p53, is a novel member of the PMP-22/gas3 family. Genes and Development, 2000. vol. 14, pp. 704-718.*
Campbell. Monoclonal Anitbody Technology, 1984. pp. 1-12.*
Homepage of Pro Sci Incorporated, on line, retrieved on Mar. 31, 2004, internet <http://www.prosci-inc.com/Antibody-TDS/2451%20PERP.html.
Casset et al., "A peptide mimetic of an anti-CD4 monoclonal antibody by rational design", Biochemical and Biophysical Research Communications, 2003, 307: 198-205.
Chen et al., "Selection and Analysis of an Optimized Anti-VEGF Antibody: Crystal Structure of an Affinity-matured Fab in Complex with Antigen", J. Mol. Biol., 1999, 293: 865-881.
Co et al., "Genetically Engineered Deglycosylation of the Variable Domain Increases the Affinity of an Anti-CD33 Monoclonal Antibody", Molecular Immunology, 1993, 30(15): 1361-1367.
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody", The Journal of Immunology, 2002, 169: 3076-3084.
Holm et al., "Functional mapping and single chain construction of the anti-cytokeratin 8 monoclonal antibody TS1", Molecular Immunology, 2007, 44: 1075-1084.
Lewin, Genes IV, 1990, Oxford University Press, p. 810.
MacCallum et al., "Antibody-antigen Interactions: Contact Analysis and Binding Site Topography", J. Mol. Biol., 1996, 262: 732-745.
Novus Biologicals Catalog, 2005, p. 160.
PCT/JP2006/324385 International Search Report issued on Feb. 6, 2007.
Rabbit Polyclonal anti-PERP, Catalog No. NB500-231, Antibody Spec Sheet, Novus Biologicals, 2 pages, 2005.
Rudikoff et al., "Single amino acid substitution altering antigen-binding specificity", Proc. Natl. Acad. Sci. USA, 1982, 79: 1979-1983.
Vajdos et al., "Comprehensive Functional Maps of the Antigen-binding Site of an Anti-ErbB2 Antibody Obtained with Shotgun Scanning Mutagenesis", J. Mol. Biol., 2002, 320: 415-428.

(Continued)

Primary Examiner — Anne M. Gussow
(74) Attorney, Agent, or Firm — Sughrue Mion, PLLC

(57) ABSTRACT

The present invention provides an antibody which specifically recognizes three-dimensional structure of an extracellular region of a polypeptide encoded by PERP (p53 apoptosis effector related to PMP-22) gene and binds to the extracellular region. The antibody of the present invention is useful for treatment of various diseases which highly expresses a polypeptide encoded by the PERP gene. Also, a polypeptide encoded by the PERP gene or a cell expressing the polypeptide can be specifically detected by an immunological method using the antibody, so that the antibody is useful for diagnosis of various diseases related to PERP.

33 Claims, 18 Drawing Sheets

OTHER PUBLICATIONS

Wright et al., "Genetically Engineered Antibodies: Progress and Prospects", Critical Reviews in Immunology, 1992, 12(3,4): 125-168.

Wu et al., "Humanization of a Murine Monoclonal Antibody by Simultaneous Optimization of Framework and CDR Residues", J. Mol. Biol., 1999, 294: 151-162.

Restriction Requirement mailed Dec. 3, 2008, in U.S. Appl. No. 11/634,209.

Response to Restriction Requirement filed Dec. 31, 2008, in U.S. Appl. No. 11/634,209.

Non-Final Office Action mailed Mar. 18, 2009, in U.S. Appl. No. 11/634,209.

1.111 Amendment filed Jul. 20, 2009, in U.S. Appl. No. 11/634,209.

Final Office Action mailed Oct. 21, 2009, in U.S. Appl. No. 11/634,209.

"PERP Antibody Catalog No. NB500-231", Novus Biological Inc., Jun. 5, 2004.

"Internet Archive Wayback Machine", Novus Biological Inc., Jun. 5, 2004.

McKenzie, S.J. et al., "Generation and characterization of monoclonal antibodies specific for the human neu oncogene product, p185", Oncogene, (1989), p. 543-548, vol. 4.

Tempest, P.R. et al., "Reshaping a human monoclonal antibody to inhibit human respiratory syncytial Virus infection in vivo", Bio/Technology, (1991), p. 266-271, vol. 9.

Carter et al., "Humanization of an anti-P185her2 antibody for human cancer therapy", Proc. Natl. Acad. Sci., 1992, 89: 4285-4289.

EP 06834140.3 European Search Report issued on Mar. 30, 2010 in the name of Kyowa Hakko Kirin Co., Ltd.

Marques et al., "Mice Lacking the p53/p63 Target Gene Perp Are Resistant to Papilloma Development", Cancer Research, 2005, 65 (15): 6551-6556.

Atsushi Ochiai et al., 1.116 Amendment filed Jan. 21, 2010, in U.S. Appl. No. 11/634,209.

Atsushi Ochiai et al., Advisory Action mailed Feb. 8, 2010, in U.S. Appl. No. 11/634,209.

Atsushi Ochiai et al., Supplemental 1.116 Amendment filed Mar. 22, 2010 in U.S. Appl. No. 11/634,209.

Atsushi Ochiai et al., Non-Final Office Action mailed Apr. 22, 2010 in U.S. Appl. No. 11/634,209.

Atsushi Ochiai et al., 1.111 Amendment filed Jul. 21, 2010, in U.S. Appl. No. 11/634,209.

Presta, "Selection, design, and engineering of therapeutic antibodies", Journal of Allergy Clinical Immunology, 2005, 116: 731-736.

Atsushi Ochiai et al., 1.116 Amendment filed Nov. 18, 2010, in U.S. Appl. No. 11/634,209.

Atsushi Ochiai et al., Notice of Allowance mailed Dec. 29, 2010, in U.S. Appl. No. 11/634,209.

"Alphabetical Product List", website of Novus Biologicals, Nov. 15, 2003 (retrieved on Feb. 3, 2011), retrieved from http://web.archive.org/web/20031115052225/www.novus-biologicals.com/alpha.php/P/140.

AU 2005252521 Australian Examination Report issued on Sep. 22, 2009 (in the name of Japan as represented by President of National Cancer Center and Kyowa Hakko Kogyo Co., Ltd.).

EP 05749067.4 Supplemental European Search Report issued on Jun. 25, 2007.

EP 05749067.4 Office Action issued on Dec. 13, 2007 (in the name of Kyowa Hakko Kogyo Co., Ltd.).

EP 05749067.4 Office Action issued on Dec. 29, 2008.

EP 05749067.4 Office Action issued on Mar. 12, 2010 (in the name of Kyowa Hakko Kirin Co., Ltd.).

EP 06834140.3 European Examination Report issued Sep. 28, 2010 (in the name of Kyowa Hakko Kirin Co., Ltd. et al.).

JP 2006-514511 Office Action issued Feb. 8, 2011 (in the name of Kyowa Hakko Kirin Co., Ltd.—with English-language translation).

"Novus Biologicals-Perp Antibody", website of Novus Biologicals, [retrieved on Jun. 23, 2005], retrieved from the Internet < Url:http://www.novusbiologicals.com/data_sheet.php/4400/S/Perp/0>.

PCT/JP2005/010405 International Search Report issued on Sep. 20, 2005.

Atsushi Ochiai et al., Final Office Action mailed Aug. 23, 2010, in U.S. Appl. No. 11/634,209.

Atsushi Ochiai et al., Request for Continued Examation (RCE) filed Mar. 29, 2011, in U.S. Appl. No. 11/634,209.

* cited by examiner

1: MOLECULAR WEIGHT MARKER
2: PERP-EXPESSING CHO CELL
3: CHO/DG44 CELL
4: Colo 205 CELL LINE
5: PC-1 CELL LINE FIG. 5
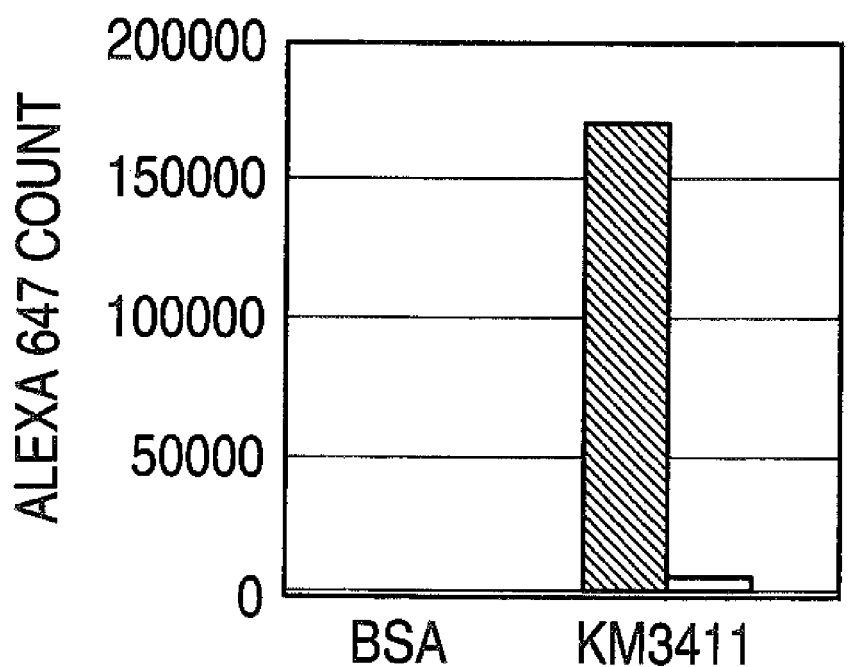
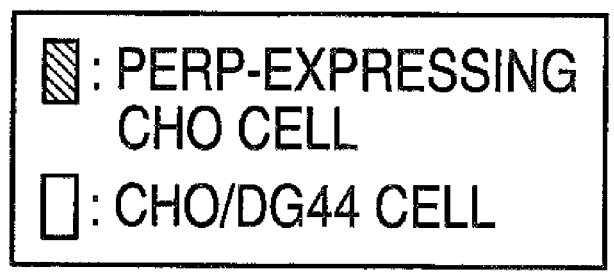

ANTI-PERP ANTIBODY

TECHNICAL FIELD

The present invention relates to an antibody which specifically recognizes three-dimensional structure of an extracellular region of a polypeptide encoded by PERP (p53 apoptosis effector related to PMP-22) gene and binds to the extracellular region or the antibody fragment thereof; a method for immunologically detecting a polypeptide encoded by PERP gene using the antibody or the antibody fragment, and an agent for the detection; a method for immunologically detection or immunoassay of a cell expressing the polypeptide, and an agent for the detection or the immunoassay; an agent for diagnosing or treating a disease related to a polypeptide encoded by PERP gene using the antibody or the antibody fragment; and a hybridoma which produces the antibody. Also, the present invention relates to a gene recombinant antibody which specifically recognizes three-dimensional structure of an extracellular region of a polypeptide encoded by PERP gene and binds to the extracellular region or the antibody fragment thereof; a DNA encoding the antibody; a vector comprising the DNA; a transformant obtainable by transformation of the vector; and a process for producing the antibody which comprises culturing the hybridoma or the transformant.

BACKGROUND ART

Cancer cells produce substances in a large amount which are produced in a small amount or are rarely produced in normal cells. Cancer cells can be detected by detecting or quantitatively determining such substances. The substances which are produced much more in cancer cells than in normal cells include oncogene products, growth factors and the like, and some of them related to malignant transformation, growth, progress, metastasis and fixation of the cells. Cancer can be diagnosed by detecting or quantitatively determining those substances which are characteristic to cancer cells, that is, the so-called tumor markers.

Up to now, tumor markers which have been used include embryonal cancer antigens such as carcinoembryonic antigen (CEA), α-fetoprotein (AFP) and CA 125; enzymes such as nerve-specific enolase (NSE), acidic phosphatase and creatine kinase (CK); and hormone-related substances such as adrenocorticotropic hormone (ACTED, anti-diuretic hormone (ADH) and calcitonin (CT). In colorectal cancer, CEA, CA19-9, NCC-ST-439, STN and the like have been used as markers for determining the therapeutic effect and recurrence. However, when the above-described tumor markers are used, there are many cases where even malignant tumor such as cancer is determined to be negative and, even in healthy persons and patients with benign tumor, there are some cases where they are determined to be pseudo-positive. For example, when the cases where tumor marker is positive were checked for diseased period in colorectal cancer, CEA, CA19-9, NCC-ST-439 and STN were detected only in 36%, 30%, 35% and 21%, respectively, of the patients during a stage where healing excision is possible whereby those tumor markers are not sufficient tumor markers for finding of colorectal cancer in early stages [*Tumor Markers for Colorectal Cancer, CRC*, 1(4), 42 (1992)].

In order to enhance sensitivity and specificity in diagnosis of cancer, it is effective to combine plural tumor markers. When a new tumor marker is found, it is possible to enhance sensitivity and precision of diagnosis of cancer by a sole use of a new tumor marker or by a combined use with the conventional tumor marker.

In pancreatic cancer, general clinical test items show normal value and, in addition, no characteristic clinical observation is available in early stage of the disease and, accordingly, it is difficult to find patients suffering from pancreatic cancer in early stages. In patients suffering from pancreatic cancer where biliary obstruction or liver metastasis happens, there are some cases where alkaline phosphatase value and bilirubin value increase. In cancer of pancreas, pancreatitis is generated in a peripheral side of obstructed pancreatic duct due to tumor and, as a result, enzymes secreted outside the pancreas such as amylase, elastase and RNase and inhibitors for the enzymes come into blood and increase whereby the enzymes and the inhibitors for the enzymes as such are used as tumor markers and, for example, PSTI pancreatic secretory trypsin inhibitor) has been known. PSTI is an inhibitor for trypsin secreted into pancreatic juice and PSTI in blood highly increases in various kinds of malignant tumor patients. It is noted in high frequency particularly in patients suffering from pancreatic cancer [*Rinsho Byori*, 11, 1229 (1986)].

CA19-9 has been widely used as a tumor marker for diagnosis and treatment monitor of pancreatic duct cancer having a high expressing frequency. As other tumor markers for pancreatic duct cancer, CEA, SLX, NCC-ST-439, sialyl Tn, DuPan-2, ferritin and the like have been known. However, in primary pancreatic cancer without metastasis, there are many cases where measured values of those tumor markers do not increase and there are also many cases where the judgment is pseudo-positive from the measured values of those tumor markers whereupon no well-reliable diagnostic method for pancreatic cancer has been known.

In the most precise and the highest cost effective method in diagnosis and staging of pancreatic cancer, CT (computed tomography) is carried out in the initial test. When it is found to be impossible to extirpate tissues or to be metastasized by CT, percutaneous suction with a needle is carried out for tissue diagnosis. If excisable tumor is found or no tumor is found at all by CT, an ultrasonic endoscope is used. Besides that, ultrasonic wave and endoscope retrograde cholangiopanreatography are used for a common test. It is rare to carry out arteriography and pancreatic function test in order to determine whether excision is possible. Furthermore, when diagnosis is difficult, exploratory laparotomy may be carried out.

However, since pancreas is a retroperitoneal organ, it is not easy to precisely find pancreatic cancer in early stages by those diagnostic methods. An early detection contributes in improvement in curing rate and, therefore, there has been a demand for an excellent diagnostic method for pancreatic cancer in an early stage.

The DNA sequence of PERP (also referred to as "THW" or "PIGPC1") is known (WO98/55508, WO99/54461, WO00/55350, WO01/22920, WO01/66719, WO00/61612, WO02/00174, WO02/47534, US2003-0064947, US2003-0065157, WO00/55629, WO02/60317, US2002-0119463).

A polypeptide encoded by the PERP gene is a protein consisting of 193 amino acids and is presumed to be a four-times transmembrane protein from its primary sequence. It has been known that a polypeptide encoded by PERP gene is a protein concerning p53-dependent apoptosis [*Genes & Development* 14, 704 (2000)]. It has been further shown that, in thymus cells and nerve cells prepared from PERP gene knocked out mice, apoptosis induction upon DNA damage is partially inhibited [*Curr. Biol.*, 13, 1985 (2003)]. It has been also reported that PERP is a gene in which expression is lowered in highly metastatic cancer cells [*Anticancer Research,* 20, 2801 (2000)].

As an antibody binding to a polypeptide encoded by the PERP gene (hereinafter referred to as "anti-PERP antibody"), a polyclonal antibody prepared from an intracellular partial peptide in the C terminal or a partial peptide of the first extracellular loop in a PERP gene product as an immunogen has been known (Home page of Pro Sci Incorporated, on line, retrieved on Mar. 31, 2004, internet <www.prosci-inc.com/Antibody-TDS/2451%20PERP.html>, home page of Novus Biologicals, Inc., on line, retrieved on Mar. 31, 2004, internet <www.novus-biologicals.com/print_data_sheet.php/4000>). These polyclonal antibodies have been shown to be applicable to Western blotting or immunohistostaining. Up to now, no antibody which recognizes the three-dimensional structure of an extracellular region of polypeptide encoded by PERP gene and binds to the extracellular region has been known.

It has been known that, when an antibody of non-human animals such as a mouse antibody is administered to human, it is usually recognized as a xenobiotic substance and accordingly that a human antibody against a mouse antibody (human anti-mouse antibody: HAMA) is induced in human body. It has been known that HAMA reacts with the administered mouse antibody to induce side effects [*J. Clin. Oncol.,* 2, 881 (1984), *Blood,* 65, 1349 (1985), *J. Natl. Cancer Inst.,* 80, 932 (1988), *Proc. Natl. Acad. Sci. USA* 82, 1242 (1985)], promotes the disappearance of the mouse antibody from the body [*Blood* 65, 1349 (1985), *J. Nuc. Med.,* 26, 1011 (1985), *J. Natl. Cancer Inst.,* 80, 937 (1988)] and reduces the therapeutic effect of the mouse antibody [*J. Immunol.,* 135, 1530 (1985), *Cancer Res.,* 46, 6489 (1986)].

In order to solve these problems, it has been attempted to prepare a humanized antibody such as a human chimeric antibody or a human CDR-grafted antibody from an antibody of non-human animals by using genetic recombination techniques.

In comparison with an antibody of non-human animals such as a mouse antibody, the humanized antibody has various advantages in clinical application to human. It has been reported, for example, that, in experiments using monkeys, immunogenicity is lowered and its half-life period in blood becomes longer in comparison with a mouse antibody [*Cancer Res.,* 56, 1118 (1996), *Immunol.,* 85, 668 (1995)]. Thus it is expected that, in comparison with the antibody of non-human animals, the humanized antibody has little side effects in human and its therapeutic effect lasts for a long period.

In addition, since the humanized antibody is prepared by using genetic recombination techniques, it can be prepared as molecules in various forms. For example, when the γ1 subclass is used as a heavy chain (hereinafter referred to as "H chain") constant region (hereinafter referred to as "C region") (H chain C region will be referred to as "CH") of a human antibody, it is possible to prepare a humanized antibody having a high effector function such as antibody-dependent cellular cytotoxicity (hereinafter referred to as "ADCC") [*Cancer Res.,* 56, 1118 (1996)] and imposed half-life in blood can be expected in comparison with a mouse antibody [*Immunol.,* 85, 668 (1995)]. Particularly, in the treatment where expressed cell numbers of polypeptide encoded by the PERP gene are lowered high cytotoxic activity such as complement-dependent cytotoxic activity (hereinafter referred to as "CDC activity") and ADCC activity via Fc region of an antibody (region which is other than a hinge region of the antibody heavy chain) is important to the therapeutic effect and, therefore, the humanized antibody is preferred in comparison with the antibody of non-human animals such as a mouse antibody [*J. Immunol.,* 144, 1382 (1990), *Nature,* 322, 323 (1988)].

Moreover, as a result of the progress in protein engineering and genetic engineering in recent years, the humanized antibody can also be prepared as antibody fragment having a low molecular weight such as Fab, Fab', F(ab')$_2$, a single chain antibody (hereinafter referred to as "scFv") [*Science,* 242, 423 (1988)], a dimerized V region fragment (hereinafter be referred to as "diabody") [*Nature Biotechnol,* 15, 629 (1997)], a disulfide stabilized V region fragment (hereinafter referred to as "dsFv") [*Molecular Immunol,* 32, 249 (1995)], a peptide comprising CDR [*J. Biol. Chem.,* 271, 2966 (1996)] and the like, and these antibody fragments are better in transition to target tissues than whole antibody molecules [*Cancer Res.,* 52, 3402 (1992)].

The above-described facts show that, as an antibody to be used for clinical application to human, a humanized antibody or the antibody fragment thereof is preferred than an antibody of non-human animals such as a mouse antibody.

DISCLOSURE OF THE INVENTION

Objects of the present invention are to provide an antibody which specifically recognizes three-dimensional structure of an extracellular region of a polypeptide encoded by PERT gene and binds to the extracellular region or the antibody fragment thereof, a method for immunological detection and immunoassay of a polypeptide encoded by PERT gene using the antibody or the antibody fragment, and an agent for the detection; a method for immunological detection or immunoassay of a cell expressing the polypeptide, and an agent for the detection or the immunoassay; an agent for diagnosing or treating diseases related to a polypeptide encoded by PERP gene using the antibody or the antibody fragment; and a hybridoma which produces the antibody. Also, objects of the present invention are to provide a gene recombinant antibody which specifically recognizes three-dimensional structure of an extracellular region of a polypeptide encoded by PERP gene and binds to the extracellular region or the antibody fragment; a DNA encoding the antibody; a vector comprising the DNA; a transformant obtainable by transformation of the vector; and a process for producing the antibody which comprises culturing the hybridoma or the transformant.

The antibody of the present invention is useful for treatment of various diseases related to a polypeptide encoded by PERP gene. Also, a polypeptide encoded by PERP gene or a cell expressing the polypeptide can be specifically detected or determined by an immunological method using the antibody, so that the antibody is useful for diagnosis of various diseases related to a polypeptide encoded by PERP gene.

MEANS FOR SOLVING THE PROBLEM

The present invention relates to the following (1) to (47):
(1) An antibody which specifically recognizes three-dimensional structure of an extracellular region of a polypeptide encoded by PERP gene and binds to the extracellular region, or the antibody fragment thereof.
(2) The antibody or the antibody fragment according to (1), wherein the extracellular region of the polypeptide is a region of the amino acid sequence at positions 35 to 75 and positions 130 to 154 in the amino acid sequence represented SEQ D by NO:2.
(3) The antibody or the antibody fragment according to (1) or (2), wherein the antibody is a monoclonal antibody.

(4) The antibody or the antibody fragment according to (3), wherein the monoclonal antibody is a monoclonal antibody produced by a hybridoma KM3411 (FERM BP-8643).

(5) The antibody or the antibody fragment according to (3), wherein the monoclonal antibody is a monoclonal antibody which binds to an epitope bound by a monoclonal antibody produced by a hybridoma KM3411 (FERM BP-8643).

(6) A hybridoma which produces the monoclonal antibody described in any one of (3) to (5).

(7) The hybridoma according to (6), wherein the hybridoma is a hybridoma KM3411 (FERM BP-8643).

(8) The antibody or the antibody fragment according to (3), wherein the monoclonal antibody is a gene recombinant antibody.

(9) The antibody or the antibody fragment according to (8), wherein the gene recombinant antibody is a gene recombinant antibody selected from a humanized antibody and a human antibody.

(10) The gene recombinant antibody or the antibody fragment according to (9), wherein the humanized antibody is selected from a human chimeric antibody and a human complimentarity determining region (hereinafter referred to as "CDR")-grafted antibody.

(11) The human chimeric antibody or the antibody fragment according to (10), which comprises a heavy chain (hereinafter referred to as "H chain") variable region (hereinafter referred to as "V region") and a light chain (hereinafter referred to as "L chain") V region of the monoclonal antibody described in any one of (3) to (5).

(12) The human chimeric antibody or the antibody fragment according to (11), which comprises an H chain V region (hereinafter referred to as "VH") and an L chain V region (hereinafter referred to as "VL") of the monoclonal antibody described in any one of (3) to (5) and an H chain constant region (hereinafter referred to as "C region") and an L chain C region of a human antibody.

(13) The human chimeric antibody or the antibody fragment according to (11) or (12), wherein the VH of the antibody comprises the amino acid sequence at positions 19 to 130 in the amino acid sequence represented by SEQ ID NO:12.

(14) The human chimeric antibody or the antibody fragment according to (11) or (12), wherein the VL of the antibody comprises the amino acid sequence at positions 23 to 128 in the amino acid sequence represented by SEQ ID NO:14.

(15) The human chimeric antibody or the antibody fragment according to any one of (11) to (14), wherein the VH of the antibody comprises the amino acid sequence at positions 19 to 130 in the amino acid sequence represented by SEQ ID NO: 12, and the VL of the antibody comprises the amino acid sequence at positions 23 to 128 in the amino acid sequence represented by SEQ ID NO: 14.

(16) The human CDR-grafted antibody or the antibody fragment according to (10), which comprises CDRs of VH and VL of the monoclonal antibody described in according to any one of (3) to (5).

(17) The human CDR-grafted antibody or the antibody fragment according to (16), which comprises CDRs of VH and VL of the monoclonal antibody described in any one of (3) to (5), and frameworks (hereinafter referred to as "FRs") of VH and VL of a human antibody.

(18) The human CDR-grafted antibody or the antibody fragment according to (16) or (17), which comprises CDRs of VH and VL of the monoclonal antibody described in any one of (3) to (5), and FRs of VH and VL of a human antibody, and comprises an H chain C region and an L chain C region of a human antibody.

(19) The human CDR-grafted antibody or the antibody fragment according to any one of (16) to (18), wherein CDR1, CD1, CDR2 and CDR3 of VH of the antibody comprises the amino acid sequences represented by SEQ ID NOs:15, 16 and 17, respectively.

(20) The human CDR-grafted antibody or the antibody fragment according to any one of (16) to (18), wherein CDR1, CDR2 and CDR3 of VL of the antibody comprises the amino acid sequences represented by SEQ ID NOs:18, 19 and 20, respectively.

(21) The human CDR-grafted antibody or the antibody fragment according to any one of (16) to (20), wherein CDR1, CDR2 and CDR3 of VH of the antibody comprises the amino acid sequences represented by SEQ ID NOs:15, 16 and 17, respectively, and CDR1, CDR2 and CDR3 of VL of the antibody comprises the amino acid sequences represented by SEQ ID NOs:18, 19 and 20, respectively.

(22) The human CDR-grafted antibody or the antibody fragment according to any one of (16) to (21), wherein VH of the antibody comprises the amino acid sequence represented by SEQ ID NO:25 or an amino acid sequence in which at least one amino acid residue selected from Gly at position 27, Ser at position 30, Pro at position 41, Lys at position 44, Gly at position 45, Val at position 72 and Ala at position 97 in the amino acid sequence represented by SEQ ID NO:25 is substituted with other amino acid residue.

(23) The human CDR-grafted antibody or the antibody fragment according to any one of (16) to (21), wherein VL of the antibody comprises the amino acid sequence represented by SEQ ID NO:26 or an amino acid sequence in which at least one amino acid residue selected from Gln at position 3, Thr at position 5, Tyr at position 35, Ala at position 42, Leu at position 46, Phe at position 70 and Leu at position 77 in the amino acid sequence represented by SEQ ID NO:26 is substituted with other amino acid residue.

(24) The human CDR-grafted antibody or the antibody fragment according to any one of (16) to (23),
 wherein VH of the antibody comprises the amino acid sequence represented by SEQ ID NO:25 or an amino acid sequence in which at least one amino acid residue selected from Gln at position 3, Thr at position 5, Tyr at position 35, Ala at position 42, Leu at position 46, Phe at position 70 and Leu at position 77 in the amino acid sequence represented by SEQ ID NO:25 is substituted with other amino acid residue, and
 wherein VL of the antibody comprises the amino acid sequence represented by SEQ ID NO:26 or an amino acid sequence in which at least one amino acid residue selected from Gln at position 3, Thr at position 5, Tyr at position 35, Ala at position 42, Leu at position 46, Phe at position 70 and Leu at position 77 in the amino acid sequence represented by SEQ ID NO:26 is substituted with other amino acid residue.

(25) The antibody fragment according to any one of (1) to (24), wherein the antibody fragment is an antibody fragment selected from Fab, Fab', F(ab')$_2$, a single chain antibody (scFv), a dimerized V region (diabody), a disulfide stabilized V region (dsFv) and a peptide comprising CDR.

(26) A DNA encoding the antibody or the antibody fragment described in any one of (1) to (5) and (8) to (25).

(27) A recombinant vector comprising the DNA described in (26).

(28) A transformant obtainable by introducing the recombinant vector described in (27) into a host cell.

(29) A process for producing the antibody or the antibody fragment according to any one of (1) to (5) and (8) to (25), which comprises culturing the hybridoma described in (6) or (7) or the transformant described in (28) in a medium to form and accumulate the antibody or the antibody fragment described in any one of (1) to (5) and (8) to (25) in the culture, and recovering the antibody or the antibody fragment from the culture.

(30) A method for immunological detection or immunoassay of a polypeptide encoded by PERP gene, which comprises using the antibody or the antibody fragment described in any one of (1) to (5) and (8) to (25).

(31) The method according to (30), wherein the method for immunological detection or immunoassay is an immunoprecipitation method.

(32) A method for immunological detection or immunoassay of a cell expressing a polypeptide encoded by PERP gene, which comprises using the antibody or the antibody fragment described in any one of (1) to (5) and (8) to (25).

(33) The method according to (32), wherein the method for immunological detection or immunoassay is a fluorescent cell staining method.

(34) An agent for detecting or determining a polypeptide encoded by PERP gene, which comprises using the antibody or the antibody fragment described in any one of (1) to (5) and (8) to (25).

(35) An agent for diagnosing a disease related to a polypeptide encoded by PERP gene, which comprises using the antibody or the antibody fragment described in any one of (1) to (5) and (8) to (25).

(36) The diagnostic agent according to (35), wherein the disease related to a polypeptide encoded by PERP gene is cancer.

(37) A therapeutic agent for treating a disease related to a polypeptide encoded by PERP gene, which comprises the antibody or the antibody fragment described in any one of (1) to (5) and (8) to (25) as an active ingredient.

(38) The therapeutic agent according to (37), wherein the disease related to a polypeptide encoded by PERP gene is cancer.

(39) A method for diagnosing a disease related to a polypeptide encoded by PERP gene, which comprises detecting or determining a cell expressing a polypeptide encoded by PERP gene using the antibody or the antibody fragment described in any one of (1) to (5) and (8) to (25).

(40) A method for diagnosing a disease related to a polypeptide encoded by PERP gene, which comprises detecting or determining a polypeptide encoded by PERP gene using the antibody or the antibody fragment described in any one of (1) to (5) and (8) to (25).

(41) The method according to (39) or (40), wherein the disease relating to a polypeptide encoded by PERP gene is cancer.

(42) A method for treating a disease related to a polypeptide encoded by PERP gene, which comprises administering to a patient the antibody or the antibody fragment described in any one of (1) to (5) and (8) to (25).

(43) The method according to (42), wherein the disease related to a polypeptide encoded by PERP gene is cancer.

(44) Use of the antibody or the antibody fragment described in any one of (1) to (5) and (8) to (25) for the manufacture of an agent for diagnosing a disease related to a polypeptide encoded by PERP gene.

(45) Use of the antibody or the antibody fragment described in any one of (1) to (5) and (8) to (25) for the manufacture of an agent for diagnosing cancer.

(46) Use of the antibody or the antibody fragment described in any one of (1) to (5) and (8) to (25) for the manufacture of an agent for treating a disease related to a polypeptide encoded by PERP gene.

(47) Use of the antibody or the antibody fragment described in any one of (1) to (5) and (8) to (25) for the manufacture of an agent for treating cancer.

The present invention is explained below in detail. This application is based on Japanese patent application No. 2004-168116 filed on Jun. 7, 2004, the specification and drawings of the patent application being incorporated hereinto.

BEST MODE FOR CARRYING OUT THE INVENTION

The present invention relates to an antibody which specifically recognizes three-dimensional structure of an extracellular region of a polypeptide encoded by the PERP gene and binds to the extracellular region, or the antibody fragment thereof.

The PERP gene includes the nucleotide sequence represented by SEQ ID NO:1.

The PERP gene of the present invention also includes a gene comprising a nucleotide sequence in which at least one nucleotide is deleted, substituted or added in the above nucleotide sequence; a gene comprising a nucleotide sequence having at least 60% or more homology, preferably a nucleotide sequence having 80% or more homology, and more preferably a nucleotide sequence having 95% or more homology, of the nucleotide sequence represented by SEQ ID NO:1; a gene comprising a DNA which hybridizes with the DNA comprising the nucleotide sequence represented by SEQ ID NO:1 under stringent conditions; and the like.

A DNA which hybridizes under stringent conditions is a DNA obtained, e.g., by a method such as colony hybridization, plaque hybridization, Southern blot hybridization and DNA microarray method using a DNA having the nucleotide sequence represented by SEQ ID NO:1 as a probe, and specifically includes a DNA which can be identified by carrying out hybridization at 65° C. in the presence of 0.7 to 1.0 mol/L sodium chloride using a filter or a slide glass with colony- or plaque-derived DNA, a PCR product having the sequence or an oligonucleotide DNA immobilized thereon, and then washing the filter or the slide glass at 65° C. using 0.1 to 2-fold concentration SSC solution (composition of the 1-fold concentration SSC solution comprising 150 mmol/L sodium chloride and 15 mmol/L sodium citrate), The hybridization can be carried out in accordance with the methods described, e.g., *Molecular Cloning, A Laboratory Manual*, Second Edition, Cold Spring Harbor Laboratory Press (1989), *Current Protocols in Molecular Biology*, John Wiley & Sons (1987-1997), *DNA Cloning, 1: Core Techniques, A Practical Approach*, Second Edition (Oxford University (1995); and the like. The DNA capable of hybridizing includes a DNA having at least 60% or more, preferably 80% or more, and more preferably 95% or more, homology with the nucleotide sequence represented by SEQ ID NO:1.

In the nucleotide sequence of the gene encoding a protein of a eukaryote, genetic polymorphism is often recognized. The PERP gene of the present invention also includes a gene in which small modification is generated in the nucleotide sequence by such polymorphism as the gene used in the present invention.

The polypeptide encoded by the PERP gene includes a polypeptide comprising the amino acid sequence represented by SEQ ID NO:2; a polypeptide comprising an amino acid sequence in which at least one amino acid is deleted, substituted or added in the amino acid sequence represented by SEQ ID NO:2; a polypeptide comprising an amino acid sequence having at least 60% homology, preferably a polypeptide comprising the amino acid sequence having at least 80% homology more preferably a polypeptide comprising the amino acid sequence having at least 90% homology, and most preferably a polypeptide comprising the amino acid sequence having at least 95% homology, with the amino acid sequence represented by SEQ ID NO:2; and the like.

The polypeptide which comprises an amino acid sequence in which one or more amino acid(s) is/are deleted, substituted or added in the amino acid sequence represented by SEQ ID NO:2 can be obtained, e.g., by introducing a site-directed mutation into a DNA encoding a polypeptide comprising the amino acid sequence represented by SEQ ID NO:2, using the site-directed mutagenesis described, e.g., in *Molecular Cloning, A Laboratory Manual* Second Edition, Cold Spring Harbor Laboratory Press (1989); *Current Protocols in Molecular Biology*, John Wiley & Sons (1987-1997); *Nucleic Acids Research*, 10, 6487 (1982); *Proc. Natl. Acad. Sci. USA*, 79, 6409 (1982); *Gene*, 34, 315 (1985); *Nucleic Acids Research* 13, 4431 (1985); *Proc. Natl. Acad. Sci. USA* 82, 488 (1985); and the like. The number of amino acids to be deleted, substituted or added is not particularly limited, and the number of amino acids is preferably 1 to several tens, e.g., 1 to 20, and more preferably 1 to several e.g., 1 to 5.

The number of the homology described in the present invention may be a known number calculated by using a known homology search program, unless otherwise indicated. Regarding the nucleotide sequence, the number may be calculated by using a default parameter in BLAST [*J. Mol. Biol.*, 215, 403 (1990)] or the like, and regarding the amino acid sequence, the number may be calculated by using a default parameter in BLAST2 [*Nucleic Acids Res.*, 25, 3389 (1997); Genome Res., 7, 649 (1997); www.ncbi.nlm.nih.gov/Education/BLASTinfo/information3.html] or the like.

As the default parameter, G (cost to open gap) is 5 for the nucleotide sequence and 11 for the amino acid sequence; —E (cost to extend gap) is 2 for the nucleotide sequence and 1 for the amino acid sequence; —q (penalty for nucleotide mismatch) is −3; —r (reward for nucleotide match) is 1; —e (expect value) is 10; —W (wordsize) is 11 residues for the nucleotide sequence and 3 residues for the amino acid sequence; —y (dropoff (X) for blast extensions in bits) is 20 for blastn and 7 for a program other than blastn; —X (X dropoff value for gapped alignment in bits) is 15; and —Z (final X dropoff value for gapped alignment in bits) is 50 for blastn and 25 for a program other than blastn (www.ncbi.nlm.nih.gov/blast/html/blastcgihelp.html).

The polypeptide comprising a partial sequence of the amino acid sequence represented by SEQ ID NO:2 can be prepared according to a method known by the skilled person. For example, it can be prepared by deleting a part of DNA encoding the amino acid sequence represented by SEQ ID NO: 2 and culturing a transformant into which an expression vector containing the DNA is introduced. Also, based on the thus prepared polypeptide or DNA, a polypeptide comprising an amino acid sequence in which one or more amino acids are deleted, substituted or added in a partial sequence of the amino acid sequence represented by SEQ ID NO:2 can be prepared in the same manner as described above.

The extracellular region of a polypeptide encoded by the PERP gene is, for example, a region predicted by a known transmembrane region prediction program SOSUI (sosui.proteome.bio.tuat.ac.jp/sosuiframe0.html), prediction program TMHMM ver.2 (www.cbs.dtu.dk/services/TMHMM-2.0/), or the like, based on the amino acid sequence of the polypeptide represented by SEQ ID NO:2.

Specifically, when SOSUI is used, the extracellular region is predicted as a region corresponding to positions 35 to 75 and 130 to 154 in the amino acid sequence represented by SEQ ID NO:2. When TMHMM ver.2 is used, it is predicted as a region corresponding to positions 36 to 76 and 129 to 147 in the amino acid sequence represented by SEQ ID NO:2. At this time, as the parameters used for the prediction, default values in these prediction programs are used.

Also, the extracellular region of a polypeptide encoded by the PERP gene in the present invention may be a region corresponding to positions 33 to 75 and 129 to 150 in the extracellular domain predicted by literature [*Genes & Development* 14, 704 (2000)].

The antibody which specifically recognizes three-dimensional structure of an extracellular region of a polypeptide encoded by the PERP gene and binds to the extracellular region, or the antibody fragment thereof in the present invention can recognizes three-dimensional structure of a natural polypeptide encoded by the PERP gene and binds to the extracellular region of the polypeptide.

The three-dimensional structure of a natural polypeptide encoded by the PERP gene may be any three-dimensional structure, so long as it is equivalent to the structure of a naturally existing polypeptide encoded by the PERP gene comprising the nucleotide sequence represented by SEQ ID NO:1.

The polypeptide having such a three-dimensional structure which is encoded by the PERP gene can bind to the monoclonal antibody produced by a hybridoma KM3411 (FERM BP-8643) of the present invention. Accordingly, the monoclonal antibody of the present invention includes a monoclonal antibody which binds to an epitope which is the same as an epitope bound by the monoclonal antibody produced by a hybridoma KM3411 (GERM BP-8643).

The method for confirming the binding of the monoclonal antibody produced by a hybridoma KM3411 (FERM BP-8463) includes, for example, known immunological detection methods for cells in which a polypeptide encoded by the PERP gene is expressed, and a method for confirming the binding of a cell in which a specific antigen is expressed and an antibody against the specific antigen such as a fluorescent cell staining method is suitably used. Examples include an immunofluorescent staining method described in (3) of Example 4 or (2) of Example 5, immunoprecipitation described in (1) of Example 5 and the like. Also, it can be confirmed by combining known immunological detection methods [*Monoclonal Antibodies—Principles and practice*, Third edition, Academic Press (1996), *Antibodies—A Laboratory Manual*, Cold Spring Harbor Laboratory (1988), *Monoclonal Antibody Experiment Manual*, Kodansha Scientific (1987)] and the like.

The cell in which the polypeptide encoded by the PERP gene is expressed includes a cell naturally existing in human body, a cell line established from a cell naturally existing in human body, a cell obtained by gene recombinant technique, and the like.

The cell naturally existing in human body include a cell which expresses the polypeptide in the living body of a cancer patient, such as a cell expressing the polypeptide among tumor cells obtained by biopsy or the like.

The cell line established from a cell naturally existing in human body includes a cell line expressing the polypeptide among cell lines obtained by establishing the above cell expressing the polypeptide obtained by the cancer patient. Examples include cell lines established from human such as pancreatic cancer cell line Capan-2 (ATCC HTB-80) or BxPC-3 (ATCC CRL-1687), colorectal cancer cell line Colo205 (ATCC CCL-222), HT29 (ATCC HTB-38) or WiDr (ATCC CCL-218), lung cancer cell line NCI-H128 (ATCC HTB-120) or NCI-H69 (ATCC HTB-119), breast cancer cell line MCF7 (ATCC HTB-22) and uterus cancer cell line MCAS (JCRB 0240).

The cell obtained by gene recombinant technique includes, for example, a cell expressing the polypeptide obtained by introducing an expression vector containing cDNA encoding the polypeptide into an insect cell or an animal cell, and the like, such as a cell expressing the polypeptide into which PERP gene expression plasmid pcPERPmH is introduced as described in (1) of Example 4.

The antibody which specifically recognizes three-dimensional structure of an extracellular region of a polypeptide encoded by the PERP gene and binds to the extracellular region in the present invention includes a polyclonal antibody and a monoclonal antibody, and preferably a monoclonal antibody is used.

The monoclonal antibody includes an antibody produced by a hybridoma and a gene recombinant antibody produced by a transformant transformed with an expression vector containing a gene encoding an antibody.

The hybridoma can be prepared, for example, by preparing the above cell expressing a polypeptide encoded by the above PERP gene as an antigen, inducing an antibody-producing cell having antigen specificity from an animal with which the antigen is immunized, and fusing it with a myeloma cell. The anti-PERP antibody can be obtained by culturing the hybridoma or administering the hybridoma cell into an animal to cause ascites tumor in the animal and separating and purifying the culture or the ascites.

The animal immunized with an antigen may be any animal, so long as a hybridoma can be prepared, and mouse, rat, hamster, rabbit or the like is suitably used. Also, the cell having antibody-producing activity can be obtained from such an animal, and the antibody of the present invention includes an antibody produced by a hybridoma obtained by fusion of the cell after in vitro immunization with a myeloma cell.

Examples of the monoclonal antibody of the present invention include a mouse antibody KM3411 produced by a hybridoma KM3411. The hybridoma KM3411 has been deposited to International Patent Organism Depositary, National Institute of Advanced Industrial Science and Technology (Central 6, 1-1, Higashi 1-chome, Tsukuba-shi, Ibaraki, Japan) as FERM BP-8643 on Feb. 24, 2004.

The gene recombinant antibody includes antibodies prepared by gene recombination, such as a humanized antibody, a human antibody or an antibody fragment. The gene recombinant antibody which has characteristics of a monoclonal antibody such as low antigenicity and prolonged half life in blood is preferred as a therapeutic agent.

The humanized antibody of the present invention includes a human chimeric antibody and a human CDR-grafted antibody.

A human chimeric antibody is an antibody comprising a heavy chain variable region (hereinafter referred to as "VH") and a light chain variable region (hereinafter referred to as "VL") from a non-human animal, and a heavy chain constant region (hereinafter referred to as "CH") and a light chain constant region (hereinafter referred to as "CL") from a human antibody.

The human chimeric antibody of the present invention can be produced by obtaining cDNAs encoding VH and VL from a hybridoma which produces a monoclonal antibody which specifically recognizes three-dimensional structure of an extracellular region of a polypeptide encoded by the PERP gene and binds to the extracellular region, inserting the cDNAs into an expression vector for animal cell having genes encoding CH and CL of a human antibody to construct a human chimeric antibody expression vector, and introducing the vector into an animal cell to express the antibody.

As the CH of the human chimeric antibody, any CH can be used, so long as it belongs to human immunoglobulin (hereinafter referred to as "hIg"), and those belonging to the hIgG class are preferred, and any one of the subclasses belonging to the hIgG class, such as hIgG1, hIgG2, hIgG3 and hIgG4, can be used. As the CL of human chimeric antibody, any CL can be used, so long as it belongs to the hIg class, and those belonging to the κ class or λ class can be used.

The human chimeric antibody of the present invention includes a human chimeric antibody comprising CDR1, CDR2 and CDR3 of VH of the antibody comprising amino acid sequences represented by SEQ ID NOs:15, 16 and 17, respectively, and/or CDR1, CDR2 and CDR3 of V of the antibody comprising amino acid sequences represented by SEQ ID NOs:18, 19 and 20, respectively, and specifically includes a human chimeric antibody wherein VH of the antibody comprises the amino acid sequence at positions 19 to 130 in the amino acid sequence represented by SEQ ID NO:12, and/or VL of the antibody comprises the amino acid sequence at positions 23 to 128 in the amino acid sequence represented by SEQ ID NO:14.

A human CDR-grafted antibody is an antibody in which CDR amino acid sequences of VH and VL of an antibody from a non-human animal are grafted into appropriate positions of VH and VL of a human antibody.

The human CDR-grafted antibody of the present invention can be produced by grafting CDR sequences of VH and VL of an antibody from a non-human animal which is produced by a hybridoma which produces a monoclonal antibody of a non-human animal which specifically recognizes three-dimensional structure of an extracellular region of a polypeptide encoded by the PERP gene and binds to the extracellular region, into FR of VH and VL of an optional human antibody to construct cDNAs encoding V regions, inserting the cDNAs into an expression vector for animal cell having genes encoding CH and CL of a human antibody to construct a human CDR-grafted antibody expression vector, and then introducing the expression vector into an animal cell to express the antibody.

The amino acid sequences of FRs of VH and VL of a human antibody may be any amino acid sequences, so long as they are amino acid sequences of FRs of VH and VL from a human antibody. For example, they includes amino acid sequences of FRs of VH and VL of human antibodies registered in database such as Protein Data Bank, common amino acid sequences of each subgroups of FRs of VH and VL of human antibodies described in *Sequences of Proteins of Immunological Interest*, US Dept. Health and Human Services (1991), and the like.

As the CH of human CDR-grafted antibody, any CH can be used, so long as it belongs to the hg, and those of the hIgG class are preferred and any one of the subclasses belonging to the hIgG class, such as hIgG1, hIgG2, hIgG3 and hIgG4, can be used. As the CL of human CDR-grafted antibody, any CL can be used, so long as it belongs to the hIg class, and those belonging to the K class or A class can be used.

The human CDR-grafted antibody of the present invention includes a human CDR-grafted antibody comprising CDR1, CDR2 and CDR3 of VH of the antibody comprising the amino acid sequences represented by SEQ ID NOs:15, 16 and 17, respectively, and/or CDR1, CDR2 and CDR3 of VL of the antibody comprising the amino acid sequences represented by SEQ ID NOs:18, 19 and 20, respectively, or the antibody fragment thereof, and the like. Specific examples include a human CDR-grafted antibody wherein VH of the antibody comprises the amino acid sequence represented by SEQ ID NO:25 or an amino acid sequence in which at least one amino acid residue selected from Gly at position 27, Ser at position 30, Pro at position 41, Lys at position 44, Gly at position 45, 72 at position Val and Ala at position 97 is substituted in the amino acid sequence represented by SEQ ID NO:25, and/or VL of the antibody comprises the amino acid sequence represented by SEQ ID NO:26 or an amino acid sequence in which at least one amino acid residue selected from Gln at position 3, Thr at position 5, Tyr at position 35, Ala at position 42, Leu at position 46, Phe at position 70 and Leu at position 77 is substituted in the amino acid sequence represented by SEQ ID NO:26.

A human antibody is originally an antibody naturally existing in the human body, but it also includes antibodies obtained from a human antibody phage library, a human antibody-producing transgenic animal, which are prepared based on the recent advance in genetic engineering, cell engineering and developmental engineering techniques.

The antibody naturally existing in the human body can be prepared, for example, by isolating a human peripheral blood lymphocyte, immortalizing by infecting with EB virus or the like and then cloning it to thereby obtain lymphocytes capable of producing the antibody, culturing the lymphocytes thus obtained, and purifying the antibody from the culture.

The human antibody phage library is a library in which antibody fragments such as Fab and scFv are expressed on the phage surface by inserting a gene encoding an antibody gene prepared from a human B cell into a phage gene. A phage expressing an antibody fragment having the desired antigen binding activity on the surface can be recovered from the library, using the binding activity to an antigen-immobilized substrate as the index. The antibody fragment can be converted further into a human antibody molecule comprising two fill length H chains and two full length L chains by genetic engineering techniques.

A human antibody-producing transgenic animal is an animal in which a human antibody gene is integrated into its cells. Specifically, a human antibody-producing transgenic mouse can be prepared by introducing a human antibody gene into ES cell of a mouse, transplanting the ES cell into an early stage embryo of other mouse and then developing it. A human antibody is prepared from the human antibody-producing transgenic animal by obtaining a human antibody-producing hybridoma by a hybridoma preparation method usually carried out in non-human animals, culturing the obtained hybridoma and accumulating the human antibody in the culture supernatant.

The antibody fragment of the present invention includes Fab, F(ab')$_2$, Fab', scFv, diabody, dsFv, a peptide comprising CDR, and the like.

An Fab is an antibody fragment having a molecular weight of about 50,000 and having antigen binding activity, in which about a half of the N-terminal side of H chain and the entire L chain, among fragments obtained by treating IgG with a protease, papain (cleaving an amino acid residue at the 224th position of the H chain), are bound together through a disulfide bond.

The Fab of the present invention can be obtained by treating the monoclonal antibody which specifically recognizes three-dimensional structure of an extracellular region of a polypeptide encoded by the PERP gene and binds to the extracellular region, with a protease, papain. Also, the Fab can be produced by inserting DNA encoding Fab of the antibody into an expression vector for prokaryote or an expression vector for eukaryote, and introducing the vector into a prokaryote or eukaryote to express the Fab.

An F(ab')$_2$ is an antibody fragment having a molecular weight of about 100,000 and having antigen binding activity and comprising two Fab regions which are bound in the hinge position obtained by digesting the lower part of two disulfide bonds in the hinge region of IgG with enzyme, pepsin.

The F(ab')$_2$ of the present invention can be obtained by treating the monoclonal antibody which specifically recognizes three-dimensional structure of an extracellular region of a polypeptide encoded by the PERP gene and binds to the extracellular region, with a protease, pepsin. Also, it can be prepared by binding Fab' described below via a thioether bond or a disulfide bond.

An Fab' is an antibody fragment having a molecular weight of about 50,000 and having antigen binding activity, which is obtained by cleaving a disulfide bond at the hinge region of the F(ab')$_2$.

The Fab' of the present invention can be obtained by treating the F(ab')$_2$ of the present invention which specifically recognizes three-dimensional structure of an extracellular region of a polypeptide encoded by the PERP gene and binds to the extracellular region, with a reducing agent, dithiothreitol. Also, the Fab' can be produced by inserting DNA encoding Fab' fragment of the antibody into an expression vector for prokaryote or an expression vector for eukaryote, and introducing the vector into a prokaryote or eukaryote to express the Fab'.

An scFv is a VH-P-VL or VL-P-VH polypeptide in which one chain VH and one chain VL are linked using an appropriate peptide linker (hereinafter referred to as "P") and is an antibody fragment having antigen binding activity.

The scFv of the present invention can be produced by obtaining cDNAs encoding VH and VL of the monoclonal antibody which specifically recognizes three-dimensional structure of an extracellular region of a polypeptide encoded by the PERP gene and binds to the extracellular region in the present invention, constructing DNA encoding scFv inserting the DNA into an expression vector for prokaryote or an expression vector for eukaryote, and then introducing the expression vector into a prokaryote or eukaryote to express the scFv.

A diabody is an antibody fragment in which scFv's forms a dimer, and has divalent antigen binding activity. In the divalent antigen binding activity, two antigens may be the same or different.

The diabody of the present invention can be produced by obtaining cDNAs encoding VH and VL of the monoclonal antibody which specifically recognizes three-dimensional structure of an extracellular region of a polypeptide encoded by the PERP gene and binds to the extracellular region in the present invention, constructing DNA encoding scFv so that the length of the amino acid sequence of P is 8 or less residues, inserting the DNA into an expression vector for prokaryote or an expression vector for eukaryote, and then introducing the expression vector into a prokaryote or eukaryote to express the diabody.

A dsFv is obtained by binding polypeptides in which one amino acid residue of each of VH and VL is substituted with a cysteine residue via a disulfide bond between the cysteine residues. The amino acid residue to be substituted with a cysteine residue can be selected based on a three-dimensional structure estimation of the antibody in accordance with the method shown by Reiter et al. (*Protein Engineering*, 697 (1994)).

The dsFv of the present invention can be produced by obtaining cDNAs encoding VH and VL of the monoclonal antibody which specifically recognizes three-dimensional structure of an extracellular region of a polypeptide encoded by the PERP gene and binds to the extracellular region in the present invention, constructing DNA encoding dsFv, inserting the DNA into an expression vector for prokaryote or an expression vector for eukaryote, and then introducing the expression vector into a prokaryote or eukaryote to express the dsFv.

A peptide comprising CDR is constituted by including one region or more of CDRs of VH or VL. Plural peptide comprising CDRs can be bound directly or via an appropriate peptide linker.

The peptide comprising CDR of the present invention can be produced by constructing DNA encoding CDRs of VH and VL of the monoclonal antibody which specifically recognizes three-dimensional structure of an extracellular region of a polypeptide encoded by the PERP gene and binds to the extracellular region in the present invention, inserting the DNA into an expression vector for prokaryote or an expression vector for eukaryote, and then by introducing the expression vector into a prokaryote or eukaryote to express the peptide.

The peptide comprising CDR can also be produced by a chemical synthesis method such as an Fmoc method (fluorenylmethoxycarbonyl method) or a tBoc method (t-butyloxycarbonyl method), or the like.

The antibody of the present invention includes antibody derivatives in which a radioisotope, an agent having low molecular weight, an agent having high molecular weight, a protein or the like is chemically or genetically conjugated to the antibody which specifically recognizes three-dimensional structure of an extracellular region of a polypeptide encoded by the PERP gene and binds to the extracellular region or the antibody fragment of the present invention.

The antibody derivatives of the present invention can be produced by chemically conjugating a radioisotope, an agent having low molecular weight, an agent having high molecular weight, a protein or the like to an appropriate substituent group or side chain of the antibody or antibody fragment, to a sugar chain in the antibody or antibody fragment, or the like in the N-terminal side or C-terminal side of an H chain or an L chain of the antibody which specifically recognizes three-dimensional structure of an extracellular region of a polypeptide encoded by the PERP gene and binds to the extracellular region or the antibody fragment thereof (*Antibody Engineering Handbook*, edited by Osamu Kanemitsu, published by Chijin Shokan (1994)).

Also, the antibody derivatives can be produced by linking a DNA encoding the antibody which specifically recognizes three-dimensional structure of an extracellular region of a polypeptide encoded by the PERP gene and binds to the extracellular region or the antibody fragment of the present invention to other DNA encoding a protein to be bound, inserting the DNA into a vector for expression, introducing the expression vector into a host cell, and expressing the antibody derivatives.

Examples of the isotope include $^{131}$I, $^{125}$I and the like, and they can be conjugated to antibodies by, e.g., a chloramine T method.

The agent having a low molecular weight includes anticancer agents such as alkylating agents (e.g., nitrogen mustard, cyclophosphamide, etc.), metabolic antagonists (e.g., 5-fluorouracil, methotrexate, etc.), antibiotics (e.g., daunomycin, bleomycin, mitomycin C, daunorubicin, doxorubicin, etc.), plant alkaloids (e.g., vincristine, vinblastine, vindesine, etc.), hormone agents (e.g., tamoxifen, dexamethasone, etc.), and the like (*Clinical Oncology*, edited by Japanese Society of Clinical Oncology, published by Cancer and Chemotherapy (1996)); anti-inflammatory agents such as steroid agents (e.g., hydrocortisone, prednisone, etc.), non-steroidal agents (e.g., aspirin, indometacin, etc.), immunomodulators (e.g., aurothiomalate, penicillamine, etc.), immunosuppressing agents (e.g., cyclophosphamide, azathioprine, etc.), antihistaminic agents (e.g., chlorpheniramine maleate, clemastine, etc.), and the like (*Inflammation and Anti-inflammatory Therapy*, Ishiyaku Shuppan (1982)); and the like. Examples of the method for conjugating daunomycin to an antibody include a method in which daunomycin and an amino group of an antibody are conjugated via glutaraldehyde, a method in which an amino group of daunomycin and a carboxyl group of an antibody are conjugated via a water-soluble carbodiimide, and the like.

The agent having high molecular weight includes polyethylene glycol (hereinafter referred to as "PEG"), albumin, dextran, polyoxyethylene, styrene-maleic acid copolymer, polyvinylpyrrolidone, pyran copolymer, hydroxypropylmethacrylamide, and the like. By binding these compounds having high molecular weight, the following effects are expected: (1) improvement of stability against various chemical, physical or biological factors, (2) remarkable prolongation of half life in blood, (3) disappearance of immunogenicity, suppression of antibody production, and the like [*Bioconjugate Drug*, Hirokawa Shoten (1993)]. For example, the method for binding PEG to an antibody includes a method in which an antibody is allowed to react with a PEG-modifying reagent [*Bioconjugate Drug*, Hirokawa Shoten (1993)]. The PEG-modifying reagent includes a modifying agent of ε-amino group of lysine (Japanese Published Unexamined Patent Application No. 178926/86), a modifying agent of a carboxyl group of aspartic acid and glutamic acid (Japanese Published Unexamined Patent Application No. 23587/81), a modifying agent of a guanidino group of arginine (Japanese Published Unexamined Patent Application No. 117920/90) and the like.

The protein includes cytokine which activates immunocompetent cells, such as human interleukin 2, human granulocyte macrophage colony-stimulating factor, human macrophage colony-stimulating factor, human interleukin 12, and the like. Also, in order to damage cancer cells directly, a toxin such as ricin, diphtheria toxin and the like, can be used. For example, a fusion antibody with a protein can be produced by linking a cDNA encoding an antibody or antibody fragment to other cDNA encoding the protein, constructing DNA encoding the fusion antibody, inserting the DNA into an expression vector for prokaryote or an expression vector for eukaryote, and then introducing it into a prokaryote or eukaryote to express the fusion antibody.

When the fusion protein is used in a detection method or a quantitative determination method or a detecting agent, a quantitatively determining agent or a diagnosing agent, a label used in usual immunological detection or immunoassay can be used as an agent. The label includes enzymes such as alkaline phosphatase, peroxydase and luciferase, luminescent materials such as acridinium ester and rofin, fluorescent materials such as fluorescein isothiocyanate (FITC) and RITC, and the like.

The production process of the antibody of the present invention is explained below in detail.

1. Preparation of Anti-PERP Monoclonal Antibody Produced by Hybridoma (1) Preparation of Antigen The polypeptide used in the present invention can be produced, for example, by expressing a DNA encoding the polypeptide in a host cell using a method described in

*Molecular Cloning, A Laboratory Manual*, Second Edition, Cold Spring Harbor Laboratory Press (1989), *Current Protocols in Molecular Biology*, John Wiley & Sons (1987-1997) or the like as follows.

Firstly, a recombinant vector is prepared by introducing a full length cDNA containing cDNA encoding the polypeptide into downstream of a promoter of an appropriate expression vector. At this time, if necessary, a DNA fragment having an appropriate length containing a region encoding the polypeptide based on the full length cDNA, and the DNA fragment may be used instead of the above full length cDNA. Next, a transformant producing the polypeptide can be obtained by introducing the recombinant vector into a host cell suitable for the expression vector.

The host cell can be any one so long as it can express the gene of interest, and includes *Escherichia coli*, an animal cell and the like.

The expression vector includes vectors which can replicate autonomously in the host cell to be used or vectors which can be integrated into a chromosome comprising an appropriate promoter at such a position that the DNA encoding the polypeptide can be transcribed.

When a procaryote such as *Escherichia coli* is used as the host cell, it is preferred that the recombinant vector is autonomously replicable in the procaryote and contains a promoter, a ribosome binding sequence, the DNA used in the present invention and a transcription termination sequence. The recombinant vector may further comprise a gene regulating the promoter.

The expression vector includes, for example, pBTrp2, pBTac1, pBTac2 (all manufactured by Roche Diagnostics), pKK233-2 (manufactured by Pharmacia), pSE280 (manufactured by Invitrogen), pGEMEX-1 (manufactured by Promega), pQE-8 (manufactured by QIAGEN), pKYP10 (Japanese Published Unexamined Patent Application No. 110600/83), pKYP200 [*Agricultural Biological Chemistry*, 48, 669 (1984)], pLSA1 [*Agric. Biol. Chem.*, 53, 277 (1989)], pGEL1 [*Proc. Natl. Acad. Sci. USA*, 82, 4306 (1985)], pBluescript II SK(−) (manufactured by Stratagene), pTrs30 [prepared from *Escherichia coli* JM109/pTrS30 (FERM BP-5407)], pTrs32 [prepared from *Escherichia coli* 109/pTrS32 (FERM BP-5408)], pGHA2 [prepared from *Escherichia coli* IGHA2 (FERM BP-400), Japanese Published Unexamined Patent Application No. 221091/85], pGKA2 [prepared from *Escherichia coli* IGKA2 (FERM BP-6798), Japanese Published Unexamined Patent Application No. 221091/85], pTerm2 (U.S. Pat. No. 4,686,191, U.S. Pat. No. 4,939,094, U.S. Pat. No. 5,160,735), pSupex, pUB110, pTP5, pC194, pEG400 [*J. Bacteriol.*, 172, 2392 (1990)], pGEX (manufactured by Pharmacia), pET system (manufactured by Novagen), pME18SFL3 and the like.

Any promoter can be used, so long as it can function in the host cell to be used. Examples include promoters derived from *Escherichia coli*, phage and the like, such as trp promoter (Ptrp), lac promoter, PL promoter, PR promoter and T7 promoter. Also, artificially designed and modified promoters, such as a promoter in which two Ptrp are linked in tandem, tac promoter, lacT7 promoter and letI promoter, can be used.

Also, the above recombinant vector is preferably a plasmid in which the space between Shine-Dalgarno sequence, which is the ribosome binding sequence, and the initiation codon is adjusted to an appropriate distance (for example, 6 to 18 nucleotides). In the nucleotide sequence of DNA encoding the polypeptide used in the present invention, nucleotides can be arranged so as to obtain a suitable codon for expression in the host so that the producing ratio of the polypeptide of interest can be improved. Furthermore, the transcription termination sequence is not essential to express a gene in the above recombinant DNA. However, it is preferred to arrange a transcription terminating sequence immediately downstream of the structural gene.

The procaryotes used for the host cells include procaryotes belonging to the genera *Escherichia*, and examples include *Escherichia coli* XL1-Blue, *Escherichia coli* XL2-Blue, *Escherichia coli* DH1, *Escherichia coil* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49 and the like.

Any introduction method of the recombinant vector can be used, so long as it is a method for introducing DNA into the above-described host cell and examples include a method using a calcium ion described in *Proc. Natl. Acad. Sci. USA*, 69, 2110 (1972), *Gene*, 17, 107 (1982), *Molecular & General Genetics*, 168, 111 (1979) and the like.

When the polypeptide used in the present invention is produced in *Escherichia coli*, the polypeptide can be expressed, depending on the kind of the vector, as a soluble-type in the cytoplasm, as insoluble granules in the cytoplasm or as a soluble-type in periplasmic space.

When an animal cell is used as the host cell, an expression vector includes, for example, pcDNAI, pcDM8 (available from Funakoshi), pAGE107 [Japanese Published Unexamined Patent Application No. 22979/91; *Cytotechnology*, 3, 133 (1990)], pAS3-3 (Japanese Published Unexamined Patent Application No. 227075/90), pCDMS [*Nature*, 329, 840, (1987)], pcDNAI/Amp (manufactured by Invitrogen), pREP4 (manufactured by Invitrogen), pAGE103 [*J. Biochemistry*, 101, 1307 (1987)], pAGE210, pME18SFL3 and the like.

Any promoter can be used, so long as it can function in an animal cell. Examples include a promoter of IE (immediate early) gene of cytomegalovirus (CMV), SV40 early promoter, a promoter of retrovirus, a metallothionein promoter, a heat shock promoter, SRα promoter and the like. Also, the enhancer of the IE gene of human CMV can be used together with the promoter.

The host cell includes human Namalwa cell, monkey COS cell, Chinese hamster ovary (CHO) cell, HST5637 (Japanese Published Unexamined Patent Application No. 299/88) and the like.

Any introduction method of the recombinant vector can be used, so long as it is a method for introducing DNA into an animal cell, and examples include electroporation [*Cytotechnology*, 3, 133 (1990)], the calcium phosphate method (Japanese Published Unexamined Patent Application No. 227075/90), the lipofection method [*Proc. Natl. Acad. Sci. USA* 84, 7413 (1987)], and the like.

As the expression method of the gene, in addition to direct expression, secretory production, fusion protein expression and the like in accordance with the method described in *Molecular Cloning, A Laboratory Manual*, Second Edition, Cold Spring Harbor Laboratory Press (1989) can be carried out. When expression is carried out in a cell derived from eukaryote, a polypeptide to which a sugar or a sugar chain is added can be obtained.

The polypeptide used in the present invention can be produced by culturing the thus obtained transformant in a medium to form and accumulate the polypeptide in the culture, and recovering it from the culture. The method for culturing the transformant in the medium is carried out according to the usual method used in culturing of hosts.

When a microorganism transformed with a recombinant vector containing an inducible promoter as a promoter is cultured, an inducer can be added to the medium, if necessary.

For example, isopropyl-β-D-thiogalactopyranoside or the like can be added to the medium when a microorganism transformed with a recombinant vector using lac promoter is cultured; or indoleacrylic acid or the like can be added thereto when a microorganism transformed with a recombinant vector using trp promoter is cultured.

When a transformant obtained using an animal cell as the host cell is cultured, the medium includes generally used RPMI 1640 medium [*The Journal of the American Medical Association,* 199, 519 (1967)], Eagle's MEM medium [*Science,* 122, 501 (1952)], Dulbecco's modified MEM medium [*Virology,* 8, 396 (1959)] and 199 medium [*Proceeding of the Society for the Biological Medicine,* 73, 1 (1950)], the media to which fetal calf serum, etc. is added, and the like. The culturing is carried out generally at a pH of 6 to 3 and 30 to 40° C. for 1 to 7 days in the presence of 5% $CO_2$. If necessary, an antibiotic such as kanamycin or penicillin can be added to the medium during the culturing.

Thus, the polypeptide used in the present invention can be produced by culturing a transformant derived from a microorganism, an animal cell or the like which comprises a recombinant vector into which a DNA encoding the polypeptide used in the present invention is inserted, in accordance with a general culturing method, to thereby form and accumulate the polypeptide, and then recovering the polypeptide from the culture.

The process for producing the polypeptide includes a method of intracellular expression in a host cell, a method of extracellular secretion from a host cells a method of producing on a host cell membrane outer envelope, and the like. The appropriate method can be selected by changing the host cell used. Also, it can be produced by expressing it as a fusion polypeptide by fusing any protein according to protein engineering technique.

When the polypeptide is produced in a host cell or on a host cell membrane outer envelope, the gene product can be positively secreted extracellularly in accordance with the method of Paulson et al. [*J. Biol. Chem.,* 264, 17619 (1989)], the method of Lowe et al. [*Proc. Natl. Acad. Sci. USA,* 86, 8227 (1989), *Genes Develop.,* 4, 1288 (1990)], the methods described in Japanese Published Unexamined Patent Application No. 336963/93 and WO94/23021, and the like. Also, the production amount can be increased in accordance with the method described in Japanese Published Unexamined Patent Application No. 227075/90 utilizing a gene amplification system using a dihydrofolate reductase gene.

The polypeptide can be isolated and purified from the above culture, for example, as follows.

When the polypeptide is intracellularly expressed in a dissolved state, the cells after culturing are recovered by centrifugation, suspended in an aqueous buffer and then disrupted using ultrasonicator, French press, Manton Gaulin homogenizer, dynomill or the like to obtain a cell-free extract. The cell-free extract is centrifuged to obtain a supernatant, and a purified preparation can be obtained by subjecting the supernatant to a general enzyme isolation and purification techniques such as solvent extraction; salting out with ammonium sulfate etc. desalting; precipitation with an organic solvent; anion exchange chromatography using a resin such as diethylaminoethyl (DEAE)-sepharose, DIAION EPA-75 (manufactured by Mitsubishi Chemical); cation exchange chromatography using a resin such as S-Sepharose FF (manufactured by Pharmacia); hydrophobic chromatography using a resin such as butyl-Sepharose or phenyl-Sepharose; gel filtration using a molecular sieve; affinity chromatography; chromatofocusing; electrophoresis such as isoelectric focusing; and the like which may be used alone or in combination.

When the polypeptide is expressed intracellularly by forming an inclusion body, the cells are recovered, disrupted and centrifuged in the same manner, and the inclusion body of the polypeptide are recovered as a precipitation fraction. The recovered inclusion body of the protein is solubilized with a protein denaturing agent. The protein is made into a normal three-dimensional structure by diluting or dialyzing the solubilized solution, and then a purified product of the polypeptide is obtained by the same isolation purification method as above.

When the polypeptide or the derivative such as a glycosylated polypeptide is secreted extracellularly, the polypeptide or the derivative such as a glycosylated polypeptide can be recovered from the culture supernatant. That is, the culture is treated by a technique such as centrifugation in the same manner as above to obtain a culture supernatant from which solids are removed, a purified product of the polypeptide can be obtained from the culture supernatant by the same isolation purification method as above.

Also, the polypeptide used in the present invention or a partial peptide of the polypeptide can be produced by a chemical synthesis method, such as Fmoc (fluorenylmethyloxycarbonyl) method or tBoc (t-butyloxycarbonyl) method. Also, it can be chemically synthesized using a peptide synthesizer manufactured by Advanced ChemTech, Perkin-Elmer, Pharmacia, Protein Technology Instrument, Synthecell-Vega, PerSeptive, Shimadzu Corporation, or the like.

The polypeptide or the peptide having a partial sequence of the polypeptide obtained by the above method can be used as an antigen.

(2) Immunization of Animal and Preparation of Antibody-Producing Cell

A mouse, rat or hamster 3 to 20 weeks old is immunized with the antigen prepared above, and antibody-producing cells are collected from the spleen, lymph node or peripheral blood of the animal.

The immunization is carried out by administering the antigen to the animal through subcutaneous, intravenous or intraperitoneal injection together with an appropriate adjuvant (for example, complete Freund's adjuvant, combination of aluminum hydroxide gel with pertussis vaccine, or the like), When the antigen is a partial peptide, a conjugate is produced with a carrier protein such as BSA (bovine serum albumin), KLH (keyhole limpet hemocyanin) or the like, which is used as the antigen.

The administration of the antigen is carried our 5 to 10 times every one week or every two weeks after the first administration. On the 3rd to 7th day after each administration, a blood sample is collected from the fundus of the eye, the reactivity of the serum with the antigen is tested, for example, by enzyme immunoassay [*Antibodies—A Laboratory Manual* (Cold Spring Harbor Laboratory (1988)] or the like. A mouse, rat or hamster showing a sufficient antibody titer in their sera against the antigen used for the immunization is used as the supply source of antibody-producing cells.

A polyclonal antibody can be prepared by separating and purifying the serum. Whether the polyclonal antibody specifically recognizes three-dimensional structure of an extracellular region of a polypeptide encoded by the PERP gene and binds to the extracellular region can be examined by the method described in (6) below.

In fusion of the antibody-producing cells and myeloma cells, on the 3rd to 7th days after final administration of the antigen, tissue containing the antibody-producing cells such as the spleen from the immunized mouse, rat or hamster to collect the antibody-producing cell. When the spleen cells are used, the spleen is cut out in an MEM medium (Nissui Pharmaceutical) and loosened by tweezers and centrifuged (at 1200 rpm, for 5 minutes). Then, the supernatant is discarded and a Tris-ammonium chloride buffer (pH. 7.65) is applied for 1 to 2 minutes to remove erythrocytes. After washing 3 times with the MEM medium, antibody-producing cells for fusion is provided.

(3) Preparation of Myeloma Cell

An established cell line obtained from mouse is used as myeloma cells. Examples include 8-azaguanine-resistant mouse (derived from BALB/c mouse) myeloma cell line P3-X63Ag8-U1(P3-U1) [*Current Topics in Microbiology and Immunology*, 18, 1 (1978)], P3-NS1/1-Ag41(NS-1) [*European J Immunology*, 6, 511 (1976)], SP2/0-Ag14(SP-2) [*Nature*, 276, 269 (1978)], P3-X63-Ag8653(653) [*J. Immunology*, 123, 1548 (1979)], P3-X63-Ag8(X63) [Nature 256, 495 (1975)] and the like. These cell lines are subcultured in an 8-azaguanine medium [a medium in which glutamine (1.5 mmol/L), 2-mercaptoethanol ($5\times10^{-5}$ mol/L), gentamicin (10 μg/ml) and fetal calf serum (FCS) are added to RPMI-1640 medium (hereinafter referred to as "normal medium") and 8-azaguanine (15 μg/ml) is further added] and they are subcultured in the normal medium 3 or 4 days before cell fusion to ensure the cell number of $2\times10^7$ or more on the day for fusion.

(4) Cell Fusion

The above-described antibody-producing cells and myeloma cells were sufficiently washed with an MEM medium or PBS (1.83 g of disodium hydrogen phosphate, 0.21 g of potassium dihydrogen phosphate, 7.65 g of sodium chloride, 1 liter of distilled water, pH 7.2) and mixed to give a ratio of the antibody-producing cells:the myeloma cells=5 to 10:1, followed by centrifugation (1200 rpm, 5 minutes), Then, the supernatant is discarded, and precipitated cell group is sufficiently loosen. To $1\times10^8$ of the antibody-producing cells, 0.2 to 1 mL of a mixture solution of 2 g of polyethylene glycol-1000 (PEG-1000), 2 mL of MEM and 0.7 mL of dimethylsulfoxide is added under stirring at 37° C., and 1 to 2 mL of MEM medium is added several times every one or two minutes, and MM medium is added to give a total amount of 50 nm. After centrifugation (900 rpm, 5 minutes), the supernatant is discarded, the cells are gently loosen, and the cells are gently suspended in 100 mL of HAT medium [a medium in which hypoxanthine ($10^{-4}$ mol/L), thymidine ($1.5\times10^{-5}$ mol/L) and aminopterin ($4\times10^{-7}$ mol/L) is added to the normal medium] by suction and sucking out using a measuring pipette. The suspension is dispensed at 100 μl/well onto a 96-well culturing plate and cultured in a 5% $CO_2$ incubator at 37° C. for 7 to 14 days.

After the culturing, a portion of the culture supernatant is sampled and a sample containing a hybridoma which produces an antibody which specifically recognizes three-dimensional structure of an extracellular region of a polypeptide encoded by the PERP gene and binds to the extracellular region is selected according to the method for selecting a hybridoma described below. Then, cloning is carried out twice by a limiting dilution method [Firstly, HT medium (HAT medium from which aminopterin is removed) is used, and secondly, the normal medium is used], and a hybridoma which shows a stably high antibody titer is selected as the monoclonal antibody-producing hybridoma.

(5) Preparation of Monoclonal Antibody

The hybridoma cells producing an anti-PERP monoclonal antibody obtained in (4) are administered by intraperitoneal injection into 8- to 10-weeks-old mice or nude mice treated with pristane (0.5 ml of 2,6,10,14-tetrarmethylpentadecane (pristane) is intraperitoneally administered, followed by feeding for 2 weeks) at a dose of $2\times10^6$ to $5\times10^7$ cells/animal. The hybridoma causes ascites tumor in 10 to 21 days. The ascitic fluid is collected from the mice, centrifuged (at 3,000 rpm, for 5 minutes) to remove solids, subjected to salting out with 40 to 50% saturated ammonium sulfate or to caprylic acid precipitation, and then passed through a DEAE-Sepharose column, a protein A column or a gel filtration column to collect an IgG or IgM fraction as a purified monoclonal antibody.

The subclass of the antibody can be determined using a subclass typing kit by an enzyme immunoassay. The amount of the protein can be determined by the Lowry method or from the absorbance at 280 nm.

(6) Method for Selecting Hybridoma

As the method for selecting a hybridoma producing antibody which specifically recognizes three-dimensional structure of an extracellular region of a polypeptide encoded by the PERP gene and binds to the extracellular region in the present invention, the following method is exemplified.

In order to select an antibody capable of binding to the extracellular region of the polypeptide encoded by the PERP gene maintaining the natural three-dimensional structure, any method can be used, so long as it is a method which can examine binding activity of the polypeptide encoded by the PERP gene to a cell naturally existing in human body, a cell line established from human body or a cell obtained by gene recombinant technique. Examples include an immunofluorescent staining method using FMAT8100HTS system (manufactured by Applied Biosystem) or a fluorescent cell staining method using a flow cytometry. Specific methods include methods described in (3) of Example 4 and (2) of Example 5.

Also, the method for confirming the reactivity include those combining known immunological detection methods [*Monoclonal Antibodies—Principles and practice*, Third edition, Academic Press (1996), *Antibodies—A Laboratory Manual*, Cold Spring Harbor Laboratory (1988), *Monoclonal, Antibody Experiment Manual*, Kodansha Scientific (1987)] and the like.

The cell naturally existing in human body, the cell line established from human body and the cell obtained by gene recombinant technique for obtaining the polypeptide encoded by the PERP gene include the cells described above, and the cell expressing the polypeptide encoded by the PERP gene obtained by gene recombination sequence is preferred because whether or not the polypeptide is expressed is apparent. With regard to the cell obtained by gene recombinant technique, it is easy to prepare a cell which does not express the polypeptide as a negative control.

Examples of the hybridoma producing a monoclonal antibody which specifically recognizes three-dimensional structure of an extracellular region of a polypeptide encoded by the PERP gene in the present invention selected by the above method includes a hybridoma cell line KM3411 (FERM BP-8643) which produces a monoclonal antibody KM3411, and the like.

2. Preparation of Gene Recombinant Antibody

As production examples of gene recombinant antibodies, processes for producing humanized antibody such as a human chimeric antibody and a human CDR-grafted antibody are shown below.

(1) Construction of Vector for Expression of Humanized Antibody

A vector for expression of humanized antibody is an expression vector for animal cell into which DNAs encoding CH and CL of a human antibody have been inserted, and is constructed by cloning each of DNAs encoding CH and CL of a human antibody into an expression vector for animal cell.

The C region of a human antibody may be CH and CL of any human antibody. Examples include CH belonging to γ1 subclass, CL belonging to κ class, and the like. As the DNAs encoding CH and CL of a human antibody, a chromosomal DNA comprising an exon and an intron or cDNA can be used. As the expression vector for animal cell, any expression vector can be used, so long as a gene encoding the C region of a human antibody can be inserted thereinto and expressed therein. Examples include pAGE107 [*Cytotechnol.* 3, 133 (1990)], pAGE103 [*J. Biochem.*, 101, 1307 (1987)], pHSG274 [*Gene,* 27, 223 (1984)], pKCR [*Proc. Natl. Acad. Sci. USA,* 78, 1527 (1981)], pSG1bd2-4 [*Cytotechnol.,* 4, 173 (1990)], pSE1UK1Sed1-3 [*Cytotechnol.,* 13, 79 (1993)] and the like. Examples of a promoter and enhancer used for an expression vector for animal cell include an SV40 early promoter (*J. Biochem.* 101, 1307 (1987)), a Moloney mouse leukemia virus LTR (*Biochem. Biophys. Res. Commun.,* 149, 960 (1987)), an immunoglobulin H chain promoter (*Cell,* 41, 479 (1985)) and enhancer (*Cell,* 33, 717 (1983)), and the like.

The vector for expression of humanized antibody may be either of a type in which a gene encoding an antibody H chain and a gene encoding an antibody L chain exist on separate vectors or of a type in which both genes exist on the same vector (tandem type). In respect of easiness of construction of a vector for expression of humanized antibody easiness of introduction into animal cells, and balance between the expression amounts of antibody H and L chains in animal cells, a tandem type of the vector for expression of humanized antibody is more preferred (*J. Immunol. Methods,* 167, 271 (1994)). Examples of the tandem type of the vector for expression of humanized antibody include pKANTEX93 (WO 97/10354), pEE18 (*Hybridoma,* 17, 559 (1998)), and the like.

The constructed vector for expression of humanized antibody can be used for expression of a human chimeric antibody and a human CDR-grafted antibody in animal cells.

(2) Preparation of cDNA Encoding V Region of Antibody from Non-Human Animal and Analysis of Amino Acid Sequence cDNAs encoding VH and VL of an antibody from an non-human animal such as a mouse antibody are obtained as follows.

mRNA is extracted from hybridoma cells producing a mouse antibody or the like to synthesize cDNA. The synthesized cDNA is cloned into a vector such as a phage or a plasmid, to prepare a cDNA library. Each of a recombinant phage or recombinant plasmid containing cDNA encoding VH or VL is isolated from the library using DNA encoding a part of the C region or V region of a mouse antibody as the probe. The frill length of the nucleotide sequences of VH and VL of the mouse antibody of interest on the recombinant phage or recombinant plasmid are determined, and the full length of the amino acid sequences of VH and VL are deduced from the nucleotide sequences.

The non-human animal may be any animal such as mouse, rat, hamster or rabbit, so long as a hybridoma cell can be produced therefrom.

Examples of the method for preparing total RNA from a hybridoma cell include a guanidine thiocyanate-cesium trifluoroacetate method (*Methods in Enzymol.,* 154, 3 (1987)) and the like. Examples of the method for preparing mRNA from total RNA include an oligo (dT) immobilized cellulose column method (*Molecular Cloning, A Laboratory Manual,* Second Edition Cold Spring Harbor Laboratory Press (1989)) and the like. Also, examples of a kit for preparing mRNA from a hybridoma cell include Fast Track mRNA Isolation Kit (manufactured by Invitrogen), Quick Prep mRNA Purification Kit (manufactured by Pharmacia) and the like.

Examples of the method for synthesizing cDNA and preparing a cDNA library include known methods (*Molecular Cloning, A Laboratory Manual,* Cold Spring Harbor Lab, Press (1989); *Current Protocols in Molecular Biology,* Supplement 1-34); a method using a commercially available kit such as Super Script™ Plasmid System for cDNA Synthesis and Plasmid Cloning (manufactured by GIBCO BRL), ZAP-cDNA Kit (manufactured by Stratagene), etc.; and the like.

The vector into which the synthesized cDNA using mRNA extracted from a hybridoma cell as the template is inserted for preparing a cDNA library may be any vector, so long as the cDNA can be inserted. Examples include ZAP Express (*Strategies,* 5, 58 (1992)), pBluescript II SK(+) (*Nucleic Acids Research,* 17, 9494 (1989)), λzapII (manufactured by Stratagene), λgt10 and λgt11 (*DNA Cloning: A Practical Approach,* I, 49 (1985)), Lambda BlueMid (manufactured by Clontech), λExCell and pT7T3 18U (manufactured by Pharmacia), pcD2 (*Mol. Cell. Biol.,* 3, 280 (1983)), pUC18 (*Gene,* 33, 103 (1985)), and the like.

Any *Escherichia coli* for introducing the cDNA library constructed by a phage or plasmid vector may be used, so long as the cDNA library can be introduced, expressed and maintained. Examples include XL1-Blue MRF' (*Strategies* 5, 81 (1992)), C600 (*Genetics,* 39, 440 (1954)), Y1088 and Y1090 (*Science,* 222: 778 (1983)), NM522 (*J. Mol. Biol.,* 166, 1 (1983)), K802 (*J. Mol. Biol.,* 16, 118 (1966)), JM105 (*Gene,* 3, 275 (1985)), and the like.

A colony hybridization or plaque hybridization method using an isotope- or fluorescence-labeled probe may be used for selecting cDNA clones encoding VH and VL of a non-human animal antibody from the cDNA library (*Molecular Cloning, A Laboratory Manual,* Second Edition, Cold Spring Harbor Laboratory Press (1989)). Also, the cDNAs encoding and VL can be prepared through polymerase chain reaction (hereinafter referred to as "PCR"; *Molecular Cloning, A Laboratory Manual,* Second Edition, Cold Spring Harbor Laboratory Press (1989); *Current Protocols in Molecular Biology,* Supplement 1-34) by preparing primers and using cDNA prepared from mRNA or a cDNA library as the template.

The nucleotide sequence of the cDNA can be determined by digesting the cDNA selected by the above method with appropriate restriction enzymes and the like, cloning the fragments into a plasmid such as pBluescript SK(−) (manufactured by Stratagene), carrying out the reaction by a usually used nucleotide analyzing method such as the dideoxy method of Sanger, F. et al. (*Proc. Natl. Acad. Sci. USA,* 74, 5463 (1977)), and then analyzing the sequence using an automatic nucleotide sequence analyzer such as A.L.F. DNA sequencer (manufactured by Pharmacia).

Whether the obtained cDNAs encode the fill amino acid sequences of VL and VL of the antibody containing a secretory signal sequence can be confirmed by estimating the fill length of the amino acid sequences of VH and VL from the determined nucleotide sequence and comparing them with the frill length of the amino acid sequences of VH and VL of known antibodies (*Sequences of Proteins of Immunological Interest,* US Dept. Health and Human Services (1991)). The length of the secretory signal sequence and N-terminal amino acid sequence can be deduced by comparing the full length of the amino acid sequences of VH and VL of the antibody comprising a secretory signal sequence with fill length of the amino acid sequences of VH and VL of known antibodies (*Sequences of Proteins of Immunological Interest,* US Dept.

Health and Human Services (1991)), and the subgroup to which they belong can also be known. Furthermore, the amino acid sequence of each of CDRs of VH and VL can be found by comparing the obtained amino acid sequences with amino acid sequences of VH and VL of known antibodies (*Sequences of Proteins of Immunological Interest*, US Dept. Hearth and Human Services (1991)).

Moreover the novelty of the sequence can be examined by carrying out a homology search with sequences in any database, for example, SWISS-PROT, PIR-Protein or the like using the full length of the amino acid sequences of Et and VL, for example, according to the BLAST method (*J. Mol. Biol.*, 215, 403 (1990)) or the like.

(3) Construction of Human Chimeric Antibody Expression Vector cDNAs encoding VH and VL of antibody of non-human animal are cloned in the upstream of genes encoding CH or CL of human antibody of vector for expression of humanized antibody mentioned in the above 2(1) to thereby construct human chimeric antibody expression vector. For example, each cDNA encoding VH and VL of antibody of non-human animal is ligated to synthetic DNA comprising a nucleotide sequence of 3-terminal of VH or VL of antibody of non-human animal and a nucleotide sequence of 5'-terminal of CH or CL of human antibody and having recognition sequence of an appropriate restriction enzyme at both ends, and cloned so that each of them is expressed in an appropriate form in the upstream of gene encoding CH or CL of human antibody of the vector for expression of humanized antibody mentioned in the above 2(1) to construct human chimeric antibody expression vector. In addition, cDNA encoding VH or VL or non-human animal is amplified by PCR using a synthetic DNA having a recognition sequence of an appropriate restriction enzyme at both terminals and each of them is cloned to the vector for expression of humanized antibody mentioned in the above 2(1).

(4) Construction of cDNA Encoding V Region of Human CDR-Grafted Antibody cDNAs encoding VH or VL of a human CDR-grafted antibody can be obtained as follows. First, amino acid sequences of framework region (hereinafter referred to as "FR") in VH or VL of a human antibody to which amino acid sequences of CDRs in VH or VL of an antibody from a non-human animal antibody are transplanted are selected. Any amino acid sequences of FR in VH or VL of a human antibody can be used, so long as they are from human. Examples include amino acid sequences of FRs in VH or VL of human antibodies registered in database such as Protein Data Bank or the like, and amino acid sequences common to subgroups of FRs in VH or VL of human antibodies (*Sequences of Proteins of Immunological Interest*, US Dept, Health and Human Services (1991)), and the like. In order to produce a human CDR-grafted antibody having potent activity, amino acid sequences having high homology (at least 60% or more) with an amino acid sequence of FR in VH or VL of a target antibody from a non-human animal is preferably selected. Then, amino acid sequences of CDRs of VH or VL of the antibody from a non-human animal are grafted to the selected amino acid sequence of FR in VH or VL, respectively, to design each amino acid sequence of VH or VL of a human CDR-grafted antibody. The designed amino acid sequences are converted to DNA sequences by considering the frequency of codon usage found in nucleotide sequences of genes of antibodies (*Sequence of proteins of Immunological Interest*, US Dept. Health and Human Services (1991)), and the DNA sequence encoding the amino acid sequence of VH or VL of a human CDR-grafted antibody is designed. Based on the designed nucleotide sequences, several synthetic DNAs having a length of about 100 nucleotides are synthesized, and PCR is carried out using them. In this case, it is preferred in each of the H chain and the L chain that 6 synthetic DNAs are designed in view of the reaction efficiency of PCR and the lengths of DNAs which can be synthesized.

Furthermore, the cDNA encoding VH or VL of a human CDR-grafted antibody can be easily cloned into the vector for expression of humanized antibody constructed in the (1) of this item 2 by introducing the recognition sequence of an appropriate restriction enzyme to the 5' terminal of the synthetic DNAs existing on the both ends. After the PCR, an amplified product is cloned into a plasmid such as pBluescript SK (–) (manufactured by Stratagene) or the like, and the nucleotide sequence is determined according to the method described in (2) of this item 2 to obtain a plasmid having a DNA sequence encoding the amino acid sequence of VH or VL of a desired human CDR-grafted antibody.

(5) Modification of Amino Acid Sequence of V Region of Human CDR-Grafted Antibody It is known that when a human CDR-grafted antibody is produced by simply grafting only CDRs in VH and VL of an antibody from a non-human animal into FRs of VH and VL of a human antibody, its antigen-binding activity is lower than that of the original antibody from a non-human animal (*BIO/TECHNOLOGY*, 9, 266 (1991)). As the reason, it is considered that several amino acid residues in not only CDRs but also FRs directly or indirectly relate to antigen-binding activity in VH and VL of the original antibody derived from a non-human animal, and as a result of grafting of CDRs, such amino acid residues are changed to different amino acid residues of FRs in VH and VL of a human antibody. In order to solve the problem, in human CDR-grafted antibodies, among the amino acid sequences of FRs in VH and VL of a human antibody, an amino acid residue which directly relates to binding to an antigen, or an amino acid residue which indirectly relates to binding to an antigen by interacting with an amino acid residue in CDR or by maintaining the three-dimensional structure of an antibody is identified and modified to an amino acid residue which is found in the original non-human animal antibody to thereby increase the antigen binding activity which has been decreased [*BIO/TECHNOLOGY*, 9, 266 (1991)]. In the production of a human CDR-grafted antibody, how to efficiently identify the amino acid residues relating to the antigen binding activity in FR is most important, so that the three-dimensional structure of an antibody is constructed and analyzed by X-ray crystallography [*J. Mol. Biol.* 112, 535 (1977)], computer-modeling [*Protein Engineering*, 2, 1501 (1994)] or the like. Although the information of the three-dimensional structure of antibodies has been useful in the production of a human CDR-grafted antibody, no method for producing a human CDR-grafted antibody which can be applied to any antibodies has been established yet. Therefore, various attempts must be currently be necessary, for example, several modified antibodies of each antibody are produced and the correlation between each of the modified antibodies and its antibody binding activity is examined.

The modification of the amino acid sequence of FR in VH and VL of a human antibody can be accomplished using various synthetic DNA for modification according to PCR as described in (4) of this item 2. With regard to the amplified product obtained by the PCR, the nucleotide sequence is determined according to the method as described in (2) of this item 2 so that whether the objective modification has been carried out is confirmed.

(6) Construction of Human CDR-Grafted Antibody Expression Vector

A human CDR-grafted antibody expression vector can be constructed by cloning each cDNA encoding VH or VL of a constructed human CDR-grafted antibody into upstream of each gene encoding CH or CL of the human antibody in the vector for expression of humanized antibody as described in (1) of this item 2.

For example, when recognizing sequences of an appropriate restriction enzymes are introduced to the 5'-terminal of synthetic DNAs positioned at both ends among synthetic DNAs used in the construction of VH or VL of the human CDR-grafted antibody in (4) and (5) of this item 2, cloning can be carried out so that they are expressed in an appropriate form in the upstream of each gene encoding CH or CL of the human antibody in the vector for expression of humanized antibody as described in (1) of this item 2.

(7) Transient Expression of Humanized Antibodies

In order to efficiently evaluate the antigen binding activity of various humanized antibodies produced, the humanized antibodies can be expressed transiently using the humanized antibody expression vector as described in (3) and (6) of this item 2 or the modified expression vector thereof. Any cell can be used as a host cell, so long as the host cell can express a humanized antibody. Generally, COS-7 cell (ATCC CRL 1651) is used in view of its high expression amount (*Methods in Nucleic Acids Res.*, CRC Press, p. 283 (1991)). Examples of the method for introducing the expression vector into COS-7 cell include a DEAE-dextran method (*Methods in Nucleic Acids Res.*, CRC Press, p. 283 (1991)), a lipofection method (*Proc. Natl. Acad. Sci. USA*, 84: 7413 (1987)), and the like.

After introduction of the vector, the expression amount and antigen binding activity of the humanized antibody in the culture supernatant can be determined by the enzyme immunoassay (hereinafter referred to as "ELISA"; *Monoclonal Antibodies-Principles and practice*, Third edition, Academic Press (1996), *Antibodies—A Laboratory Manual*, Cold Spring Harbor Laboratory (1988), *Monoclonal Antibody Experiment Manual*, Kodansha Scientific (1987)) and the like.

(8) Stable Expression of Humanized Antibody

A transformant which stably expresses a humanized antibody can be obtained by introducing into an appropriate host cell the humanized antibody expression vector described in (3) and (6) of this item 2.

Examples of the method for introducing the expression vector into a host cell include electroporation (Japanese Published Unexamined Patent Application No. 257891/90, *Cytotechnology*, 3, 133 (1990)) and the like.

A the animal cell into which a humanized antibody expression vector is introduced, any cell can be used, so long as it is an animal cell which can produce the humanized antibody. Examples include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR") is defective (*Proc. Nat. Acad. Sci, U.S.A.,* 77, 4216 (1980)), lection resistance-acquired Lec13 [*Somatic Cell and Molecular genetics,* 12, 55 (1986)], CHO cell in which α1,6-fucosyltransaferse gene is defected (WO05/35586), rat YB2/3HL.P2.G11.16Ag.20 cell (ATCC CRL1662), and the like.

In addition to the above host cells, host cells in which activity of a protein such as an enzyme relating to synthesis of an intracellular sugar nucleotide, GDP-fucose a protein such as an enzyme relating to the modification of a sugar chain in which 1-position of fucose is bound to 6-position of N-acetyl-glucosamine in the reducing end through α-bond in a complex type N-glycoside-linked sugar chain, or a protein relating to transport of an intracellular sugar nucleotide, GDP-fucose, to the Golgi body are introduced is decreased or deleted, preferably CHO cell in which α1,6-fucosyltransferase gene is defected as described in WO05/35536, can also be used.

After introduction of the expression vector, transformants which express a humanized antibody stably are selected in accordance with the method disclosed in Japanese Published Unexamined Patent Application No. 257391/90, by culturing in a medium for animal cell culture containing an agent such as G418 sulfate (hereinafter referred to as "G418", manufactured by Sigma) or the like. Examples of the medium for animal cell culture include RPMI1640 medium (manufactured by Invitrogen), GIT medium (manufactured by Nissui Pharmaceutical), EX-CELL301 medium (manufactured by JRH), IMDM medium (manufactured by Invitrogen), Hybridoma-SFM medium (manufactured by Invitrogen), media obtained by adding various additives such as fetal bovine serum (hereinafter referred to as "FBS") to these media, and the like. The humanized antibody can be produced and accumulated in a culture supernatant by culturing the selected transformants in a medium. The expression amount and antigen binding activity of the humanized antibody in the culture supernatant can be measured by ELISA or the like. Also, in the transformant, the expression amount of the humanized antibody can be increased by using dhfr amplification system or the like according to the method disclosed in Japanese Published Unexamined Patent Application No. 257891/90.

The humanized antibody can be purified from the culture supernatant of the transformant by using a protein A column [*Monoclonal Antibodies—Principles and practice*, Third edition, Academic Press (1996), *Antibodies—A Laboratory Manual*, Cold Spring Harbor Laboratory (1988)]. Any other conventional methods for protein purification can be used. For example, the humanized antibody can be purified by a combination of gel filtration, ion-exchange chromatography, ultrafiltration and the like. The molecular weight of the H chain or the L chain of the purified humanized antibody or the antibody molecule as a whole is determined by polyacrylamide gel electrophoresis (hereinafter referred to as "SDS-PAGE") [*Nature,* 227, 680 (1970)], Western blotting [*Monoclonal Antibodies—Principles and practice*, Third edition, Academic Press (1996), *Antibodies—A Laboratory Manual*, Cold Spring Harbor Laboratory (1988)], and the like.

3. Evaluation of Activity of Antibody or Antibody Fragment of the Present Invention The binding activity to an antigen and the binding activity to a PERP-expressing cell line of the purified antibody or antibody fragment of the present invention can be determined by ELISA, an immunofluorescent method (*Cancer Immuno Immunother.,* 36, 373 (1993)), surface plasmon resonance using, for example, BIAcore™, or the like. The cytotoxic activity against an antigen positive culture cell line can be evaluated by measuring the CDC activity, the ADCC activity or the like (*Cancer Immunol. Immunother,* 36: 373 (1993)).

4. Diagnostic Method of Disease Using Antibody of the Present Invention

Expression of polypeptide encoded by PERP gene is recognized in specific cells and, therefore, the disease relating to the polypeptide can be diagnosed by detecting or quantitatively determining the polypeptide encoded by PERP gene or cells in which the polypeptide is expressed using the antibody or the antibody fragment of the present invention.

The disease relating to the polypeptide encoded by the PERP gene is not limited, so long as it is a disease relating to a cell in which the polypeptide is expressed, and cancer is exemplified. The cancer includes cancer derived from epidermis, such as breast cancer, uterine cancer, colorectal cancer, stomach cancer, ovarian cancer, lung cancer, renal cancer, rectal cancer, thyroid cancer, uterine cervix cancer, small intestinal cancer, prostate cancer and pancreatic cancer.

A biological sample to detect or determine the polypeptide encoded by the PERP gene in the present invention is not limited, so long as it has possibility of containing the polypeptide such as tissue cells, blood, plasma, serum, pancreatic juice, urine, feces, tissue solution and culture solution.

The disease relating to the polypeptide encoded by the PERP gene includes a disease where its expression varies by the disease, such as cancer.

Diagnosis of cancer can be carried out, for example, as follows.

Thus, detection or determination of a polypeptide encoded by the PERP gene is carried out for biological samples collected from living body of plural healthy persons by the following immunological method using the antibody or antibody fragment of the present invention, or derivatives thereof whereby the existing amount of the polypeptide in biological samples of healthy persons is tested. Biological samples of the subjects are also tested for the existing amount of the polypeptide in the similar manner and the existing amount is compared with that of healthy persons. When the existing amount of the polypeptide in the subjects is more than that of healthy persons, it can be diagnosed that cancer is positive.

The diagnostic agent containing the antibody or antibody fragment of the present invention or derivatives thereof may further contain a reagent for carrying out an antigen-antibody reaction or a reagent for detection of the reaction depending on the desired diagnostic method. The reagent for carrying out the antigen-antibody reaction includes buffer, salt, and the like. The reagent for detection includes a reagent used for common immunological detection or immunoassay such as antibody or antibody fragment, derivatives thereof labeled secondary antibody for recognizing the antibody, antibody fragment or derivatives thereof and substrate corresponding to the labeling.

As a method for detection or determination of the amount of the polypeptide encoded by PERP gene in the present invention, any known method may be included. For example, an immunological detection method or immunoassay may be exemplified.

An immunological detection or immunoassay is a method in which an antibody amount or an antigen amount is detected or determined using a labeled antigen or antibody. Examples of the immunological detection or immunoassay are radioactive substance-labeled immunoantibody method (RIA), enzyme immunoassay (EIA or ELISA), fluorescent immunoassay (FIA), luminescent immunoassay, Western blotting method and physico-chemical means (TIA, LAPIA and PCIA). Although any method may be used, so long as it is a method for carrying out detection or determination of an antigen, preferred methods are immunoprecipitation method and fluorescent cell staining method.

As an example of the radioactive substance-labeled immunoantibody method (RIA), a method, in which the antibody of the present invention is allowed to react with an antigen or a cell expressing an antigen, then anti-immunoglobulin antibody subjected to radioactive labeling or a binding fragment thereof is allowed to react therewith, followed by determination using a scintillation counter or the like, is mentioned.

As an example of the enzyme immunoassay (EIA or ELISA), a method, in which the antibody of the present invention is allowed to react with an antigen or a cell expressing an antigen, then anti-immunoglobulin antibody or the antibody fragment subjected to antibody labeling is allowed to react therewith and the colored pigment is measured by a spectrophotometer, is mentioned and, for example, sandwich ELISA may be used. As a label used in the enzyme immunoassay, any known enzyme label (*Enzyme Immunoassay* edited by Eiji Ishikawa, et al. published by Igaku Shoin) may be used as described already. For example, alkaline phosphatase labeling, peroxidase labeling, luciferase labeling or biotin labeling may be used.

Sandwich ELISA is a method in which an antibody is bound to a solid phase, antigen to be detected or measured is trapped and another antibody is allowed to react with the trapped antigen. In the ELISA, 2 kinds of antibody which recognizes the antigen to be detected or measured or the antibody fragment thereof in which antigen recognizing site is different are prepared and one antibody or antibody fragments is previously adsorbed on a plate (such as a 96-well plate) and another antibody of antibody fragment is labeled with a fluorescent substance such as FITC, an enzyme such as peroxidase, or biotin. The plate to which the above antibody is adsorbed is allowed to react with the cell separated from living body or disrupted cell suspension thereof, tissue or disintegrated solution thereof cultured cells, serum, pleural effusion, ascites, eye solution or the like, then allowed to react with labeled monoclonal antibody or antibody fragment and a detection reaction corresponding to the labeled substance is carried out. When an antigen concentration in the sample to be tested is measured by the method, antigen concentration in the sample to be tested can be calculated from a calibration curve prepared by a stepwise dilution of antigen of known concentration. As antibody used for sandwich ELISA, any of polyclonal antibody and monoclonal antibody may be used or antibody fragments such as Fab, Fab' and F(ab)$_2$ may be used. As a combination of 2 kinds of antibodies used in sandwich ELISA, a combination of monoclonal antibodies or antibody fragments recognizing different epitopes may be used or a combination of polyclonal antibody with monoclonal antibody or antibody fragments may be used.

A fluorescent immunoassay (FIA) includes a method described in the literatures [*Monoclonal Antibodies—Principles and practice*, Third Edition, Academic Press (1996); *Manual for Monoclonal Antibody Experiments*, Kodansha Scientific (1987)] and the like. As a label for the fluorescent immunoassay, any of known fluorescent labels (*Fluorescent Immunoassay*, by Akira Kawao, Soft Science) may be used as described already. For example, FITC labeling, RITC labeling or the like may be used.

As a label used for luminescent immunoassay, any of known luminescent labels [*Bioluminescence and Chemical Luminescence*, Hirokawa Shoten; *Rinsho Kensa*, 42 (1998)] may be included as described above. For example, acridinium ester labeling, lophine labeling or the like may be used.

Western blotting method is a method in which an antigen or a cell expressing an antigen is fractionated by SDS-polyacrylamide gel electrophoresis [*Antibodies—A Laboratory Manual* (Cold Spring Harbor Laboratory, 1988)], the gel is blotted onto PVDF membrane or nitrocellulose membrane, the membrane is allowed to react with antigen-recognizing antibody or antibody fragment, further allowed to react with an anti-mouse IgG antibody or antibody fragment which is labeled with a fluorescent substance such as FITC, an enzyme label such as peroxidase, a biotin labeling, or the like, and the label is visualized to confirm the reaction. An example of the Western blotting method is described below.

Cells and tissues in which a polypeptide having the amino acid sequence represented by SEQ ID NO:2 is expressed are dissolved in a solution and, under reducing conditions, 0.1 to 30 μg as a protein amount per lane is electrophoresed by an SDS-PAGE method. The electrophoresed protein is transferred to a PVDF membrane and allowed to react with PBS containing 1% of BSA (hereinafter referred to as "BSA-PBS") at room temperature for 30 minutes for blocking. Here, the monoclonal antibody of the present invention is allowed to react therewith, washed with PBS containing 0.05% Tween 20 (hereinafter referred to as "Tween-PBS") and allowed to react with goat anti-mouse IgG labeled with peroxidase at room temperature for 2 hours. It is washed with Tween-PBS and a band to which the monoclonal antibody is bound is detected using ECL™ Western Blotting Detection Reagents (manufactured by Amersham) or the like to thereby detect a polypeptide having the amino acid sequence represented by SEQ ID NO:2. As an antibody used for the detection in Western blotting, an antibody which can be bound to a polypeptide having no three-dimensional structure of a natural type is used. Specifically, the monoclonal antibody KM3314 described in (2) of Example 4 of the present invention or a commercially available anti-PERP polyclonal antibody (manufactured by ProSci, product No. 2451; manufactured by Novus Biologicals, product No. NH500-231) and the like may be used.

In the physico-chemical method, specifically, an aggregate is formed through binding of the antibody of the present invention to a polypeptide encoded by the PERP gene which is an antigen using the antibody of the present invention which specifically binds to a polypeptide encoded by PERP gene and the resulting aggregate is detected. Other examples of the physico-chemical methods include a capillary method, a one-dimensional immunodiffusion method, an immunoturbidimetry and a latex immunoturbidimetry [*Handbook of Clinical Test Methods*, Kanehara Shuppan, 499 (1988)].

For example, in a latex immunodiffusion method, a carrier such as polystyrene latex having a particle size of about of 0.1 to 1 μm sensitized with antibody or antigen may be used and when an antigen-antibody reaction is carried out using the corresponding antigen or antibody, scattered light in the reaction solution increases while transmitted light decreases. When such a change is detected as absorbance or integral sphere turbidity, it is now possible to measure antigen concentration, etc. in the sample to be tested.

The antibody of the present invention specifically recognizes three-dimensional structure of an extracellular region of a polypeptide encoded by the PERP gene and binds to the extracellular region and, therefore, it is advantageously used for the detection of cells in which the polypeptide is expressed.

For detection of the cells in which the polypeptide is expressed, known immunological detection methods may be used, and an immunoprecipitation method, a fluorescent cell staining method and an immune tissue staining method are preferably used. Also, an immunofluorescent staining method using FMAT 8100 HTS system (Applied Biosystem) and the like can be used.

An immunoprecipitation method is a method in which a cell expressing the polypeptide or the like is allowed to react with the monoclonal antibody or antibody fragment of the present, invention and then a carrier having specific binding ability to immunoglobulin such as protein G-Sepharose is added so that an antigen-antibody complex is precipitated. Also, the following method may be carried out.

The above-described antibody of the present invention is adsorbed on a 96-well plate for ELISA and then blocked with BSA-PBS. When the antibody is in a non-purified state such as a culture supernatant of hybridoma cell, anti-mouse immunoglobulin or rat immunoglobulin or protein A or G or the like is previously adsorbed on a 96-well plate for ELISA and blocked with BSA-PBS and a culture supernatant of hybridoma cell is dispensed thereto for binding. After BSA-PBS is discarded and the residue is sufficiently washed with PBS, reaction is carried out with a dissolved solution of cells or tissues in which polypeptide having an amino acid sequence represented by SEQ ID NO:2 is expressed. An immune precipitate is extracted from the well-washed plate with a sample buffer for SDS-PAGE and detected by the above-described Western blotting.

An immune cell staining method and an immune tissue staining method are immunofluorescent staining methods (a flow cytometry) where cells or tissues in which antigen is expressed are treated, if necessary, with a surfactant or methanol to make an antibody easily permeate to the cells or tissues, then the antibody of the present invention is allowed to react therewith, then further allowed to react with anti-immunoglobulin antibody or antibody fragment subjected to fluorescent labeling such as FITC, enzyme label such as peroxidase or biotin labeling and the label is visualized and observed under a microscope or cells are allowed to react with a fluorescence-labeled antibody and analyzed by a flow cytometer. That can be carried out by the methods described, for example, in the literatures [*Monoclonal Antibodies—Principles and practice*, Third Edition, Academic Press (1996), *Manual for Experiments of Monoclonal Antibodies*, Kodansha Scientific (1987)]. Particularly, since the antibody of the present invention specifically recognizes three-dimensional structure of an extracellular region of a polypeptide encoded by the PERP gene and binds to the extracellular region, it can be preferably used for detection of a cell which expresses a polypeptide encoded by the PERP gene of a natural type and maintaining the three-dimensional structure by a flow cytometry.

The immunofluorescent staining method using FMAT 8100 HTS system (Applied Biosystem) is a homogeneous assay method in which an antigen amount and an antibody amount can be measured without separating the formed antibody-antigen complex and free antibody or antigen which does not relate to formation of the antibody-antigen complex and, specifically, a method described in (3)-3 of Example 4 may be exemplified.

5. Method for Treating Disease Using the Antibody of the Present Invention

The antibody of the present invention which specifically recognizes three-dimensional structure of an extracellular region of a polypeptide encoded by the PERP gene or antibody fragment thereof can be used for the treatment of diseases relating to the polypeptide encoded by the PERP gene.

The disease relating to the polypeptide encoded by the PERP gene is not limited, so long as it is a disease relating to a cell expressing the polypeptide, such as cancer. The cancer includes cancer derived from epidermis, such as breast cancer, uterine cancer, colorectal cancer, stomach cancer, ovarian cancer, lung cancer, renal cancer, rectal cancer, thyroid cancer, uterine cervix cancer, small intestinal cancer, prostate cancer and pancreatic cancer.

A therapeutic agent for cancer using the antibody for a polypeptide encoded by the PERP gene includes a therapeutic agent for cancer which comprises regulating activity of a polypeptide encoded by the PERP gene by using the antibody and a therapeutic agent for cancer by ADCC activity and CDC activity or by an apoptosis-inducing activity.

ADCC activity and CDC activity of the antibody can be measured by a method described, for example, in Japanese Published Unexamined Patent Application No. 205694/94. The antibody having such activity can injure the cell in which a specific antigen is expressed in vivo and, therefore, it can be used as a therapeutic agent for the disease. A humanized antibody and a human antibody such as a human chimeric antibody having an antibody constant region of human IgG class and a human CDR-grafted antibody and a human antibody can be effectively used as therapeutic agents [*Cancer Res.*, 56, 1118 (1996)].

The antibody of the present invention can recognize the natural-type polypeptide encoded by the PERP gene which is not denatured and, therefore, it can recognize the cell in which polypeptide encoded by PERP gene existing in living body. Accordingly, a humanized antibody such as a human chimeric antibody and a human CDR-grafted antibody having an antibody constant region of human IgG class including CDR of a variable region of the antibody and a human antibody can injure the cell in which polypeptide encoded by PERP gene is expressed in vivo or in vitro. Since expression of PERP gene is promoted in cancer, the antibody of the present invention or antibody fragment of the present invention can be used as a therapeutic agent for cancer. In addition, the antibody of the present invention which has high ADCC activity is used particularly effectively as a therapeutic agent for the treatment to decrease the cells in which the antibody is expressed.

The therapeutic agent comprising the antibody or antibody fragment of the present invention or a derivative thereof may contain only the antibody or antibody fragment of the present invention or a derivative thereof as an active ingredient, but generally, it is preferred to provide it as a pharmaceutical preparation produced by an appropriate method well known in the technical field of pharmaceutics, by mixing it with one or more pharmaceutically acceptable carriers.

It is preferred to select a route of administration which is most effective in treatment. Examples include oral administration and parenteral administration, such as buccal, tracheal, rectal, subcutaneous, intramuscular or intravenous administration. In the case of an antibody or peptide formulation, intravenous administration is preferred. The dosage form includes sprays, capsules, tablets, granules, syrups, emulsions, suppositories, injections, ointments, tapes and the like.

The pharmaceutical preparation suitable for oral administration includes emulsions, syrups, capsules, tablets, powders, granules and the like. Liquid preparations such as emulsions and syrups can be produced using, as additives, water; sugars such as sucrose, sorbitol and fructose; glycols such as polyethylene glycol and propylene glycol; oils such as sesame oil, olive oil and soybean oil; antiseptics such as p-hydroxybenzoic acid esters; flavors such as strawberry flavor and peppermint; and the like. Capsules, tablets, powders, granules and the like can be produced using, as additives, excipients such as lactose, glucose, sucrose and mannitol; disintegrating agents such as starch and sodium alginate; lubricants such as magnesium stearate and talc; binders such as polyvinyl alcohol, hydroxypropylcellulose and gelatin; surfactants such as fatty acid ester; plasticizers such as glycerin; and the like.

The pharmaceutical preparation suitable for parenteral administration includes injections, suppositories, sprays and the like. Injections can be prepared using a carrier such as a salt solution, a glucose solution or a mixture of both thereof. Suppositories can be prepared using a carrier such as cacao butter, hydrogenated fat or carboxylic acid. Sprays can be prepared using the antibody or antibody fragment as such or using it together with a carrier which does not stimulate the buccal or airway mucous membrane of the patient and can facilitate absorption of the compound by dispersing it as fine particles. The carrier includes lactose, glycerol and the like. Depending on the properties of the antibody and the carrier, it is possible to produce pharmaceutical preparations such as aerosols and dry powders. In addition, the components exemplified as additives for oral preparations can also be added to the parenteral preparations.

Although the dose or the frequency of administration varies depending on the objective therapeutic effect, administration method, treating period, age, body weight and the like, it is usually 10 μg/kg to 8 mg/kg per day and per adult.

BRIEF DESCRIPTION OF THE DRAWINGS

FIG. 5 shows reactivity of KM3411 in FMAT. In the graph, the ordinate shows the integral value of fluorescence intensity and cell numbers.

Figure 1:
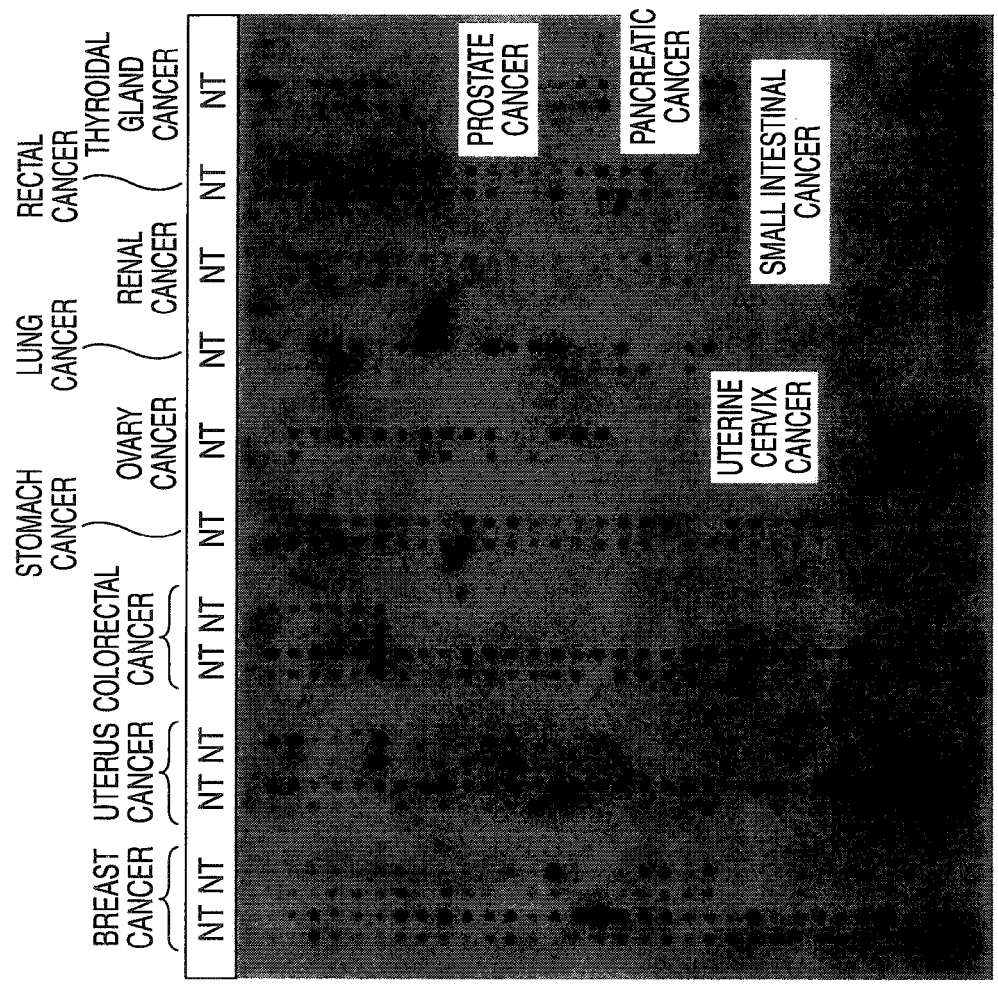
FIG. 1 shows the result of analyzing expression of PERP in various clinical cancer tissues and neighboring non-cancer tissues using Cancer Profiling Array. Types of cancers are shown in the drawing. N shows a non-cancerous area and T shows a cancerous area.

The present invention is explained below in detail based on Examples; however the present invention is not limited to the following Examples.

EXAMPLES

Example 1

Analysis for Expressing the PERP Gene in Various Cell Lines, Xenografts and Normal Tissues (1) Preparation of Various Kinds of Xenografts and Preparation of Tumor Mass Xenografts to which each of human pancreatic cancer cell lines [ASPC-1 cell line (ATCC CRL-1469), Capan-1 cell line (ATCC HTB-79), MiaPaca cell line (provided by National Cancer Center in Japan)] and cells derived from tumor cells of patients suffering from three types of human pancreatic cancers (PC01, PC02 and PC03) was transplanted were prepared as follows.

A cell suspension was prepared using PBS to give a cell density of $1 \times 10^8$ cells/ml each using each of cell lines subcultured in RMPI 1640 medium (manufactured by Invitrogen) containing 10% inactivated fetal bovine serum. Into ventral hypodermis of Fox CHASE C.B-17/Icr-scidJcl mouse (male, 5 weeks old, purchased from CLEA Japan, Inc.), 100 μL of the suspension was transplanted for each mouse. Diameter of tumor of the mouse in which adhesion of the transplanted cell line or cell was recognized was measured day by day using vernier calipers. The mouse in which the major axis of the tumor became about 1 cm was sacrificed by bleeding under anesthetization and then each tumor mass was excised. Each tumor mass was cut into 4 portions and quickly frozen using liquid nitrogen.

Xenografts to which each of human pancreatic cell lines PANC-1 cell line and PSN-1 cell line was transplanted were prepared as follows.

A cell suspension was prepared using serum-free RPMI 1640 medium to give a cell density of $8 \times 10^7$ to $1 \times 10^8$ cells/ml each using each of cell lines subcultured in RPMI 1640 medium (manufactured by Invitrogen) containing 5% inactivated fetal bovine serum. Into ventral hypodermis of BALB/cAJcl-nu mouse (male, 8 weeks old, purchased from CLEA Japan, Inc.), 100 μL of the suspension was transplanted for each mouse, Diameter of tumor of the mouse in which adhesion of the transplanted cell line or cell was recognized was measured day by day using vernier calipers. The mouse in which the major axis of the tumor became about 1 cm was slaughtered by dislocation of cervical vertebra and then each tumor mass was excised. Each tumor mass was cut into 4 portions and quickly frozen using liquid nitrogen.

Xenografts to which each of human colorectal cancer cell lines HT-29 cell line (AT CC HTB-38) and WiDr cell line (ATCC CCL-218) was transplanted were prepared as follows.

A cell suspension was prepared using serum-free RPMI 1640 medium to give a cell density of $1 \times 10^7$ cells/ml each using either HT-29 cell line subcultured in MaCoy's 5A medium (manufactured by Invitrogen) containing 10% inactivated bovine serum or WiDr cell line subcultured in HEM medium (manufactured by Invitrogen) containing 10% inactivated bovine serum. Into ventral hypodermis of BALB/cAJcl-nu mouse (male, 8 weeks old, purchased from CLEA Japan, Inc.), 100 μL of the suspension was transplanted. Diameter of tumor of the mouse in which adhesion of the transplanted cell line was recognized was measured day by day using vernier calipers. The mouse in which the diameter of the tumor became about 1 cm was slaughtered by dislocation of cervical vertebra and then each tumor mass was excised. Each tumor mass was cut into 4 portions and quickly frozen using liquid nitrogen.

Xenografts to which each of human colorectal cancer cell lines Colo 205 cell line (ATCC CCL-222), LS 174T cell line (ATCC CL-188), LS 180 cell line (ATCC CL-S87) and SW 1116 cell line (ATCC CCL-233) was transplanted were prepared as follows.

A cell suspension was prepared using PBS to give a cell density of $1 \times 10^8$ cells/ml each using an RPMI 1640 medium (manufactured by Invitrogen) containing 10% inactivated fetal bovine serum. Into ventral hypodermis of Fox CHASE C.B-17/Icr-scidJcl mouse (male, 5 weeks old, purchased from CLEA Japan, Inc.), 100 μL of the suspension was transplanted. Tumor mass excised from the thus obtained xenograft was transplanted into ventral hypodermis of the mouse of the same cell line and diameter of tumor of the mouse in which the transplanted tumor mass was adhered was measured day by day using vernier calipers. The mouse in which the major axis of the tumor became about 1 cm was sacrificed by bleeding under anesthetization and then each tumor mass was excised. Each tumor mass was cut into 4 portions and quickly frozen using liquid nitrogen,
(2) Extraction of Total RNA and Purification of polyA(+) RNA Cell suspensions were prepared from cell lines, tissues of patients and xenografts prepared in the above (1) by the following method, and then total RNA was extracted and polyA(+) RNA was purified.

Thus, a cell disruption solution was prepared from each of 5 different types of cell lines derived from pancreatic cancer [ASPC-1 cell line (ATCC CRL-1469), BxPC-3 cell line (ATCC CRL-1687), Capan-1 cell line (ATCC HTB-79) and MiaPaca cell line (received from National Cancer Center in Japan), PSN-1 cell line], 8 different types of cell lines derived from colorectal cancer [Colo 205 cell line (ATCC CCL-222), HT-29 cell line (ATCC HTB-38), LS 174T cell line (ATCC CL-188), LS 180 cell line (ATCC CL-187) and SW 1116 cell line (ATCC CCL-233)], 7 different types of non-small-cell lung cancer cell lines {PC-1 cell line, PC-7 cell line, PC-9 cell line and PC-12 cell line [these four cell lines are described in *British Journal of Cancer*, 39, 15 (1976)], PC-14 cell line (ECACC 90071810), SK-LU 1 cell line (ATCC HUB-57) and SK-LC-4 cell line}, 4 different types of small-cell lung cancer cell lines [Lu-139 cell line (RCB 469), NCI-H69 cell line (ATCC HTB-119), RERF-LC-MA cell line (JCRB 0812) and SBC-5 cell line (JCRB 0819)], 3 different types of acute myelogenous leukemia (AML) cell lines [KG-1 cell line (ATCC CCL-246), THP-1 cell line (ATCC CRL-8031) and HL-60 cell line (ATCC CCL-240)], 3 different types of acute lymphocytic leukemia (ALL) cell lines [CCRF-CEM cell line (ATCC CCL-120), Jurkat cell line (ATCC TIB-152) and HSB-2 cell line (ATCC CCL-120.1), 2 different types of chronic myelogenous leukemia (CML) cell lines [K562 cell line (ATCC CCL-243) and KU 812 cell line (ATCC CRL-2099)], 8 different types of multiple myeloma cell lines [KMS-11 cell line [*International Journal of Oncology*, 12, 545 (1998)], KMS-18 cell line [*International Journal of Oncology*, 12, 545 (1998)], ARH-77 cell line (ATCC CRL-1621), IM-9 cell line (ATCC CCL-159), RPMI 8226 cell line (ATCC CCL-155), HS-Sultan cell line (ATCC CRL-1484), U266B1 cell line (ATCC TIB-196) and MC-CAR cell line (ATCC CRL-8083)], 2 different types of Burkitt's lymphoma cell line [Daudi cell line (ATCC CCL-213) and Raji cell line (ATCC CCL-86)], histiocytic lymphoma cell line [U937 cell line (ATCC CRL-1593)] and thyroidal follicular cancer (FTC) cell line [ML-1 cell line (D[SMZ ACC 464)] and then RNA was extracted from each of them as follows.

In the case of adhesive cell lines, the medium was removed using an aspirator after culturing, washing with a PBS was carried out and cells were recovered using a spatula made of silicone. They were suspended by adding 1 mL of TRIzoL Reagent (manufactured by Invitrogen) to the cells corresponding to 10 cm$^2$ of cultured area and passed through a 18 G injection needle 10 times to cleave the genomic DNA into pieces to thereby prepare a cell disruption solution.

In the case of floating cell lines, the cell culture was centrifuged at 1,500 rpm for 5 minutes using a refrigerated centrifuge (Hitachi Himac CF15R, w/T11A21 rotor), the medium was removed by decantation and the cells were suspended in PBS. The cell suspension was centrifuged at 1,500 rpm for 5 minutes using a refrigerated centrifuge (Hitachi Himac CF15R, w/T11A21 rotor) and the supernatant was removed to recover the cells. To $1\times10^7$ recovered cells was added 1 mL of TRIzoL Reagent (manufactured by Invitrogen), and the resulting suspension was passed through a 18 G injection needle 10 times to cleave the genomic DNA into pieces to thereby prepare a cell disruption solution.

Disruption of the xenograft prepared in the above (1) and that of the tumor mass excised from human clinical tissues were carried out as follows.

Frozen tumor mass was poured into 10 mL of TRIzoL Reagent (manufactured by Invitrogen) and immediately disrupted using Polytron PT 2100 (manufactured by Kinematica) at 30,000 rpm for 15 seconds to give a cell disruption solution.

Each of the cell disruption solutions was centrifuged at 11,000 rpm for 10 minutes using a refrigerated centrifuge (Hitachi Himac CF15R, w/T11A21 rotor) and, paying attention not to take out the precipitate, each of the supernatant was transferred to a new tube. To the supernatant was added 2 mL of chloroform, followed by vigorously stirring for 15 seconds, and the mixture was allowed to stand at room temperature for 2 to 3 minutes and centrifuged at 3,000 rpm for 90 minutes at 4° C. using a refrigerated centrifuge (Hitachi Himac CF7D2, w/RT3S3 rotor). Each of the supernatants was transferred to a new tube, 5 mL of isopropanol was added and gently mixed, the mixture was allowed to stand at room temperature for 10 minutes and centrifuged at 11,000 rpm for 10 minutes using a refrigerated centrifuge (Hitachi Himac CF15R, w/T11A21 rotor) and, after removing the supernatant, 10 mL of 75% ethanol solution was added thereto, followed by mixing and centrifugation at 11,000 rpm for 5 minutes using a refrigerated centrifuge (Hitachi Himac FC15R, w/T11A21 rotor) to give precipitate. The precipitate was dissolved in an appropriate amount of RNase-free water to prepare a total RNA sample. The concentration of the total RNA sample was measured and purity of the total RNA sample was tested and it was confirmed that the ratio of A260/A280 was 1.7 or more. When the ratio of A260/A80 was less than 1.7, further purification was carried out using RNeasy kit (manufactured by Qiagen).

From the total RNA prepared as above, polyA(+) RNA was purified using Micro Poly(A) Pure Kit (manufactured by Ambion) according to a protocol attached to the kit.
(3) Synthesis of cDNA cDNA was synthesized from the polyA(+) RNA obtained in the above (2) or commercially available mRNA using a SuperScript First-Strand Synthesis System for RT-PCR (manufactured by Invitrogen) according to the manual attached to the kit.

As mRNA derived from human normal tissues, mRNAs derived from blood, large intestine, heart, kidney, liver, lung, lymph node, pancreas, prostate gland, salivary gland, skeletal muscle, small intestine, spinal cord, spleen, stomach, testis, thymus gland, thyroid gland, trachea, uterus and placenta were purchased from BD Clontech and used. As the human clinical cancer excision tissue, mRNAs derived from clear cell cancer of kidney (moderately differentiated cancer and highly differentiated cancer) [a mixture from 9 cases of male patients of 35 to 71 years old and 6 cases of female patients of 44 to 63 years old], hepatic cell cancer (lowly differentiated cancer) [a mixture from one case of a 69-year-old male patient and one case of a 67-year-old female patient], lung squamous cancer [a mixture from 5 cases of a male patient of 46 to 70 years old], cancer of gastric gland (lowly differentiated cancer, moderately differentiated cancer and highly differentiated cancer) [a mixture from 7 cases of male patients cell 46 to 81 years old and 2 cases of female patients cell 47 to 58 years old], uterine fibroid [a mixture from 5 cases of female patients cell 29 to 52 years old], infiltrative mammary duct cancer (moderately differentiated cancer) [a mixture from 6 cases of female patients 45 to 60 years old] and esophageal squamous cancer (lowly differentiated cancer, moderately differentiated cancer and highly differentiated cancer) [a mixture from 4 cases of male patients of 56 to 78 years old and one case of a 71-year-old female patient] was purchased from BioChain and used for the experiments.

To 1 μg of mRNA were added 1 μL of a mixed solution of 10 mmol/L dNTPs and 1 μL of 0.5 μg/μL Oligo (dT)$_{12-18}$ primer solution, DEPC water was added thereto to give a total amount of 7 μL and the reaction solution was heated at 65° C. for 5 minutes, quickly cooled on ice and allowed to stand for one minute or longer for denaturing. To the MA solution were added 2 μL of 10×RT buffer, 4 μL of 25 μmol/L magnesium chloride, 2 μL of 0.1 mol/L DTT and 1 μL of RNase OUT to give a total amount of 19 μL and the temperature was kept at 42° C. for 2 minutes. Furthermore, 1 μL of Superscript II RTase (50 U) was further added thereto to carry out reverse transcription reaction at 42° C. for 50 minutes, followed by heating at 70° C. for 15 minutes to inactivate the enzyme. Then, 1 μL of RNaseH was added thereto and, after the reaction at 37° C. for 20 minutes, DEPC water was added thereto to give a total amount of 1 μL. For the real-time PCR, the solution was diluted 5-fold and used.

(4) Quantitative Determination of Amount of MA of the PERP Gene in Cell Lines, Xenografts and Normal Tissues by Real-Time PCR Method (Q-PCR Method)

Each of cDNA (10 μL) prepared in the above (3) (corresponding to 2 ng of polyA(+) RNA), a forward primer containing the sequence represented by SEQ ID NO:5 and a reverse primer containing the sequence represented by SEQ ID NO:6 (all manufactured by Profligo) were added to give a final concentration of 300 nmol/L for each of them, and, further, a solution in which DEPC water was added to 2 μL of 10×R-PCR buffer Mg$^{2+}$ free (manufactured by Takara Bio), 0.2 μL of 250 mmol/L Mg$^{2+}$ solution, 0.6 μL of 10 mmol/L dNTPs, 0.2 μL of ExTaq R-PCR (manufactured by Takara Bio) and 1 μL of SYBR Green I (manufactured by BMA; original solution product was diluted 2,500-fold) to give a total amount of 20 μL was heated at 94° C. for 5 minutes and reaction was carried out by 45 cycles, one cycle consisting of reaction at 94° C. for 30 seconds, reaction at 65° C. for 30 seconds and reaction at 72° C. for 30 seconds. Fluorescence intensity generated by SYBR Green I intercalated to the amplified product was measured by PRISM 7700 (manufactured by PE Applied Biosystems) and data were analyzed according to the software, Sequence Detector ver. 1.7a, attached to the instrument.

Whether the signal obtained by the above reaction was the desired amplified fragment was judged by the size of the major amplified fragment obtained by subjecting the solution after completion of the reaction to agarose gel electrophoresis. Incidentally, the above reaction was carried out using a 96-well PCR plate. Besides the above cDNA, a negative control (sterile water) and a sample for preparation of a calibration curve (10 to $10^6$ copies/well) prepared using a plasmid PLACE 1001407 (Gen Bank Accession No. AK 075082) containing cDNA of the PERP gene purified by Qiagen Plasmid Prep Midi Kit (manufactured by Qiagen) were arranged as a sample in each well of the PCR plate and PCR was carried out in the same manner as above.

Results of the expression amount of mRNA of the PERP gene in each of the thus obtained samples are shown in Table 1 and Table 2.

TABLE 1

| Samples | | | | Number of Molecules | Ratio to Trachea |
|---|---|---|---|---|---|
| Pancreatic Cancer | | Cell line | ASPC-1 | 227,355 | 2.63 |
| | | | BXPC3 | 81,756 | 0.94 |
| | | | Capan-1 | 1,910 | 0.02 |
| | | | MiaPaca | 8,242 | 0.10 |
| | | | PSN-1 | 10,277 | 0.12 |
| | Derived from cell line | Xenograft | xASPC-1 | 479,761 | 5.54 |
| | | | xCapan-1 | 2,742 | 0.03 |
| | | | xMiaPaca | 66,753 | 0.77 |
| | | | xPSN-1 | 189 | 0.00 |
| | | | xPANC1 | 12,175 | 0.14 |
| | Derived from clinical tissues | | xPC01 | 12,128 | 0.14 |
| | | | xPC02 | 308,154 | 3.56 |
| | | | xPC03 | 295,033 | 3.41 |
| Colorectal Cancer | | Cell line | colo205 | 268,411 | 3.10 |
| | | | LS174T | 13,745 | 0.16 |
| | | | LS180 | 403 | 0.00 |
| | | | HT-29 | 52,134 | 0.60 |
| | | | SW1116 | 19,370 | 0.22 |
| | | Xenograft | xcolo205 | 50,072 | 0.58 |
| | | | xLS180 | 89 | 0.00 |
| | | | xHT-29 | 8,872 | 0.10 |
| | | | xSW1116 | 419 | 0.00 |
| | | | xWidr | 12,705 | 0.15 |
| Lung Cancer | Non-small-cell | Cell line | PC-1 | 22 | 0.00 |
| | | | PC-7 | 1,210 | 0.01 |
| | | | PC-9 | 4,117 | 0.05 |
| | | | PC-12 | 1,211 | 0.01 |
| | | | PC-14 | 5,948 | 0.07 |
| | | | SK-LC-1 | 1,798 | 0.02 |
| | | | SK-LC-4 | 61,414 | 0.71 |
| | Small-cell | | LU-139 | 1,521 | 0.02 |
| | | | NCI-H69 | 14,498 | 0.17 |
| | | | RERF-LC-MA | 5,127 | 0.06 |
| | | | SBC-5 | 59 | 0.00 |
| Blood Cancer | Acute myelogenous leukemia | Cell line | KG-1 | 90 | 0.00 |
| | | | THP-1 | 5,861 | 0.07 |
| | | | HL-60 | 35 | 0.00 |
| | Acute lymphocytic leukemia | Cell line | CCRF-CEM | 729 | 0.01 |
| | | | Jurkat | 170 | 0.00 |
| | | | HSB-2 | 373 | 0.00 |
| | Chronic myelogenous leukemia | Cell line | K562 | 1,408 | 0.02 |
| | | | KU812 | 97 | 0.00 |
| | Multiple myeloma | Cell line | KMS-11 | 57,260 | 0.66 |
| | | | KMS-18 | 40,538 | 0.47 |
| | | | ARH-77 | 2,638 | 0.03 |
| | | | IM-9 | 4,813 | 0.06 |
| | | | RPMI8226 | 1,711 | 0.02 |
| | | | HS-Sultan | 127 | 0.00 |
| | | | U266B1 | 527 | 0.01 |
| | | | MC-CAR | 91 | 0.00 |
| | Burkitt's lymphoma | Cell line | Daudi | 3 | 0.00 |
| | | | Raji | 107 | 0.00 |
| | Histocytic lymphoma | Cell line | U937 | 245 | 0.00 |
| Thyroidal follicular cancer | | Cell line | ML-1 | 389 | 0.00 |

TABLE 2

| Samples | | Number of molecules | Ratio to trachea |
|---|---|---:|---:|
| Clinical Tissues | Clear cell cancer of kidney — Cancer tissues | 351,564 | 4.06 |
| | Normal kidney tissues | 291 | 0.00 |
| | Hepatic cell cancer — Cancer tissues | 1,784 | 0.02 |
| | Normal liver tissues | 1,818 | 0.02 |
| | Lung squamous cancer — Cancer tissues | 19,062 | 0.22 |
| | Normal lung tissues | 5,965 | 0.07 |
| | Gastric gland cancer — Cancer tissues | 85,279 | 0.99 |
| | Normal stomach tissues | 2,635 | 0.03 |
| | Uterine fibroid — Cancer tissues | 638 | 0.01 |
| | Normal uterus tissues | 2,764 | 0.03 |
| | Infiltrative mammary duct cancer — Cancer tissues | 1,296 | 0.01 |
| | Esophageal squamous cancer — Cancer tissues | 732,569 | 8.46 |
| Normal Tissues | Blood | 1,353 | 0.02 |
| | Large intestine | 52,917 | 0.61 |
| | Heart | 17,483 | 0.20 |
| | Kidney | 5,497 | 0.06 |
| | Liver | 9,925 | 0.11 |
| | Lung | 25,936 | 0.30 |
| | Lymph node | 2,524 | 0.03 |
| | Pancreas | 24,464 | 0.28 |
| | Prostate gland | 67,919 | 0.78 |
| | Salivary gland | 14,978 | 0.17 |
| | Skeleton muscle | 1,271 | 0.01 |
| | Small intestine | 14,014 | 0.16 |
| | Spinal cord | 2,078 | 0.02 |
| | Spleen | 487 | 0.01 |
| | Stomach | 11,797 | 0.14 |
| | Testis | 8,046 | 0.09 |
| | Thymus gland | 4,190 | 0.05 |
| | Thyroid gland | 14,024 | 0.16 |
| | Airway | 86,550 | 1.00 |
| | Uterus | 7,603 | 0.09 |
| | Placenta | 29,848 | 0.34 |

Table 1 shows expression amounts of mRNA of the PERP gene in various cancer cell lines and xenografts and Table 2 shows expression amounts of mRNA of the PERP gene in clinical cancer excision tissues and normal tissues. Numbers of molecules in the tables are values of numbers of PERP expressed molecules per 2 ng of polyA(+) RNA, Symbol * in the tables shows that the measured value of PERP expressed molecule numbers was lower than the detection limit. The right end column of the tables shows expression amounts of mRNA of the PERP gene in each tissue when the PERP gene-expression amount in trachea showing the highest expression in normal tissues was defined as 1.

It is apparent that the PERP gene shows low expression in human normal tissues and, as compared with trachea showing the highest expression in human normal tissue, its expression is enhanced 3 times or more in tumor mass derived from ASPC-1 cell line which is a pancreatic cancer cell line and from xenograft to which ASPC-1 cell line is transplanted, tumor mass derived from xenograft to which 2 different pancreatic cancer tumor tissue-derived cells (PC02 and PC03) are transplanted, colo 205 cell line which is a colorectal cancer cell line, clear cell cancer of kidney and esophageal squamous cancer.

Example 2

Analysis for Expressing the PERP Gene in Excised Samples from Cancer Operation

Amounts of mRNA of the PERP gene in excised samples from cancer operation were quantitatively determined by Light Cycler (manufactured by Roche Diagnostic) using Light Cycler-Fast Start DNA Master SYBR Green I kit (manufactured by Roche Diagnostic).

Each polyA(+) RNA extracted and purified by a method described in (2) of Example 1 from a cancerous part of tumor tissues excised from 6 cases of colorectal cancer (5 primary plexus cases and 3 metastatic plexus cases) and 16 cases of pancreas cancer and an adjacent non-cancerous part was used as a template and cDNA was prepared by a method described in (3) of Example 1. The cDNA solution (1 µL) (an amount corresponding to 50 ng as total RNA), each of 0.5 µL of a forward primer containing the sequence represented by SEQ ID NO:5 and a reverse primer containing the sequence represented by SEQ ID NO:6 (both manufactured by Proligo, 5 µmol/L), 1.2 µL, 0.9 µL or 0.675 µL of 25 mmol/L magnesium chloride solution and 1 µL of Light Cycler-Fast Start DNA Master SYBR Green I (heat-resisting DNA polymerase and SYBR Green I) were added to sterile deionized water to give a total amount of 10 µL. After heating at 95° C. for 10 minutes, PCR was carried out by 45 cycles, one cycle consisting of reaction at 94° C. for 10 seconds, reaction at 65° C. or 60° C. for 30 seconds and reaction at 72° C. for 20 seconds, by using Light Cycler (manufactured by Roche Diagnostic). After keeping it at 65° C. for 15 seconds, the reaction in which temperature was raised up to 95° C. at the rate of 0.1° C. per second was carried out to analyze a melting curve of the product. After completion of the reaction, data were analyzed using the software attached to the instrument at the above-described three magnesium chloride concentrations and at two annealing temperatures.

Plasmid PLACE 1001407 (GenBank Accession No. AK 075082) encoding cDNA prepared in (3) of Example 1 and cDNA of the PERP gene purified by a Qiagen Plasmid Prep Midi Kit (manufactured by Qiagen) as a sample for the preparation of a calibration curve in $10^8$, $10^6$, $10^4$ and $10^2$ copies per reaction and sterile deionized water as a negative control were arranged and, under the above-described conditions, PCR was carried out using Light Cycler (manufactured by Roche Diagnostic).

Expression amounts of mRNA of the PERP gene in cancerous part in 8 pairs pairs of primary plexuses and 3 pairs of metastasized plexuses) of 6 cases of colorectal cancer clinical samples and in 16 pairs in 16 pancreatic cancer clinical samples and adjacent non-cancerous part were shown in Table 3.

table shows the ratio of the PERP gene-expression amount in the cancerous part to that in the adjacent non-cancerous part.

In 80% of the primary focus of colorectal cancer (in 4 cases out of the 5 cases; C1 appendix, C2 rectum, C4 rectum and C5 ascending colon), 33% of the metastatic focus of colorectal cancer (in 1 case out of the 3 cases; C6 metastasis to liver) and in 9 cases in the 16 cases of the pancreatic cancer of clinical samples P1, P2, P3, P5, P8, P9, P11, P12, P14), it is now

| Cancer types | Sample numbers | | Tissues | Number of molecules | Cancerous part/ Non-cancerous part |
|---|---|---|---|---|---|
| Colorectal cancer | C1 | Appendix | Cancerous part | 172,300 | 4,997,100 |
| | | | Non-cancerous part | 0.0* | |
| | C2 | Rectum | Cancerous part | 4,357 | 871 |
| | | | Non-cancerous part | 5.0* | |
| | | Hepatic metastasis | Cancerous part | 9,427 | 1 |
| | | | Non-cancerous part | 6,428 | |
| | C3 | Hepatic metastasis | Cancerous part | 8,585 | 0 |
| | | | Non-cancerous part | 30,100 | |
| | C4 | Rectum | Cancerous part | 7,772 | 316 |
| | | | Non-cancerous part | 24.6* | |
| | C5 | Ascending colon | Cancerous part | 4,552 | 22 |
| | | | Non-cancerous Part | 211 | |
| | C6 | Ascending colon | Cancerous part | 3,053 | 65 |
| | | | Non-cancerous Part | 46.9* | |
| | | Hepatic metastasis | Cancerous part | 4,239 | 0 |
| | | | Non-cancerous part | 120,000 | |
| Pancreatic cancer | P1 | | Cancerous part | 838,900 | 143 |
| | | | Non-cancerous part | 5,887 | |
| | P2 | | Cancerous part | 493,000 | 7 |
| | | | Non-cancerous part | 74,100 | |
| | P3 | | Cancerous part | 301,300 | 6 |
| | | | Non-cancerous part | 52,210 | |
| | P4 | | Cancerous part | 215,000 | 0 |
| | | | Non-cancerous part | 551,000 | |
| | P5 | | Cancerous part | 184,000 | 16,577 |
| | | | Non-cancerous part | 11.1* | |
| | P6 | | Cancerous part | 126,300 | 1 |
| | | | Non-cancerous part | 223,700 | |
| | P7 | | Cancerous part | 125,200 | 1 |
| | | | Non-cancerous part | 126,600 | |
| | P8 | | Cancerous part | 65,300 | 8 |
| | | | Non-cancerous part | 7,760 | |
| | P9 | | Cancerous part | 55,380 | 48 |
| | | | Non-cancerous part | 1,145 | |
| | P10 | | Cancerous part | 41,950 | 1 |
| | | | Non-cancerous part | 55,260 | |
| | P11 | | Cancerous part | 37,800 | 6 |
| | | | Non-cancerous part | 5,930 | |
| | P12 | | Cancerous part | 30,890 | 46 |
| | | | Non-cancerous part | 666 | |
| | P13 | | Cancerous part | 28,700 | 2 |
| | | | Non-cancerous part | 15,110 | |
| | P14 | | Cancerous part | 14,180 | 4 |
| | | | Non-cancerous part | 3,953 | |
| | P15 | | Cancerous part | 4,993 | 1 |
| | | | Non-cancerous part | 7,719 | |
| | P16 | | Cancerous part | 900 | 1 |
| | | | Non-cancerous part | 1,555 | |

Table 3 shows expression amounts of mRNA of the PERP gene in the cancerous part and the adjacent non-cancerous part in excised samples in operation of patients suffering from colorectal cancer and pancreatic cancer. The column for number of molecules in the table shows the number of PERP-expressing molecules in 50 ng of total RNA derived from the cancerous part in the excised sample in operation and number of PERP-expressing molecules in 50 ng of total PNA derived from the adjacent non-cancerous part in the same sample. Symbol * in the table shows that the measured value of the PERP-expressing molecules was lower than the detection limit. The column of cancerous part/non-cancerous part in the apparent that the expression of the PERP gene was enhanced 3-fold or more in the cancerous part, as compared with the non-cancerous part.

Example 3

Analysis of Expression of the PERP Gene Using Cancer Profiling Array (Clontech)

Expression of the PERP gene in various cancer tissues and normal tissues adjacent thereto was analyzed using a Cancer Profiling Array (manufactured by Clontech, Cat. 7841-1, Lot 2070686; various cancer tissues and as a control, a Nylon membrane to which cDNA obtained from the adjacent tissues was dot-blotted) as follows.

A probe of the PERP gene was prepared in accordance with the manufacture's instructions of DIG High Prime DNA Labeling Kit (Roche Diagnostics) as follows. Plasmid pcPERP n–1 (1 µg) for expression of PERP described in (1) of Example 4 was cleaved with EcoRI and HindIII and separated by agarose electrophoresis and the resulting fragment in a size of 0.6 kbp was cut out and purified with Gene Clean Spin Kit (manufactured by BIO 101) to give 15 µL of a DNA solution. To 10 µL of the resulting solution was added 6 µL of sterile water, followed by heating at 95° C. for 10 minutes and quickly cooled in ice, 4 µL of DIG-High Prime was added thereto, followed by reaction at 37° C. for 20 hours. To this was added 2 µL of 0.2 mol/L EDTA, and the reaction was stopped by heating at 65° C. for 10 minutes. The yield was tested by a usual method and 22 µL of probe of 0.24 ng/µL was prepared.

Hybridization and detection were carried out in accordance with the manufacture's instructions as follows. Thus, 1.5 mg of sheared salmon testis DNA (hereinafter referred to as "stDNA") was heated at 95° C. for 5 minutes, quickly cooled in ice and added to 15 mL of Express Hyb Hybridization Solution (manufactured by Clontech) which was previously heated at 68° C. to prepare a hybridization solution A. The above-described Cancer Profiling Array was immersed in distilled water, water was completely drained and placed in a plastic bag, 10 mL of a hybridization solution A was added and the mixture was kept at 68° C. for 30 minutes to carry out pre-hybridization. To 5 ng of the probe was added 150 µg of stDNA, followed by heating at 95° C. for 5 minutes and quickly cooled in ice, and added to 5 mL of a hybridization solution A to prepare a probe solution. The Cancer Profiling Array in which the pre-hybridization was finished was transferred to a new plastic bag and a probe solution was added thereto, followed by reaction at 68° C. for 16 hours. Then, the Cancer Profiling Array was repeatedly washed 4 times with 200 mL of a washing solution 1 (2×SSC, 0.5% SDS) at 68° C. for 30 minutes, then washed once with 200 mL of a washing solution 2 (0.2×SSC, 0.5% SDS) at 68° C. for 30 minutes and finally washed with 200 mL of 2×SSC at room temperature for 5 minutes. The following detection reaction was carried out at room temperature. The washed Cancer Profiling Array was washed with 100 mL of washing solution 3 (0.1 mol/L maleate buffer of pH 7.5 containing 0.3% Tween 20 and 0.15 mol/L sodium chloride) for 2 minutes and was blocked with 10 mL of a blocking solution (0.1 mol/L maleate buffer of pH 7.5 containing 1-fold concentration of a blocking reagent and 0.15 mol/L sodium chloride) for 30 minutes. Then, reaction was carried out for 30 minutes with an antibody solution in which 1 µL of anti-DIG alkaline phosphatase conjugated antibody was added to 5 mL of the blocking solution. The reaction product was repeatedly washed twice with 100 mL of a washing solution 3 for 15 minutes, equilibrated with 20 mL of a detection solution (0.1 mol/L Tris hydrochloride buffer of pH 9.5 containing 0.1 mol/L of sodium chloride) and immersed for 5 minutes in a detection solution to which 25 µL of CDP-Star was added. After the detection solution was removed, detection with an X-ray film was carried out.

FIG. 1 shows expression of mRNA of the PERP gene in cancer tissues (shown by T in the drawing) in various cases of breast cancer, uterus cancer, colorectal cancer, stomach cancer, ovary cancer, lung cancer and thyroidal gland cancer and the adjacent non-cancerous part (shown by N in the drawing). In many cases, enhancement of expression of PERP was recognized in the cancerous part as compared with the adjacent normal tissues.

Example 4

Preparation of the Anti-PERP Gene Product Monoclonal Antibody (1) Preparation of PERP Expression Cells A solution containing 1 µL of a human PERP gene-containing plasmid HEMBA 1006335 (GenBank Accession No. AK 074585, 1 ng/µL), 2 µL of 10× ExTaq buffer, 2 µL of 2 mmol/L dNTP, each of 2 µL of 10 µmol/L of primers consisting of nucleotide sequences represented by SEQ ID NO:7 and SEQ ID NO: 8, 0.5 µL of ExTaq polymerase (manufactured by Takara Shuzo) and 10.5 µL of sterile water was heated at 94° C. for 5 minutes and reaction was carried out by 25 cycles, one cycle consisting of reaction at 94° C. for 30 seconds, reaction at 65° C. for 30 seconds and reaction at 72° C. for 1 minute, followed by reaction at 72° C. for 7 minutes. The reaction product was separated by agarose gel electrophoresis and an amplified fragment of about 0.6 kb was extracted with Geneclean Spin Kit (manufactured by BIO 101). The fragment was ligated with pCRII-TOPO vector using TOPO TA cloning kit (manufactured by Invitrogen) and *Escherichia coli* DH5α was transformed by a method of Cohen, et al. [*Proc. Natl. Acad. Sci., USA*, 69, 2110 (1972)]. A plasmid was extracted from the resulting transformant using a plasmid extraction kit (manufactured by Qiagen) to obtain plasmid pCRII-PERP containing the human PERP gene.

As a cloning vector to add myc-His tag sequence to the 3'-terminal of the PERP fragment, pBSmH was prepared as follows.

pcDNA 3.1(–)/myc-His C (manufactured by Invitrogen) was digested with PmeI and, by the same method as above, a DNA fragment containing a gene encoding myc-His tag of about 170 bp was obtained. The fragment was ligated using a DNA ligation kit ver. 2 (manufactured by Takara Shuzo) to pBluescript II SK (–) (manufactured by Stratagene) in which its terminal was blunted with T4 DNA polymerase (manufactured by Takara Shuzo) after digesting with XbaI and KpnI, and then *Escherichia coli* DH5α was transformed. A plasmid was extracted from the resulting transformant with a plasmid extracting kit (manufactured by Qiagen) to prepare plasmid pBSmH. The pBSmH plasmid was digested with a restriction enzyme XbaI to give two fragments of about 2.9 kbp and about 160 kbp.

The above pCRII-PERP was digested with EcoRI and XbaI to obtain a fragment containing the PERP gene. The fragment was ligated by a DNA ligation kit ver. 2 (manufactured by Takara Shuzo) to pBSmH digested with EcoRI and XbaI and then *Escherichia coli* DH5α was transformed. A plasmid was extracted from the resulting transformant with a plasmid extracting kit (manufactured by Qiagen) to obtain plasmid pBS-PERPmH.

pBS-PERPmH was digested with EcoRI and HindIII to prepare a fragment containing a gene encoding the PERP gene and myc-His tag. The fragment was ligated by a DNA ligation kit ver. 2 (manufactured by Takara Shuzo) to pcDNA 3.1+(manufactured by Invitrogen) digested with EcoRI and HindIII and then *Escherichia coli* DH5α was transformed. A plasmid was extracted from the resulting transformant with a plasmid extracting kit (manufactured by Qiagen) to give plasmid pcPERPmH which was an expression plasmid of human PERP.

The pcPERPmH was introduced into CHO/DG44 cells [*Somatic Cell and Molecular Genetics*, 12(6), 555 (1986)] according to an electroporation method [*Cytotechnology*, 3, 133 (1990)] as follows.

The cells which were cultured in an IMDM medium (manufactured by Life Technology) to which 10% fetal bovine serum (manufactured by Life Technology), 1×HT supplement (manufactured by Life Technology) and 1% penicillin-streptomycin (manufactured by Life Technology) were added (hereinafter referred to as "A3 medium") were used. The CHO/DE44 cells were suspended in a K-PBS buffer (137 mmol/L potassium chloride, 2.7 mmol/L sodium chloride, 8.1 mmol/L disodium monohydrogen phosphate, 1.5 mmol/L monosodium dihydrogen phosphate and 4 mmol/L magnesium chloride buffer) to obtain a concentration of $8\times10^6$ cells/mL and the cell suspension was mixed with 4 µg of the above-described expression plasmid pcPERPmH. The mixed solution was transferred to a cuvette (distance between electrodes: 2 mm) and gene introduction was carried out using a Gene Pulser II apparatus (manufactured by Biorad) under such conditions that the pulse voltage was 0.35 kV and the electric capacity was 250 µF. The cuvette was allowed to stand on ice and then the cell suspension in the cuvette was suspended in A3 medium and cultured at 37° C. in a 5% $CO_2$ incubator. After the culturing for one day, the medium was exchanged to A3 medium to which 0.5 mg/mL of G418 (manufactured by Carbiochem) was added, followed by culturing. During the culturing, dilution was carried out and subculture was continued and, after about two weeks from introduction of the gene, a transformant cell line having resistance to G418 was prepared.

The resulting transformant cells were diluted with A3 medium to which 0.5 mg/mL of G418 was added to give a cell density of 1.25 cells/mL, 200 µL, thereof was placed in each of a 96-well plate and cloning by a limiting dilution method was carried out.

The resulting transformant cells (1 to $5\times10^5$ cells) were dissolved in 15 µL of 1×PAGE buffer, heated at 95° C. for 5 minutes, fractionated by SDS-polyacrylamide electrophoresis [*Antibodies—A Laboratory Manual* (Cold Spring Harbor Laboratory, 1988)] and blotted to a PVDF membrane. After blocking with BSA-PBS, reaction with anti-myc monoclonal antibody 9E10 (manufactured by MBL) was carried out at room temperature for 1 hour. After washing with Tween-PBS, reaction with a peroxidase-labeled anti-mouse immunoglobulin antibody (manufactured by Dako) as the second antibody was carried out at room temperature for 1 hour. After sufficiently washing it with Tween-PBS, detection was carried out using an ECL-detection kit (manufactured by Amersham), followed by photosensitizing on an X-ray film.

Figure 2:
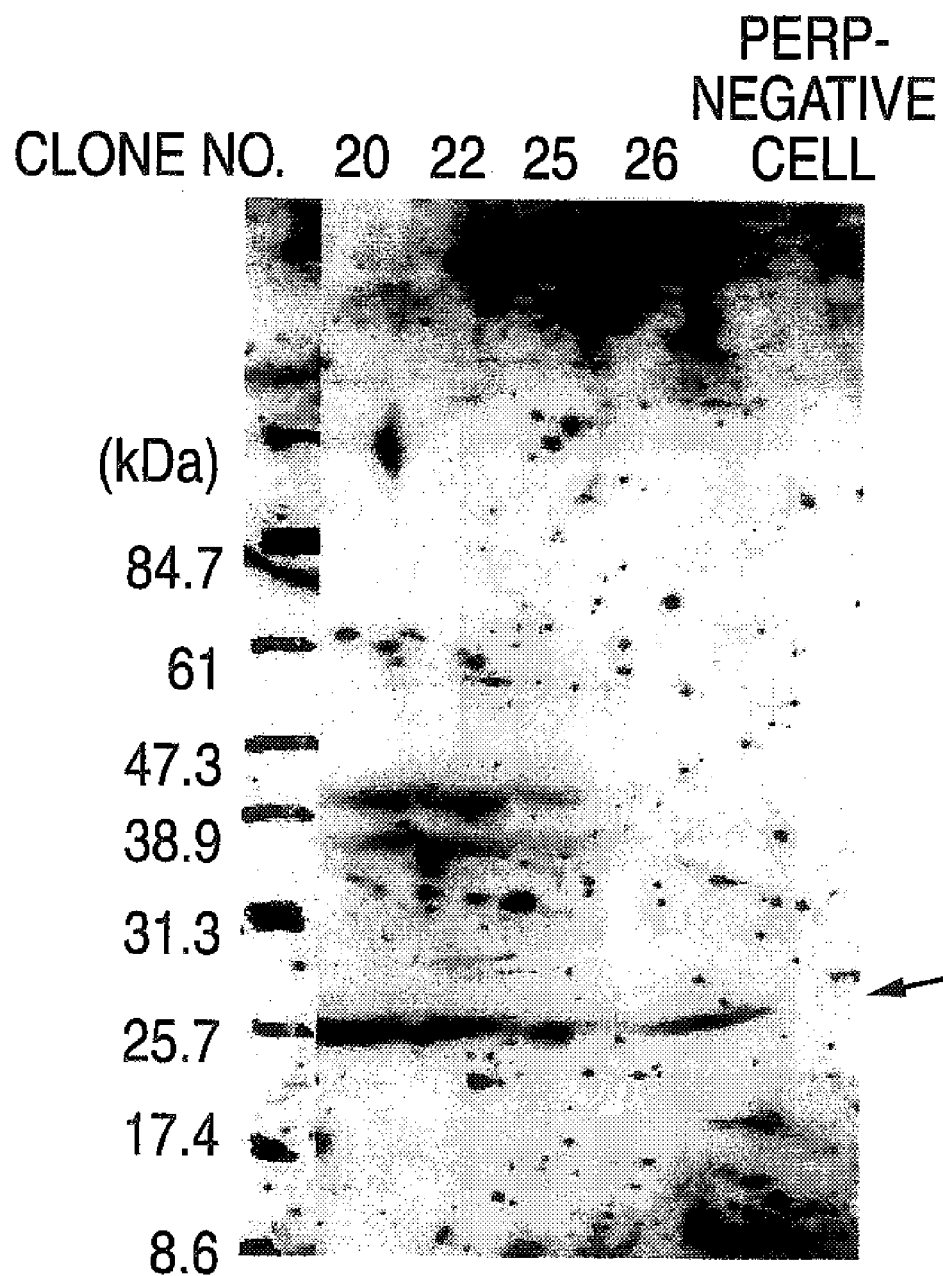
FIG. 2 shows the result of PERP expression for each clone of cells into which the PERP gene is introduced by Western blotting using an anti-Myc antibody. Clone numbers in the drawing show each clone of 4 kinds of PERP/CHO cells. PERP negative cell shows CHO/DG44 cell into which no gene is introduced. The arrow in the drawing shows about 25 kDa which is a molecular weight of a polypeptide chain encoded by the PERP gene.

The result is shown in FIG. 2. A cell line in which a signal was recognized around the molecular weight of 25 kDa was designated as a PERP-expressing cell line (hereinafter referred to as "PERP/CHO cell").

(2) Preparation of Anti-PERP Monoclonal Antibody-1
(2)-1 Preparation of Immunogen The PERP/CHO cells prepared in the above (1) were cultured on an Iscove's modified Dulbecco's medium (manufactured by Invitrogen) containing 10% fetal bovine serum for 2 to 3 days and suspended in PBS to give cell numbers per animal of $6\times10^6$ to $1\times10^7$ cells.

(2)-2 Immunization of Animals and Preparation of Antibody-Producing Cells

The cells prepared in (2)-1 were administered to 3 female SD rats of 6 weeks old together with $1\times10^9$ cell of pertussis vaccine (manufactured by Serum Laboratory, Chiba Prefecture) After one week from the administration, it was administered once a week 5 times in total. Blood was partially collected from the fundus of the eye of the rat, an antibody titer in blood was measured by sandwich ELISA as shown below and, from the mouse showing a sufficient antibody titer, spleen was excised after 3 days from the final immunization.

The spleen was finely cut in MEM (minimum essential medium) medium (manufactured by Nissui Pharmaceutical), loosened by tweezers and centrifuged (250×g for 5 minutes). A Tris-ammonium chloride buffer (pH 7.6) was added to the resulting precipitate fraction and reaction was carried out for 1 to 2 minutes to remove erythrocytes. The resulting precipitate fraction (cell fraction) was washed 3 times with MEM medium and used for cell fusion,
(2)-3 Enzymatic Immunoassay (Sandwich ELISA)

In a 96-well plate for EIA (manufactured by Gliner), anti-c-Myc antibody produced by MYC 1-9E 10.2 cell line (ATCC CRL-1729) was prepared to obtain a concentration of 10 µg/mL using a Dulbecco's PBS, the solution was dispensed at 50 µL/well and allowed to stand at 4° C. overnight for adsorption. The plate was washed with PBS, BSA-PBS was added at 100 µL/well, and the plate was allowed to stand at room temperature overnight so that the remaining active groups were blocked to prepare a reaction plate.

To $5\times10^7$ cells of PERP/CHO cells or CHO/DG44 cells was added 1 ml of a buffer for dissolving the cells (50 mmol/L Tris-hydrochloride buffer of pH 7.2 containing 1% Triton X, 150 mmol/L sodium chloride, 2 mmol/L magnesium chloride, 2 mmol/L calcium chloride, 0.1% azide, 50 mmol/L iodoacetamide, 50 mmol/L N-ethylmaleimide, 1 mg/ml leupeptin and 0.1 mmol/L DTT), the mixture was allowed to stand at 4° C. for 2 hours and centrifuged, the resulting supernatant was dispensed at an amount of 50 µL/well on a reaction plate wherefrom BSA-PBS was removed, and the plate was allowed to stand at room temperature for 2 hours. The plate was washed with PBS and a culture supernatant of hybridoma cells or immunized rat antiserum was dispensed at 50 µL/well, and the plate was allowed to stand at room temperature for 2 hours. After the plate was washed with Tween-PBS, peroxidase-labeled goat anti-rat immunoglobulin (manufactured by Caltag) as a secondary antibody was dispensed at 50 µL/well and the plate was allowed to stand at room temperature for 1 hour. After the plate was washed with Tween-PBS, an ABTS substrate solution [a solution prepared by dissolving 0.55 g of 2,2'-azino-bis(3-ethylbenzothiazoline-6-sulfonic acid) ammonium in 1 L of 0.1 mol/L citrate buffer (pH 4.2) and, immediately before use, an aqueous hydrogen peroxide solution was added thereto at 1 µL/mL] was dispensed at 50 µL/well to colorize and absorption of 415 nm (hereinafter referred to as "OD415" or the like) was measured using a plate reader (Emax; manufactured by Molecular Device).
(2)-4 Preparation of Mouse Myeloma 8-Azaguanine-resisting mouse myeloma cell line P3X63Ag8U.1:P3-U1 [ATCC CRL-1597. *European Journal of Immunology*, 6, 511 (1976)] was cultured on a normal medium (RPM medium to which 10% fetal bovine serum was added) so that $2\times10^7$ cells or more were ensured upon cell fusion and used for the cell fusion.
(2)-5 Preparation of Hybridoma The rat spleen cells prepared in above (2)-2 and the myeloma cells prepared in above (2)-4 were mixed at a ratio of 10:1 and centrifuged (250×g for 5 minutes), the supernatant was discarded, the precipitated cell group was well loosened, a mixture of 2 g of polyethylene glycol 1000 (PEG 1000), 2 mL of MEM medium and 0.7 mL of dimethyl sulfoxide was added thereto at 0.2 to 1 L/$10^8$ mouse spleen cells and at 37° C. under stirring, 1 to 2 ml of MEM medium was added thereto every 1 to 2 minutes several times and then MEM medium was added to give a total amount of 50 mL. After centrifugation (900 rpm for 5 minutes), the supernatant was discarded, the cells were slowly loosened and the cells were suspended in 100 mL of HAT medium by suction and sucking out using a measuring pipette.

The suspension was dispensed into a 96-well culture plate at 100 µL/well and cultured in a 5% $CO_2$ incubator at 37° C. for 10 to 14 days. After the culturing, the culture supernatant was examined by sandwich ELISA described in (2)-3, wells which reacted with PERP/CHO cells but did not react with CHO/DG44 cells were selected and the cells contained therein were subjected to cloning by a limiting dilution method twice to give an anti-PERP antibody-producing hybridoma KM 3314.

Figure 3:
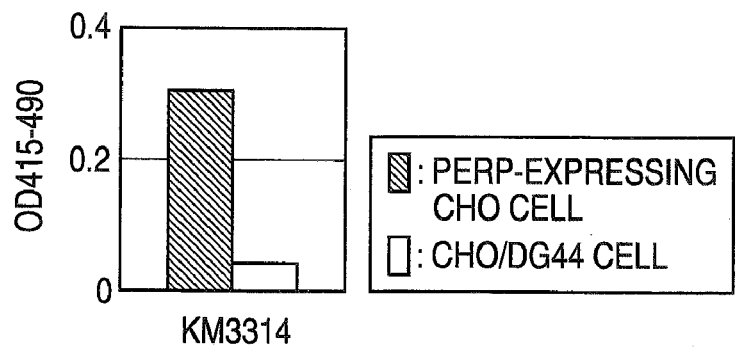
FIG. 3 shows the reactivity of KM 3314 in sandwich ELISA. Black bar in the left shows the result of ELISA using a cell lysate of PERP/CHO cell and white bar in the right shows that of CHO/DG44 cell.

FIG. 3 shows reactivity of KM 3314 to PERP/CHO cells and to CHO/DG44 cells by sandwich ELISA described in (2)-3. KM 3314 specifically reacted with PERP/CHO cells.

(2)-6 Purification of Monoclonal Antibody

The hybridoma prepared in (2)-5 was intraperitoneally injected to pristane-treated female nude mice 8 weeks old (BALB/c) at 5 to $20×10^6$ cells/mouse. After 10 to 21 days, ascites were collected (1 to 8 mL/mouse) from the mice in which the hybridoma became ascites cancer to produce ascites.

The ascites was centrifuged (1,200×g for 5 minutes) to remove the solid. Pure IgG monoclonal antibody was prepared by purification using a caprylic acid precipitation method [*Antibodies—A Laboratory Manual*, Cold Spring Harbor Laboratory (1988)]. When a subclass of the purified anti-PERP mouse antibody KM 3314 was decided by ELISA using a subclass typing kit, the subclass of the anti-PERP mouse antibody 3314 was IgG2a.

(2)-7 Investigation of Reactivity of Monoclonal Antibody—Western Blotting

A sample buffer for SDS-PAGE [62 mmol/L Tris hydrochloride buffer (pH 6.8) containing 2% SDS and 10% glycerol] was added to each of PERP/CHO cells and CHO/DG44 cells, colorectal cancer cell line Colo 205 (ATCC CCL-222) and lung cancer cell line PC1 (Immunobiological Laboratory) at 100 µL per $1×10^7$ Cells, followed by heating at 100° C. and ultrasonic disruption to prepare a soluble fraction. The amount corresponding to $1×10^5$ cells each was subjected to SDS-PAGE and the gel after the electrophoresis was blotted to a PVDF membrane. After the membrane was blocked by BSA-PBS, it was allowed to react at room temperature for 2 hours with BSA-PBS containing 5 µg/mL of each of culture supernatant of hybridoma KM 3314 and negative control antibody KM 1762 (anti-avermectin antibody).

After the reaction, the membrane was washed with Tween-PBS and reaction with peroxidase-labeled rabbit anti-rat immunoglobulin (manufactured by Dako) was carried out at room temperature for 1 hour. After the reaction, the membrane was washed with Tween-PBS and the band to which the anti-PERP antibody was bound was detected using ECL™ Western Blotting Detection Reagents (manufactured by Amersham-Pharmacia).

Figure 4:
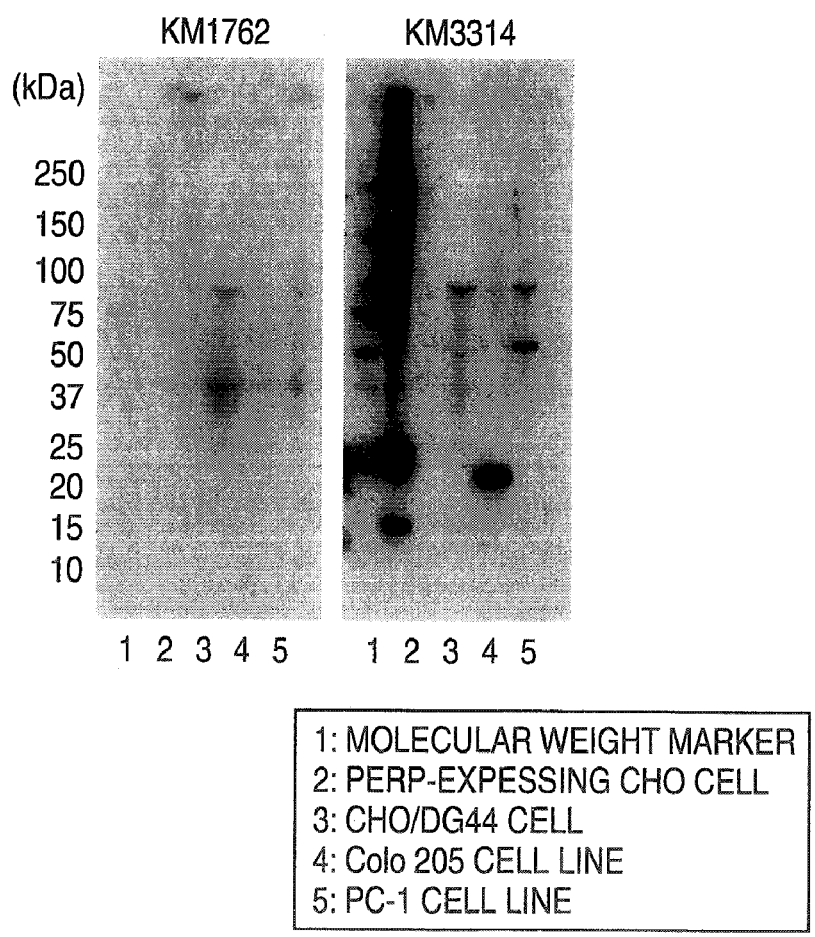
FIG. 4 shows the reactivity of KM 3314 in Western blotting. The lane from the left shows a molecular weight marker and lysates of PERP/CHO cell, CHO/DG44 cell, Colo 205 cell line and PC-1 cell line. The picture on the left shows the result in which KM1764 which is a negative control was used as the primary antibody, and the picture on the right shows the result in which KM3411 was used as the primary antibody.

The result is shown in FIG. 4. A band was detected near 25 kDa in PERP/CHO cells and colorectal cancer cell line Colo 205. Therefore, the anti-PERP mouse antibody KM 3314 was found to be an antibody which can detect by PERP using Western blotting. The molecular weight of the band detected in the PERP/CHO cells was more than that of the band detected in the colorectal cancer cell line Colo 205 might be because expression was carried out together with myc-His tag sequence in the PERP/CHO cells.

(3) Preparation of Anti-PERP Monoclonal Antibody-2

(3)-1 Preparation of Immunogen

The PERP-expressing cell line prepared in the above (1) was cultured on an Iscove's Modified Dulbecco's medium containing 10% fetal bovine serum (manufactured by Invitrogen) for 2 to 3 days and suspended in PBS to obtain cell numbers per mouse of $6×10^6$ to $1×10^7$ cells.

(3)-2 Immunization of the Animals and Preparation of Antibody-Producing Cells

The cells prepared in above (3)-1 were administered to 3 female Balb/c mice 6 weeks old together with $1×10^9$ cells of pertussis vaccine (manufactured by Serum Laboratory in Chiba Prefecture). After one week from the administration, administrations were carried out once a week 5 times in total, Blood was partially collected from the fundus of eye of the mice, an antibody titer thereof in the blood was measured by an immunofluorescent staining method using the following cells by FMAT 8100 HTS system (manufactured by Applied Biosystem) and a flow cytometer (manufactured by Beckman Coulter) and, after 3 days from the final immunization, spleens were excised from the mice in which a sufficient antibody titer was obtained.

The spleen was finely cut in MM (minimum essential medium) medium (manufactured by Nissui Pharmaceutical), loosened by tweezers and centrifuged (250×g for 5 minutes). To the resulting precipitation fraction was added a Tris-ammonium hydrochloride buffer (pH 7.6) and reaction was carried out for 1 to 2 minutes to remove erythrocytes. The resulting precipitate fraction (cell fraction) was washed 3 times with MEM and used for cell fusion.

(3)-3 Fluorescent Antibody Staining Method Using Cells (FMAT: Fluorometric Microvolume Assay Technology)

With regard to the cells for the assay, PERP/CHO cells and CHO/DG44 cells prepared in (1) were used. The cells which were cultured on an Iscove's Modified Dulbecco's medium containing 10% fetal bovine serum (manufactured by Invitrogen) for 2 to 3 days and peeled off with a Tripsin-EDTA solution (manufactured by Invitrogen) were suspended on the same medium, seeded onto a black 96-well plates for FMAT at $7×10^3$ cells/100 µL medium/well and cultured overnight. Mouse anti-serum to be immunized or cultured supernatant of hybridoma cells was dispensed into the plate at 5 µL/well as a primary antibody, and ALEXA 647-labeled anti-mouse immunoglobulin G (H+L) (manufactured by Molecular Probe) was dispensed at 50 µL/well as a secondary antibody, and the plate was allowed to stand for 4 hours under shading the light. Wavelength of 650 to 685 nm excited by laser beam of 633 nm He/Ne was measured by an FMAT 8100 HTS system (manufactured by Applied Biosystem).

(3)-4 Fluorescent Antibody Staining Method Using Cells Flow Cytometry)

As the cells for the assay, PERP/CHO cells and CHO/DG44 cells prepared in (1) were used. Cells which were cultured on an Iscove's Modified Dulbecco's medium containing 10% fetal bovine serum (manufactured by Invitrogen) for 2 to 3 days and peeled off with a 0.02% EDTA solution (manufactured by Nacalai Tesque) were washed with PBS and, in order to avoid the non-specific adsorption of antibody, they were blocked for 20 minutes at ice temperature using BSA-PBS. They were dispensed into a 96-well U-shaped plate so as to give a density of $1×10^6$ cells/100 µL/BSA-PBS, followed by centrifugation (1,800 rpm for 2 minutes), then supernatant was removed and mouse anti-serum to be immunized or cultured supernatant of hybridoma cells was dispensed at 50 µL/well as a primary antibody, followed by reaction at ice temperature for 30 minutes. Washing was carried out 3 times by a centrifugation method using PBS and ALEXA 488-labeled anti-mouse immunoglobulin G (H+L) (manufactured by Molecular Probe) was dispensed at 20 μL/well as a secondary antibody, followed by reaction at ice temperature for 30 minutes under shading the light. Washing with PBS was carried out once again, followed by suspension in PBS, and wavelength of 510 to 530 nm excited with laser beam of 488 nm Ar was measured by a flow cytometer (manufactured by Beckman Coulter).

(3)-5 Preparation of Mouse Myeloma Cells

8-Azaguanine-resistant mouse myeloma cell line P3X63Ag8U.1:P3-U1 [ATCC CRL-1597: *European Journal of Immunology*, 6, 511 (1976)] was cultured on a normal medium (RPMI medium to which 10% fetal bovine serum was added) and $2 \times 10^7$ cells or more were ensured upon cell fusion and used for cell fusion.

(3)-6 Preparation of Hybridoma

The mouse splenic cells obtained in (3)-2 and the myeloma cells obtained in (3)-5 were mixed to give a ratio of 10:1 and centrifuged (250×g for 5 minutes), the supernatant was discarded, the precipitated cells were well loosened, then a mixed solution of 2 g of polyethylene glycol 1000 (PEG-1000), 2 ml of MEM medium and 0.7 mL of dimethyl sulfoxide were added thereto at 0.2 to 1 mL/$10^8$ mouse spleen cells under stirring at 37° C., 1 to 2 mL of MEM medium was added thereto several times every 1 to 2 minutes and MEM medium was added to give a total volume of 50 inn. After centrifugation (900 rpm for 5 minutes), the supernatant was discarded and the cells were gently loosened and gently suspended in 100 mL of an HAT medium by suction and sucking out using a measuring pipette.

The suspension was added to a 96-well culture plate at 200 μL/well and cultured in a 5% $CO_2$ incubator at 37° C. for 10 to 14 days. After the culturing, the culture supernatant was examined by the immunofluorescent staining methods described in (3)-3 and (3)-4, wells which reacted with PERP/CHO cells and did not react with CHO/DG44 cells were selected, cloning was repeated twice by a limiting dilution method from the cells contained therein and an anti-PERP antibody-producing hybridoma KM3411 (FERM BP-8643) was established.

FIG. 5 shows reactivity of monoclonal antibody contained in the culture supernatant of hybridoma KM3411 to PERP/CHO cells and CHO/D44 cells by an FMAT method. The monoclonal antibody KM3411 produced by the hybridoma KM3411 specifically reacts only with the PERP/CHO cells.

(3)-7 Purification of Monoclonal Antibody

The hybridoma obtained in (2)-5 was intraperitoneally injected at 5 to $20 \times 10^6$ cells/mouse into each of the pristane-treated female nude mice 8 weeks old (BALB/c). After 10 to 21 days, ascites were collected (1 to 8 ml/mouse) from the mice in which ascites were stored as a result of the fact that the hybridoma became ascites cancer.

The ascites were centrifuged (1,200×g for 5 minutes) to remove the solid. Pure IgG monoclonal antibody was prepared by purification using a caprylic acid precipitation method [*Antibodies—A Laboratory Manual*, Cold Spring Harbor Laboratory (1988)]. When a subclass of the purified anti-PERP mouse antibody KM3411 was decided by ELISA using a subclass typing kit, the subclass of the anti-PERP mouse antibody KM3411 was IgG1.

(3)-8 Investigation of Reactivity of Monoclonal Antibody—Fluorescent Cell Staining (Flow Cytometry)

Figure 6:
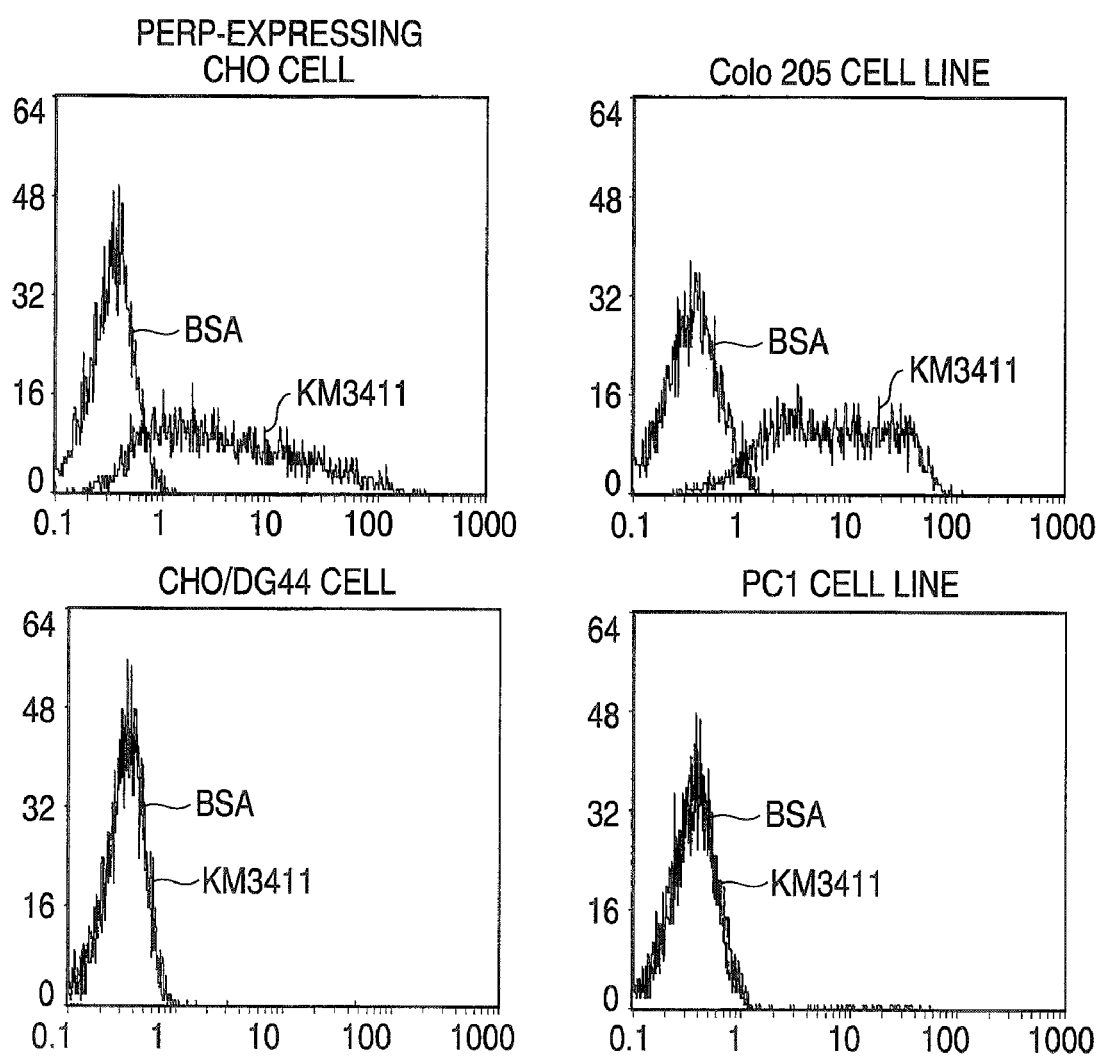
FIG. 6 shows reactivity of KM3411 in flow cytometry. The ordinate and the abscissa in each drawings show cell numbers and fluorescence intensity, respectively.

The experiment was carried out according to the method described in (3)-4. The result is shown in FIG. 6. KM3411 reacted with PERP/CHO cells and colorectal cancer cell line Colo 205 and did not react with CHO/DG44 cells and PC1 in which PERP mRNA was not expressed.

Example 5

Detection of Polypeptide Encoded by the PERP Gene by Immunological Method Using Anti-PERP Mouse Antibody KM3411

(1) Detection of Polypeptide Encoded by the PERP Gene by Immunoprecipitation Reaction Using KM3411

Anti-mouse immunoglobulin (manufactured by Dako) was coated on a 96-well ELISA plate and was allowed to react with culture supernatant of hybridoma cells containing anti-PERP mouse antibody 411 or with culture supernatant of hybridoma cells containing negative control antibody KM511 (anti-granulocyte colony-stimulating factor derivative antibody) at 4° C. overnight. After the reaction, washing was carried out with PBS and, in order to avoid the non-specific adsorption, blocking with USA-PBS was carried out. To $5 \times 10^7$ cells of each of the PERP expressing cells or CHO/DG44 cells was added 1 mL of a buffer for dissolving the cells (50 mmol/L Tris hydrochloride buffer of pH 7.2 containing 1% Triton X, 150 mmol/L sodium chloride, 2 mmol/L magnesium chloride, 2 mmol/L calcium chloride, 0.1% azide, 50 mmol/L iodoacetamide, 50 mmol/L N-ethylmaleimide, 1 mg/mL leupeptin and 0.1 mmol/L DTT), the mixture was allowed to stand at 4° C. for 2 hours and centrifuged and the resulting supernatant was dispensed at 100 μL/well onto the plate from which BSA-PBS was discarded, and the plate was allowed to stand at 4° C. overnight. After washing with Tween-PBS, a sample was prepared by dissolving in a sample buffer for SD S-PAGE 162 mmol/L Tris hydrochloride buffer (pH 6.8) containing 2% of SDS and 10% of glycerol] and the resulting sample was subjected to Western blotting in the same manner as in the above (2)-7. At that time, the anti-PERP mouse antibody KM 3314 prepared in the above (2)-5 and a negative control antibody KM 1762 (anti-avermectin antibody) were used as a primary antibody.

Figure 7:
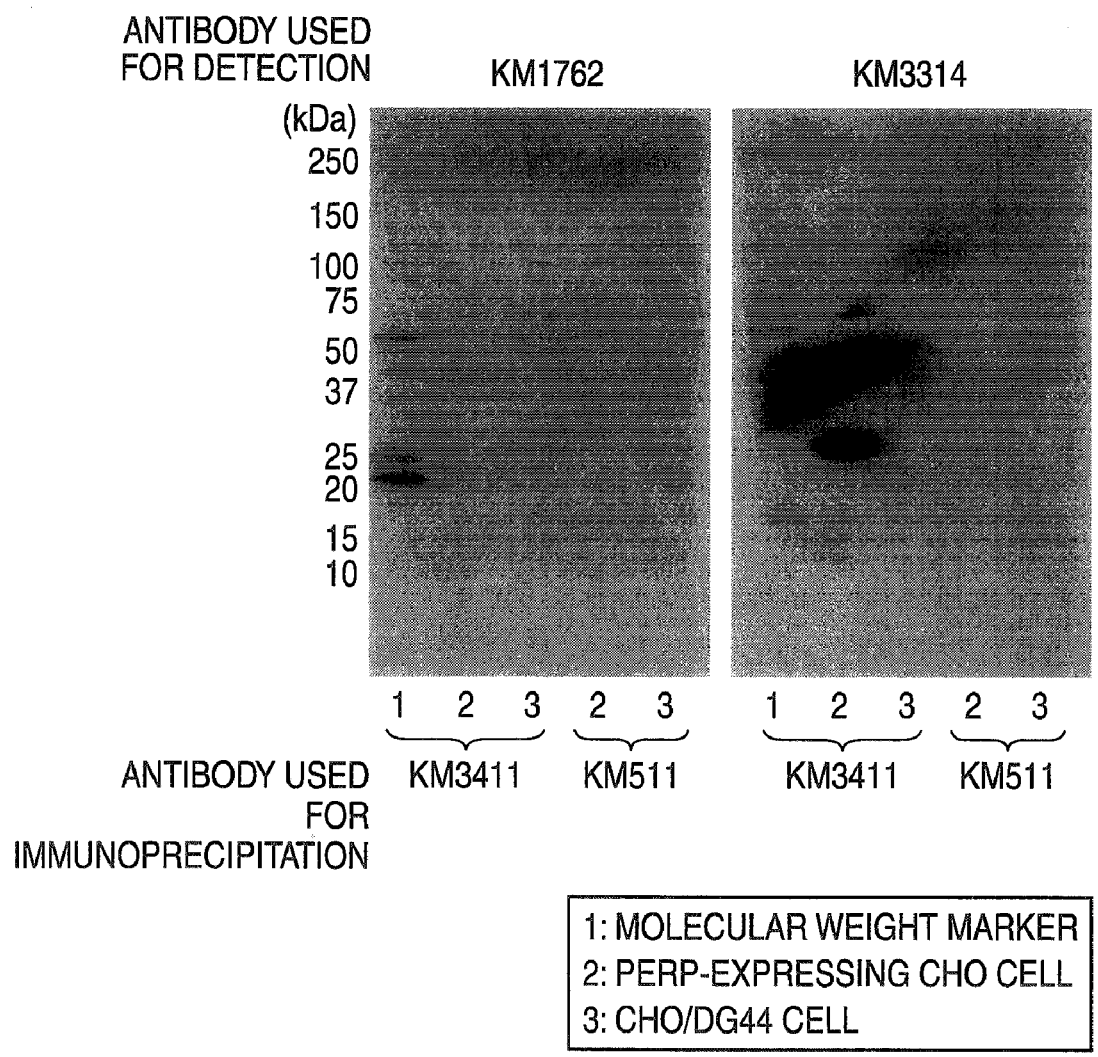
FIG. 7 shows reactivity of KM3411 in immunoprecipitation. KM numbers of the antibody under the bar in the drawing show the antibody used for each immunoprecipitation, and upper numbers on each drawing shows the primary antibody used for the detection. Lanes in each drawing show a marker, PERP/CHO cell and CHO/DG44 cell.

The result is shown in FIG. 7. A band was detected near 25 kDa only in the PERP/CHO cells in which immunoprecipitation was carried out using anti-PERP mouse antibody KM3314, and detection was carried out using anti-PERP mouse antibody KM3411. The anti-PERP mouse antibody KM3411 was found to be an antibody for which detection of PERP by immunoprecipitation reaction is possible.

(2) Detection of PERP by Fluorescent Antibody Staining (Flow Cytometry) Using Anti-PERP Mouse Antibody KM3411

(2)-1 Various Kinds of Cell Lines

Figure 8:
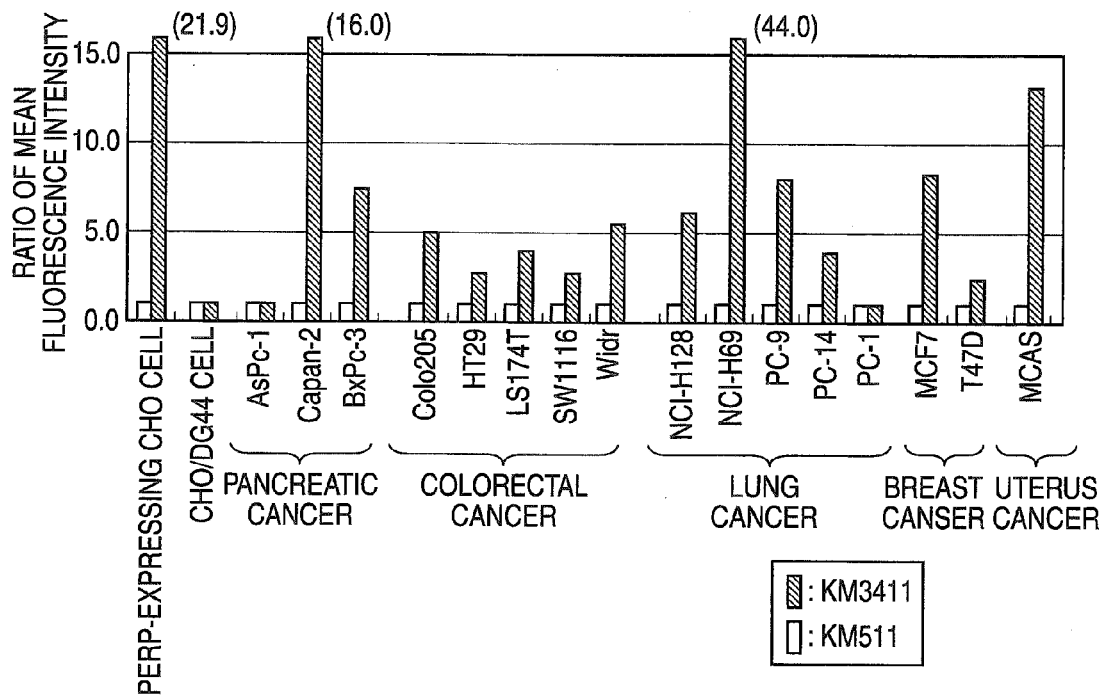
FIG. 8 shows reactivity of KM3411 in flow cytometry. The ordinate shows the ratio of a mean fluorescence intensity of KM3411 when a mean intensity of KM511 which is a negative control is defined as 1. Upper numerals in the graph show the values when ratio of mean fluorescence intensity was 15 or more in particular, Table in the drawing shows the cell lines used.

Various kinds of cancer cell lines shown in FIG. 8 were peeled off with 0.02% EDTA solution (manufactured by Nacalai Tesque), washed with PBS and blocked for 20 minutes at ice temperature using 1% BSA-PBS containing human immunoglobulin (manufactured by Welfide) in order to avoid non-specific antibody adsorption. The mixture was dispensed into a 96-well U-shaped plate to give a density of $1 \times 10^6$ cells/100 μL/BSA-PBS, followed by centrifugation (1,800 rpm for 2 minutes), the supernatant was removed, and culture supernatants of anti-PERP mouse antibody KM 3431 and negative control antibody KM511 (anti-granulocyte colony-stimulating factor derivative antibody) were dispensed at 50 μL/well, followed by reaction at ice temperature for 30 minutes. Washing was carried out 3 times by a centrifugation method using PBS, and ALEXA 488-labeled anti-mouse immunoglobulin G (H+L) (manufactured by Molecular Probe) was added at 20 μL/well as a secondary antibody, followed by reaction at ice temperature under shading from the light for 30 minutes, Again, washing was carried out 3 times by a centrifugation method using PBS, followed by suspension in PBS, and wavelength of 510 to 530 nm excited by laser beam 488 nm Ar was measured by a flow cytometer (manufactured by Beckman Coulter).

The result is shown in FIG. 8. KM3411 reacted with 5 out of 5 cell lines of colorectal cancer, 2 out of 3 cell lines of pancreatic cancer, 4 out of 5 cell lines of lung cancer, 2 out of 2 cell lines of breast cancer and 1 out of 1 cell line of uterus cancer in various cancer cell lines.

(2)-2 Human Peripheral Blood (Monocytes and Granulocytes)

Lymphocytes which were monocytes and monocyte fraction or granulocyte fraction were separated by a centrifugation method using a solution for separation of mono and poly (manufactured by Dainippon Pharmaceutical) from human peripheral blood. After washing with an RPMI 1640 medium containing 10% fetal bovine serum (manufactured by Invitrogen), the cells were dispensed into a 96-well U-shaped plate to give a density of $1 \times 10^6$ cells/100 μL and centrifuged (1,800 rpm, 2 minutes) and then, after discarding the supernatant, reaction was carried out with biotin-labeled anti-PERP mouse antibody KM3411 and negative control antibody biotin-labeled KM511 (anti-granulocyte colony-stimulating factor derivative antibody) as a primary antibody together with human immunoglobulin (manufactured by Welfide)/BSA-PBS at ice temperature for 1 hour. The plate was washed with PBS 3 times, Red 670-labeled anti-streptavidin (manufactured by Coulter) was added at 50 μL/well as a secondary antibody and, further, FITC-labeled anti-human CD45 antibody (manufactured by Beckman Coulter) was added thereto at 10 μL/well, followed by reaction at ice temperature shading from the light for 1 hour. The plate was washed with PBS 3 times, followed by suspension in PBS, and wavelength of 505 to 545 nm or 660 to 700 nm excited with laser beam 488 nm Ar was measured by a flow cytometer (manufactured by Beckman Coulter).

Figure 9:
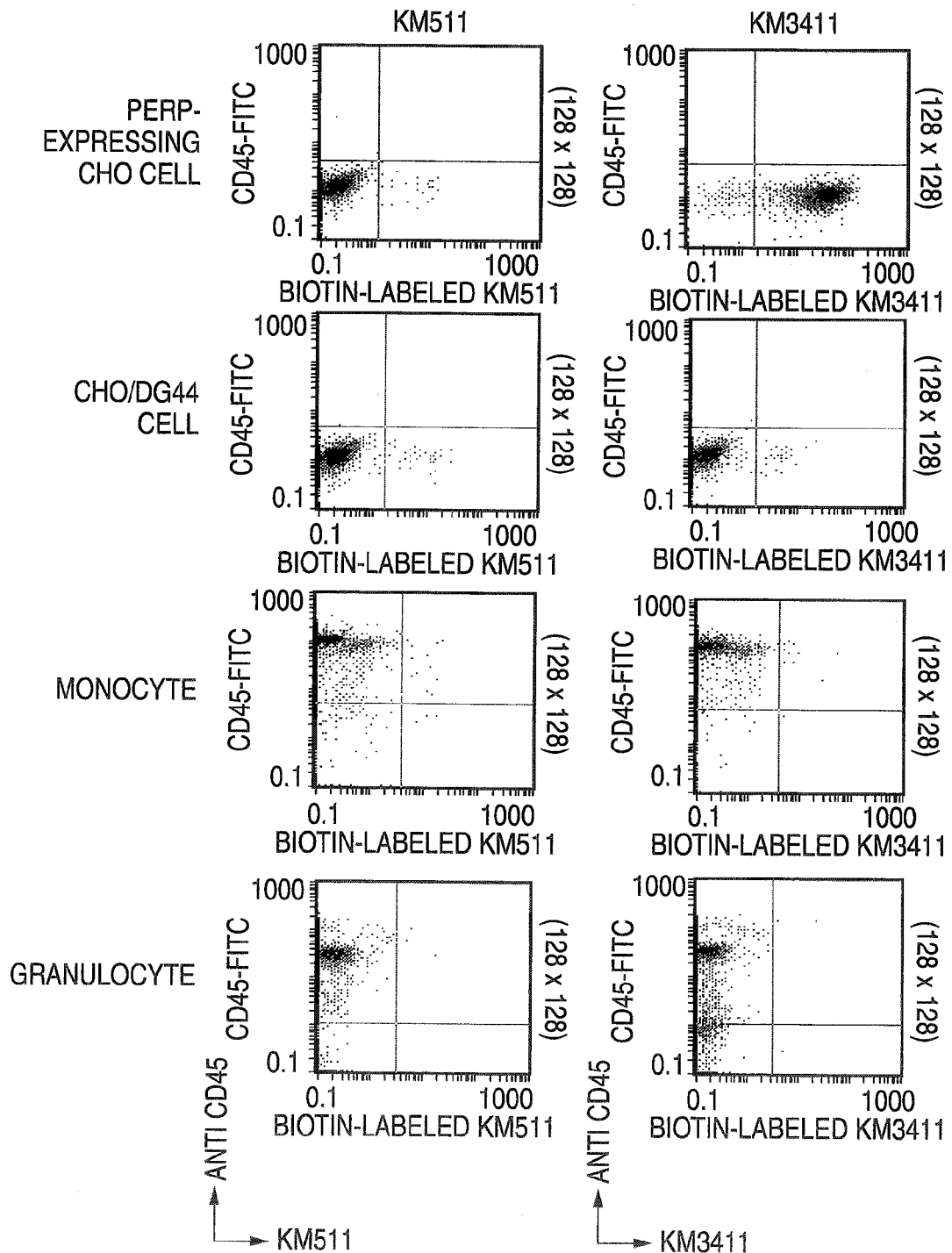
FIG. 9 shows reactivity of KM3411 in flow cytometry. The ordinate shows fluorescence intensity of FITC-labeled anti-human CD45 antibody, and the abscissa shows fluorescence intensity of biotin-labeled KM3411 or KM511 which is a negative control, Antibody used for staining the cells is shown on each histogram.

The result is shown in FIG. 9. Fluorescence intensity on the ordinate shows reactivity of the FITC-labeled anti-human CD 54 antibody, and fluorescence intensity on the abscissa shows reactivity of the biotin-labeled anti-PERP mouse antibody KM3411 or the negative control antibody biotin-labeled KM511. The biotin-labeled anti-PERP mouse antibody KM3411 did not react with monocytes and granulocytes in human peripheral blood.

Example 6

Comparison of Reactivity of Anti-PERP Mouse Antibody KM3411 with that of the Commercially Available Anti-PERP Antibody (Polyclonal Antibody)

Reactivity of the anti-PERP mouse antibody KM3411 and that of the anti-PERP polyclonal antibody (2451 of ProSci and NB500-231 of Novus Biologicals) to the PERP-expressing cells were compared by a flow cytometry.

As the cells, PERP/CHO cells and CHO/DG44 cells were used. The cells which were cultured for 2 to 3 days on an Iscove's Modified Dulbecco's medium (manufactured by Invitrogen) containing 10% fetal bovine serum and peeled off by 0.02% EDTA solution (manufactured by Nacalai Tesque) were washed with PBS and blocked for 20 minutes at ice temperature using BSA-PBS in order to avoid non-specific antibody adsorption. The cells were dispensed into a 96-well U-shaped plate to give a density of $1 \times 10^6$ cells/100 μL/BSA-PBS, followed by centrifugation (1,800 rpm for 2 minutes), the supernatant was discarded and 10 μg/ml of each of KM511 (anti-GCSF derivative antibody) as a negative control antibody of monoclonal antibody, anti-rat apo B polyclonal antibody (rabbit anti-serum-derived IgG fraction polyclonal antibody prepared using rat apo B as immunogen) as a negative control antibody of polyclonal antibody, anti-PERP mouse antibody KM3411 and 2 kinds of commercially available anti-PERP polyclonal antibodies product No. 2451 manufactured by ProSci and product No. NB-500-231 manufactured by Novus Biologicals) was dispensed at 50 μL/well as a primary antibody, followed by reaction at ice temperature for 60 minutes. After washing with PBS 3 times, FITC-labeled anti-mouse immunoglobulin G (H+L) (manufactured by Caltag) or FITC-labeled anti-rabbit immunoglobulin G (H+L) (manufactured by Kapel) was added at 20 μL/well as a secondary antibody, followed by reaction at ice temperature shading from the light for 30 minutes. Again, washing was carried out 3 times using PBS by a centrifugation method, followed by suspension in PBS, and wavelength of 510 to 530 nm excited by laser beam 488 nm Ar was measured by a flow cytometer (manufactured by Beckman Coulter).

Figure 10:
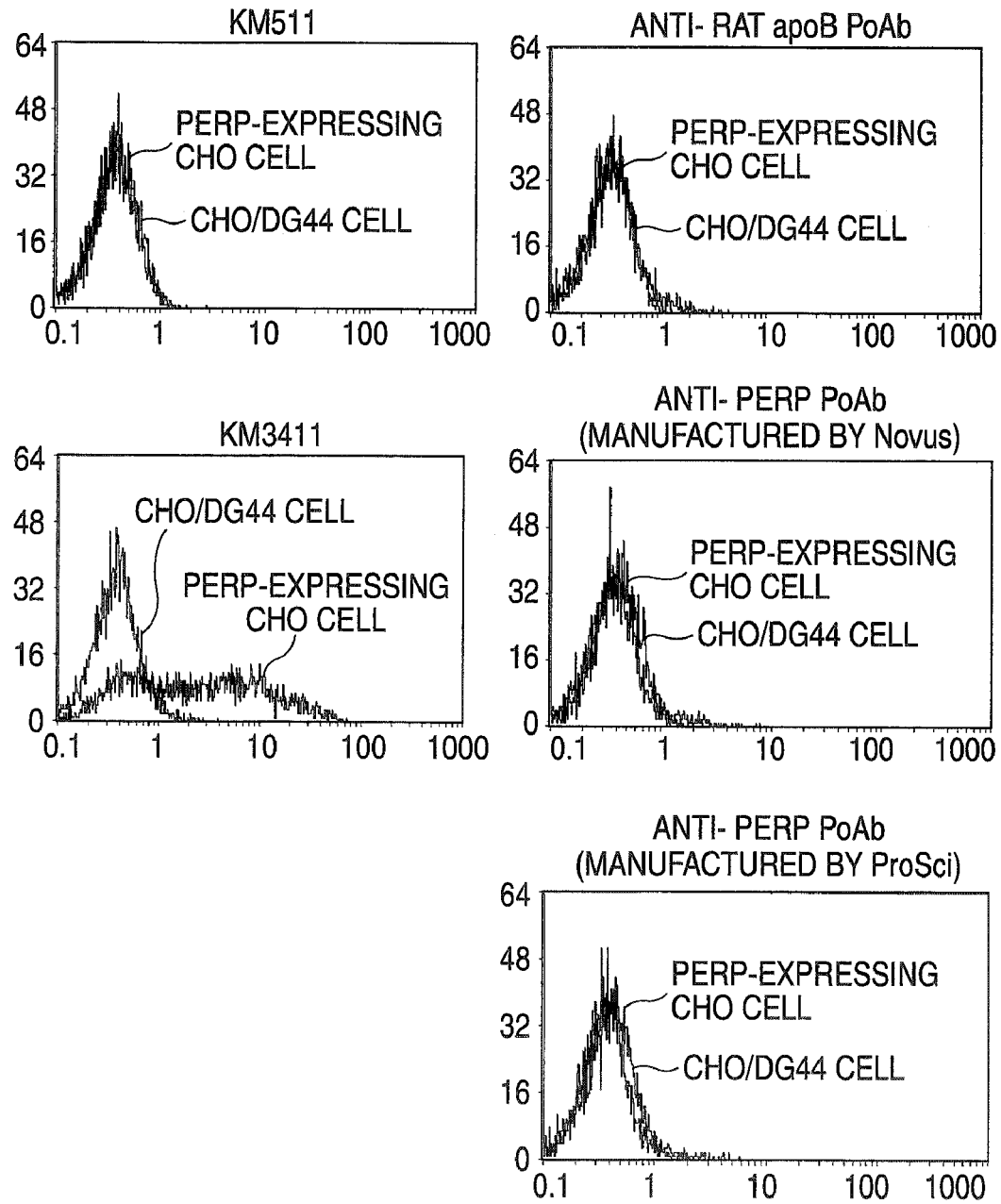
FIG. 10 shows reactivity of KM3411 using flow cytometry, various kinds of commercially available anti-PERP antibodies (polyclonal antibodies) and an antibody as a negative control to PERP/CHO cells and CHO/DG44 cells. In each of the drawings, the ordinate shows cell numbers, and the abscissa shows fluorescence intensity. Antibody used for staining the cells is shown on each histogram.

The result is shown in FIG. 10. The abscissa shows fluorescence intensity. Only in the case of the anti-PERP mouse antibody KM3411, fluorescence intensity was different between PERP/CHO cells and CHO/G44 cells and, therefore, it was shown that only anti-PERP mouse antibody KM3411 specifically reacts with the expressed PERP.

Example 7

Preparation of Anti-PERP Chimeric Antibody (1) Isolation and Analysis of cDNA Encoding Variable Region of Anti-PERP Mouse Antibody (1)-1 Preparation of mRNA from Anti-PERP Mouse Antibody-Producing Hybridoma From the hybridoma KM3411 described in Example 4, about 39 μg (from $4 \times 10^7$ hybridoma cells) of mRNA was prepared using Fast Track 2.0 Kit (manufactured by Invitrogen) which was a kit for preparation of mRNA according to the manufacture's instructions attached thereto.

(1)-2 Gene Cloning of H-Chain and L-Chain Variable Regions of Anti-PERP Mouse Antibody KM3411 mRNA (1 μg) of the anti-PERP mouse antibody KM3411 prepared in the above (1)-1 was subjected to BD SMART™ RACE cDNA Amplification Kit (manufactured by BD Biosciences) in accordance with the manufacture's instructions attached thereto to give cDNA having the sequence of BD SMART II™ Oligonucleotide attached to the kit at the 5'-terminal. The cDNA was used as a template and PCR was carried out using a universal primer A mix attached to the kit and a mouse Ig(γ)-specific primer represented by SEQ ID NO:9 so that the cDNA fragment of VH was amplified. Another PCR was carried out using a mouse Ig(κ)-specific primer represented by SEQ ID NO:10 in place of the Ig(γ)-specific primer to amplify the cDNA fragment of VL.

PCR was carried out by heating at 94° C. for 45 minutes; 5 cycles, one cycle consisting of reaction at 94° C. for 15 seconds and reaction at 72° C. for 3 minutes; 5 cycles, one cycle consisting of reaction at 94° C. for 15 seconds, reaction at 70° C. for 30 seconds and reaction at 72° C. for 3 minutes; and 30 cycles, one cycle consisting of reaction at 94° C. for 15 seconds, reaction at 68° C. for 30 seconds and reaction at 72° C. for 3 minutes, followed by reaction at 72° C. for 10 minutes. The PCR was carried out using a GeneAmp PCR System 9700 (manufactured by Applied Biosystems). The resulting PCR product had a size of about 500 bp in each of the H chain and the L chain.

In order to determine the nucleotide sequence of the resulting PCR product, about 0.05 pmol of DNA prepared by digesting pBluescript II SK(−) vector (manufactured by Stratagene) with SmaI and about 0.5 pmol of each of the PCR products prepared above were added to 6 μL of Solution I of Takara DNA Ligation Kit, ver. 2 (manufactured by Takara Shuzo) and 0.3 μL of a restriction enzyme SmaI to give a total volume of 12.3 μL, followed by reaction at 22° C. overnight. *Escherichia coli* DH5α (manufactured by Toyobo) was transformed using the thus obtained recombinant plasmid DNA solution. Each plasmid DNA was prepared from the clone of the transformant, followed by reaction using a Big Dye Terminator Cycle Sequencing FS Ready Reaction Kit (manufactured by PE Biosystems) according to the manufacture's instructions attached thereto and then the nucleotide sequence was analyzed using a sequencer ABI PRISM 3700 manufactured by the same company. As a result, a plasmid pKM3411H#9 containing a full-length H chain cDNA and a plasmid pKM3411L#4 containing an L-chain cDNA in which ATG sequence presumed to be an initiation codon was present at the 5' terminal of cDNA were prepared.

(1)-3 Analysis of Amino Acid Sequence of V Region of the Anti-PERP Mouse Antibody A full length of nucleotide sequence contained in the plasmid pKM3411H#9 is represented by SEQ ID NO:11, a full length of amino acid sequence of a secretory VH containing a signal sequence deduced from the above sequence is represented by SEQ ID NO:12, a full length of nucleotide sequence of VL contained in the plasmid pKM3411L#4 is represented by SEQ ID NO:13 and a full length of amino acid sequence of a secretory VL containing a signal sequence deduced from the above sequence is represented by SEQ ID NO:14. From the comparison with sequence data of known mouse antibodies [*SEQUENCES of Proteins of Immunological Interest*, U.S. Dept. Health and Human Services (1991)] and from the comparison with the result of analysis of the N-terminal amino acid sequences in the H chain and the L chain of the purified anti-PERP mouse antibody KM3411 using a protein sequencer (PPSQ-10 manufactured by Shimadzu), it has been clear that each of the isolated cDNAs is a full-length cDNA encoding the anti-PERP mouse antibody KM3411 containing a secretory signal sequence; in the H chain, the amino acid sequence from positions 1 to 18 in the amino acid sequence represented by SEQ ID NO:12 is the secretory signal sequence; and, in the L chain, the amino acid sequence from positions 1 to 22 in the amino acid sequence represented by SEQ ID NO:14 is the secretory signal sequence.

Then, novelty of the amino acid sequences of VH and VL of the anti-PERP mouse antibody KM3411 was examined. GCG Package (version 9.1, manufactured by Genetics Computer Group) was used as a sequence analysis system and amino acid sequence database of known proteins were searched by BLASTP method [*Nucleic Acid Res.* 25, 3389 (1997)]. As a result, no completely identical amino acid sequence was found for both VH and VL and it was confirmed that VH and VL of the anti-PERP mouse antibody KM3411 have novel amino acid sequences.

Furthermore, CDRs of VH and VL of the anti-PERP mouse antibody KM3411 were identified by comparing them with the amino acid sequences of known antibodies. Amino acid sequences of CDR1, CDR2 and CDR3 of VH of the anti-PERP mouse antibody KM3411 were represented by SEQ ID NOs:15, 16 and 17, respectively, and amino acid sequences of CDR1, CDR2 and CDR3 of VL thereof were represented by SEQ ID NOs:18, 19 and 20, respectively.

(2) Stable Expression Using Animal Cells of Anti-PERP Chimeric Antibody (2)-1 Construction of Anti-PERP Chimeric Antibody-Expressing Vector pKANTEX3411

Anti-PERP chimeric antibody-expressing vector pKANTEX3411 was constructed as follows using the vector for humanized antibody expression, pKANTEX93, described in WO 97/10354 and plasmids pKM3411H#9 and pKM3411#4 prepared in (1)-2 of this Example.

In order to prepare cDNA encoding VH of the anti-PERP mouse antibody KM3411 by PCR, synthetic DNAs having the nucleotide sequences represented by SEQ ID NOs:21 and 22 were designed and synthesized, and in order to prepare cDNA encoding VL, synthetic DNAs having the nucleotide sequences represented by SEQ ID NOs:23 and 24 were designed and synthesized. Each synthetic DNA (manufactured by Genset) contains a restriction enzyme recognizing sequence at the 5' terminal for cloning to pKANTEX93. The plasmid pKM3411H#9 (20 ng) prepared in (1)-2 of this Example was added to a buffer containing 50 μL of PCR Buffer #1 (manufactured by Toyobo) attached to KOD DNA Polymerase, 0.2 mmol/L dNTPs, 1 mmol/L magnesium chloride and 0.5 μmol/L of synthetic DNAs having the nucleotide sequence represented by SEQ ID NOs:21 and 22. After heating at 94° C. for 3 minutes using a thermal cycler, 2.5 units of KOD DNA Polymerase (manufactured by Toyobo) was added thereto and reaction was carried out by 25 cycles, one cycle consisting of reaction at 94° C. for 30 seconds, reaction at 58° C. for 30 seconds and reaction at 74° C. for 1 minute. Similarly, 20 ng of the plasmid pKM3411L#4 prepared in (1)-2 of this Example was added to a buffer containing 50 μL of PCR Buffer #1 (manufactured by Toyobo) attached to KOD DNA Polymerase, 0.2 mmol/L dNTPs, 1 mmol/L magnesium chloride and 0.5 μmol/L of synthetic DNAs having the nucleotide sequence represented by SEQ ID NOs:23 and 24 and then PCR was carried out according to the above-described method. The reaction solution (40 μL) was subjected to agarose gel electrophoresis and subjected to QIAquick Gel Extraction Kit (manufactured by Qiagen) to recover a PCR product of VH of about 0.47 kb and a PCR product of VL in about 0.45 kb.

Figure 11:
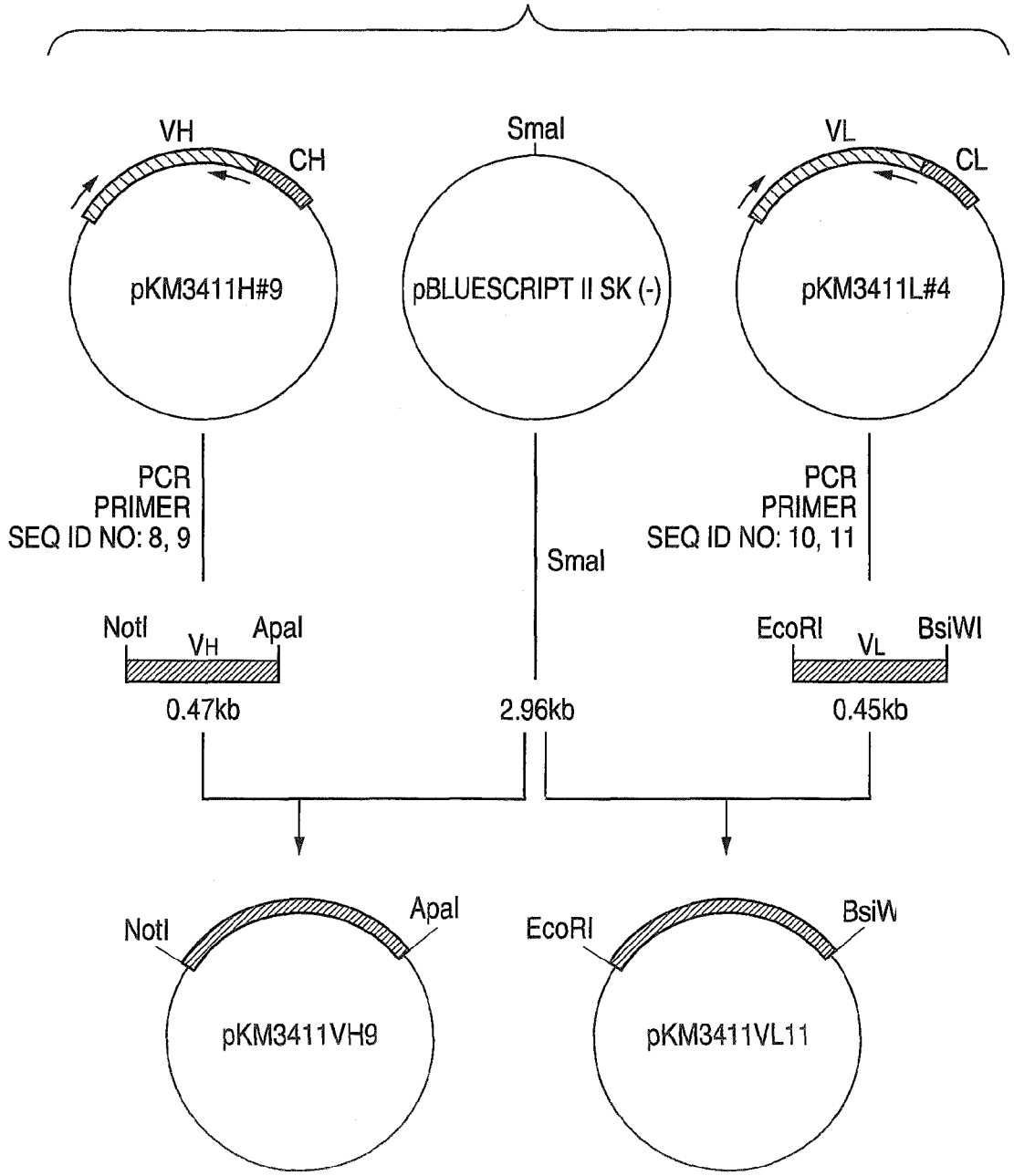
FIG. 11 shows a step for construction of plasmids pKM3411VH9 and pKM33411VL11.

Then, 0.05 pmol of DNA obtained by digesting a plasmid pBluescript II SK(−) (manufactured by Stratagene) with a restriction enzyme SmaI (manufactured by Takara Shuzo) and 0.5 μmol of each of the above-prepared each PCR product were added to sterile water to give a volume of 10 μL, and 10 μL of solution I of Takara ligation kit ver. 2 (manufactured by Takara Shuzo) and 0.5 μL of a restriction enzyme SmaI (manufactured by Takara Shuzo) were further added thereto, followed by reaction at 22° C. overnight. *Escherichia coli* DH5α (manufactured by Toyobo) was transformed using the above-prepared recombinant DNA solution. From the clone of the resulting transformant, each plasmid DNA was prepared, followed by reaction using a Big Dye Terminator Cycle Sequencing FS Ready Reaction Kit (manufactured by PE Biosystems) according to the manufacturers instructions attached thereto, the nucleotide sequence was analyzed using DNA Sequencer ABI PRISM 3700 of the same company and it was confirmed that the plasmids pKM3411VH9 and pKM3411VL11 shown in FIG. 11 having desired nucleotide sequences were prepared.

Then, each of vector for humanized antibody expression, pKANTEX93, and the above-prepared pKM3411VL11 was digested with a restriction enzyme BsiWI (manufactured by New England BioLab) and then digested with a restriction enzyme EcoRI (manufactured by Takara Shuzo). The reaction solution after the digestion was subjected to agarose gel electrophoresis and each of EcoRI-BsiWI fragment of VL of about 0.45 kb and EcoRI-BsiWI fragment of pKANTEX93 of about 12.7 kb was recovered using QIAquick Gel Extraction Kit (manufactured by Qiagen).

Figure 12:
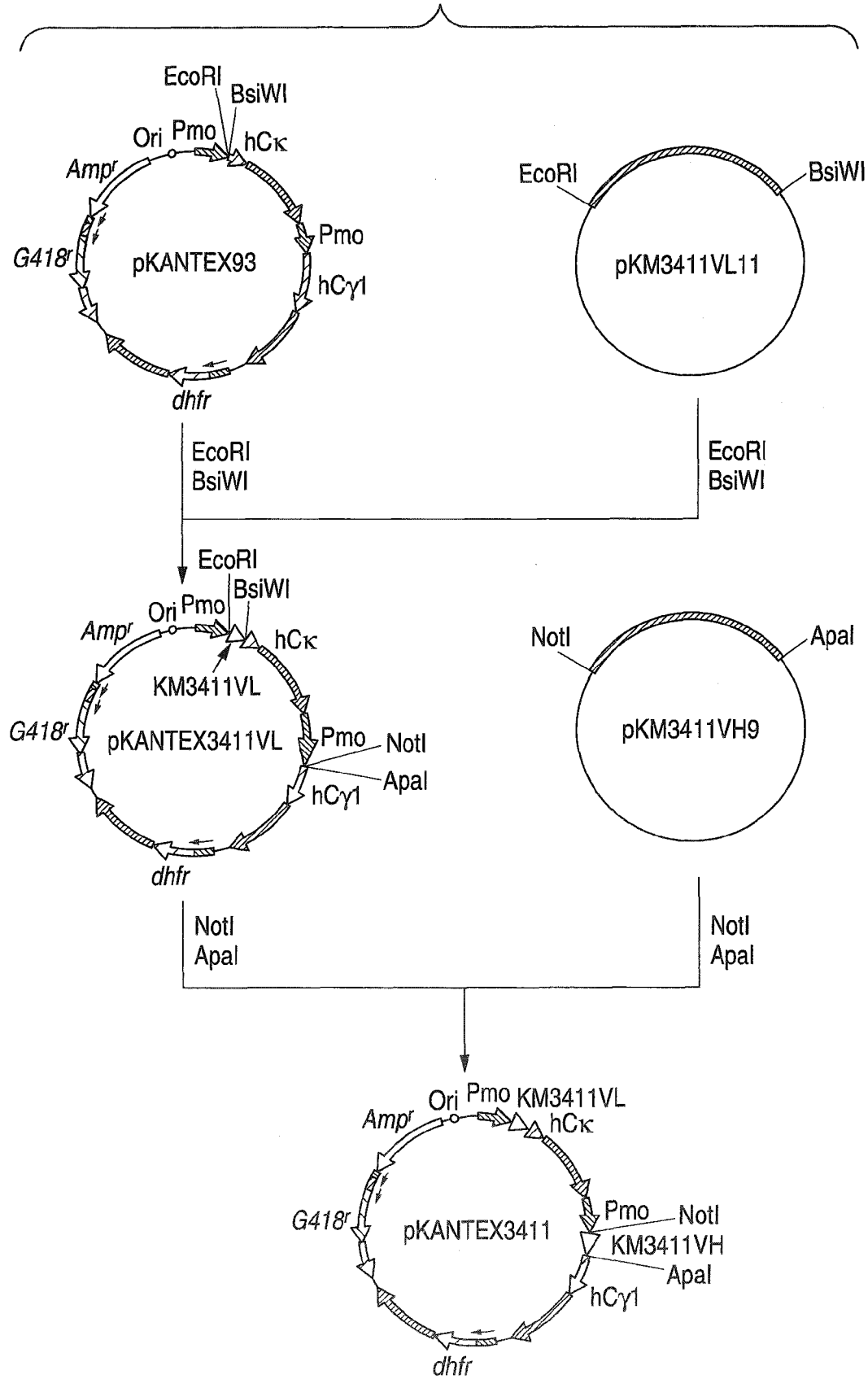
FIG. 12 shows a step for construction of a plasmid pKAN-TEX3411.

The resulting 2 different fragments were ligated using Ligation High (manufactured by Toyobo) according to the manufacture's instructions attached thereto and the resulting recombinant plasmid DNA solution was used for the transformation of the *Escherichia coli* DH5α (manufactured by Toyobo). From a clone of the resulting transformant, each plasmid DNA was prepared and treated with restriction enzyme to confirm that a plasmid pKANTEX3411 VL as shown in FIG. 12 into which the desired EcoRI-BsiWI fragment of about 0.45 kb was inserted was obtained.

Then, each of the above-prepared pKANTEX3411VL and pKM3411VH9 was digested with a restriction enzyme ApaI (manufactured by Takara Shuzo) and then with a restriction enzyme NotI (manufactured by Takara Shuzo). The reaction solution after the digestion was subjected to agarose gel electrophoresis and each of ApaI-NotI fragment derived from pKANTEX3411V of about 132 kb and ApaI-NotI fragment derived from pKM3411VH of about 0.47 kb was recovered. The resulting 2 kinds of fragments were ligated using Ligation High (manufactured by Toyobo) according to the manufacture's instructions attached thereto and, using the resulting recombinant plasmid DNA solution, *Escherichia coli* DH5α (manufactured by Toyobo) was transformed. Each plasmid DNA was prepared from the resulting clone of the transformant and treated with to confirm that restriction enzyme that a plasmid pKANTEX3411 as shown in FIG. 12 into which the desired ApaI-NotI fragment of about 0.47 kb was inserted was prepared. With regard to the plasmid, after the reaction was carried out using BigDye Terminator Cycle Sequencing FS Ready Reaction Kit (manufactured by PE Biosystems) according to the manufacture's instructions attached thereto and the nucleotide sequence was analyzed by DNA Sequencer ABI PRISM 3700 of the same company and, as a result, it was confirmed that the desired plasmid in which each of cDNA encoding VH of the KM3411 and cDNAs encoding VL was cloned was prepared.

(2)-2 Expression in Animal Cells of Anti-PERP Chimeric Antibody

Expression of the anti-PERP chimeric antibody in animal cells was carried out using the anti-PERP chimeric antibody expressing vector pKANTEX3411 prepared in (2)-1 of this Example by a usual method [*Antibody Engineering, A Practical Guide*, W. H. Freeman and Company (1992)] and a transformant KM3481 into which pKANTEX3411 was introduced was prepared.

(3) Preparation of Pure Antibody

After the transformant prepared in (2)-2 of this Example was cultured by a usual culturing method, the cell suspension was recovered and centrifuged at 3,000 rpm and at 4° C. for 5 minutes and the recovered culture supernatant was sterilized by filtering through a Millex GV Filter (manufactured by Millipore) having a pore size of 0.22 µm. From the resulting culture supernatant, an anti-PERP chimeric antibody KM3481 was purified using a Mab Select (manufactured by Amersham Bioscience) column according to the manufacture's instructions attached thereto.

Degree of purification and expressed molecular size of the resulting anti-PERP chimeric antibody KM3481 were confirmed by SDS-PAGE using a gradient gel (manufactured by Atto; catalog no. E-T520L) according to the manufacture's instructions attached thereto. Anti-PERP mouse antibody KM3411 was electrophoresed as a control at the same time.

Figure 13:
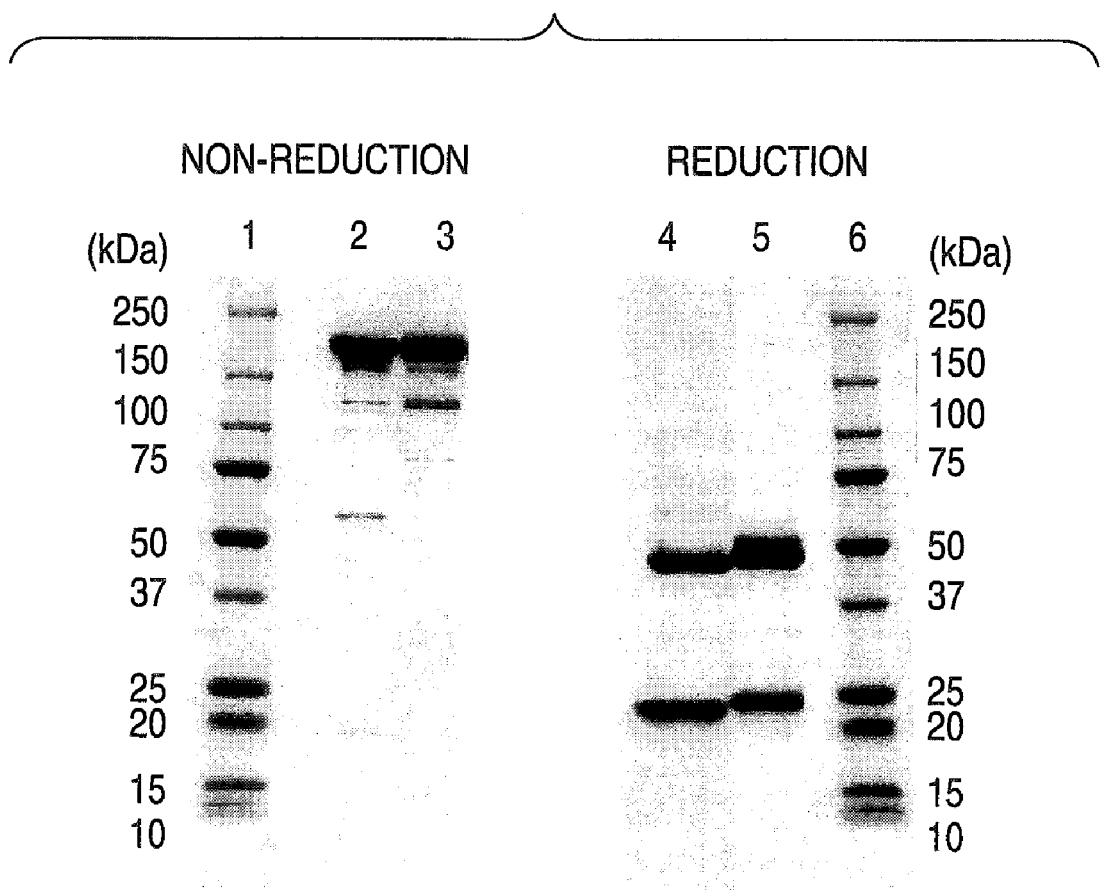
FIG. 13 shows electrophoretic patterns of the purified anti-PERP chimeric antibody by SDS-PAGE (using 5 to 20% gradient gel). Left and right sides are results of electrophoresis carried out under non-reducing condition and reducing conditions, respectively. Lanes 1 and 6, lanes 2 and 4 and lanes 3 and 5 show electrophoretic patterns of a molecular weight marker, anti-PERP mouse antibody KM3411 and anti-PERP chimeric antibody KM3481, respectively.

The result is shown in FIG. 13. In the purified anti-PERP chimeric antibody KM3481, one band for molecular weight of about 150 kilodaltons (hereinafter, referred to as "Kd") was found under non-reducing conditions, and two bands of about 50 Kd and about 25 Kd were found under reducing conditions. Those molecular weights coincide with the report [*Antibodies—A Laboratory Manual*, Cold Spring Harbor Laboratory, Chapter 14 (1988), *Monoclonal Antibodies—Principles and practice*, Academic Press Limited (1996)] that under non-reducing conditions, antibodies of the IgG class have a molecular weight of about 150 Kd and under reducing conditions, and S—S bond in the molecule is cleaved to decompose into an H chain having a molecular weight of about 50 Kd and an L chain having a molecular weight of about 25 Kd. Thus, it was confirmed that the anti-PERP chimeric antibody KM 3481 was expressed as an antibody molecule having a correct structure.

Example 8

Evaluation of Activity of Anti-PERP Chimeric Antibody (1) Binding Activity to PERP on Membrane Surface (Fluorescent Antibody Method)
(1)-1 Binding Activity to PERP/CHO Cells Binding activity of the anti-PERP chimeric antibody KM3481 purified in (3) of Example 7 with PERP/CHO cells was examined by a fluorescent antibody method as follows.

PERP/CHO cells were dispensed at $2 \times 10^5$ cells per well onto a 96-well U-shaped plate, anti-PERP chimeric antibody KM 3481 diluted for seven times in 5-fold dilution steps from 20 µg/mL using a buffer for FCM (1% of BSA-PBS, 0.02% of EDTA and 0.05% of $NaN_3$) was dispensed at 50 µL/well, and an antibody solution in which human immunoglobulin (manufactured by Sigma) diluted to 400 µg/mL was further dispensed thereinto at 50 µL/well in order to prevent nonspecific staining, followed by reaction in ice for 30 minutes. After washing with a buffer for FCM twice, a solution in which PE-labeled anti-human IgG (H+L) antibody (manufactured by Beckman Coulter) was diluted 50-fold with a buffer for FCM was added thereto at 50 µL/well. After reaction in ice shading from the light for 30 minutes, washing with a buffer for FCM was carried out 3 times and fluorescence intensity was measured using a flow cytometer.

Figure 14:
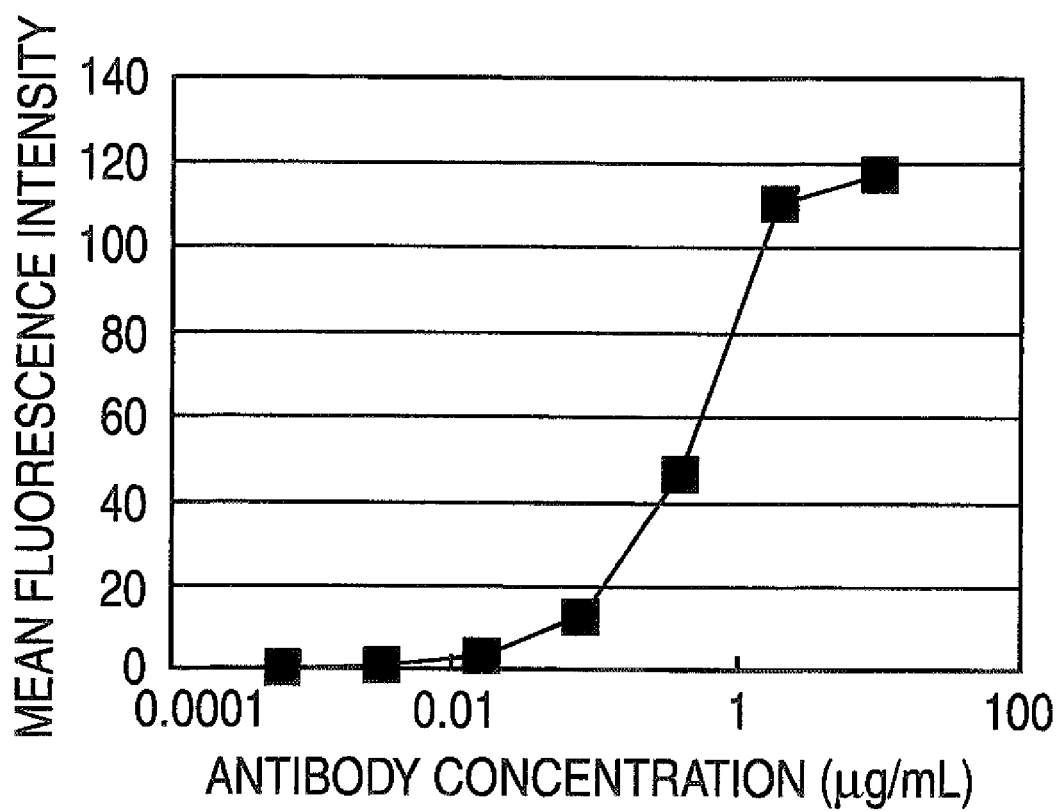
FIG. 14 shows reactivity of purified anti-PERP chimeric antibody KM3481 to PERP/CHO cells using flow cytometry. The ordinate and the abscissa show mean fluorescence intensity and an antibody concentration, respectively.

The result is shown in FIG. 14. The ordinate shows mean fluorescence intensity (MFI) and the abscissa shows an antibody concentration. It was shown that the anti-PERP chimeric antibody KM3481 was bound to PERP/CHO cells and the intensity of the binding activity was dependent on the concentration of the antigen.

(1)-2 Binding Activity to Human Cancer Cell Line

PC9, NCI-H69, Capan-2 and BxPC-3 cells were selected from the human cancer cell lines examined in (2)-1 of Example 5 and binding activity of the anti-PERP chimeric antibody KM3481 (10 µg/mL) was measured using the method described in (1)-1 of this Example. As to a negative control, an anti-CCR4 chimeric antibody (WO 01/64754) was used.

Figure 15:
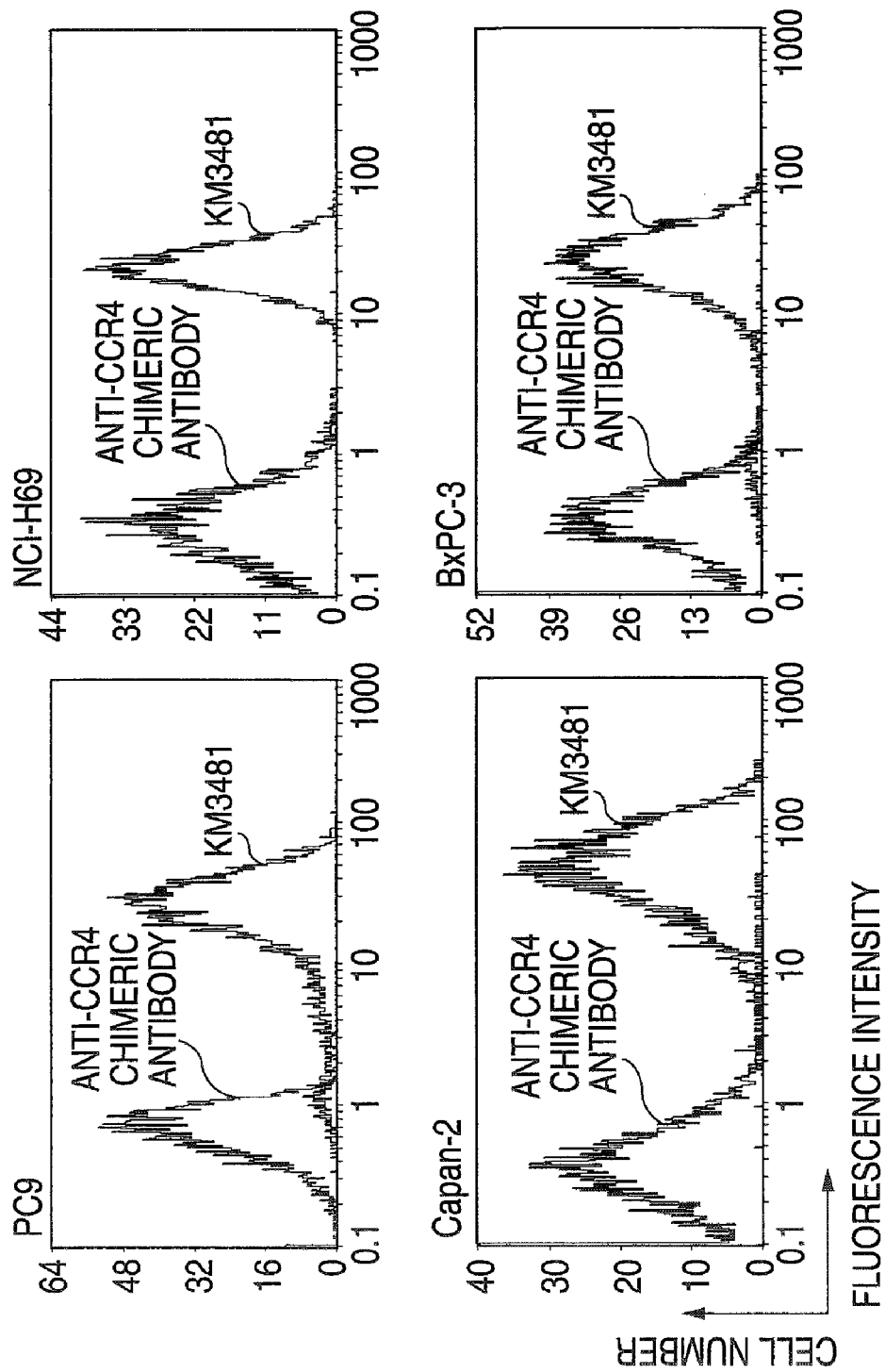
FIG. 15 shows reactivity of anti-PERP chimeric antibody KM3481 to each cancer cell line using flow cytometry. The ordinate and the abscissa show cell numbers and fluorescence intensity, respectively.

The result is shown in FIG. 15. The anti-PERP chimeric antibody KM3481 shows binding activity to any of the above-described cell lines.

(2) Complement-Dependent Cytotoxic Activity (CDC Activity) of Anti-PERP Chimeric Antibody The CDC activity of the anti-PERP chimeric antibody KM3481 prepared in Example 7 was measured by a method described below.

(2)-1 Preparation of a Target Cell Solution

PERP/CHO cells were washed with an IMDM medium [IMDM-(5) medium] containing 5% FCS by centrifugation and suspension and then cell concentration was adjusted to $2\times10^5$ cells/mL by the IMDM-(5) medium to give a target cell solution.

(2)-2 Preparation of Human Complement Solution

Freeze-dried human serum (Human Complement Serum manufactured by Sigma) was dissolved in deionized water and diluted 2-fold by addition of the same amount of the IMDM-(5) medium to give a human complement solution.

(2)-3 Measurement of CDC Activity

The target cell solution (50 μL) ($1\times10^4$ cells/well) prepared in the above (2)-1 was dispensed into a 96-well flat plate (manufactured by Sumitomo Bakelite). Then, antibody solutions in various concentrations diluted with the IMDM-(5) medium was added, then 50 μL of the complement solution prepared in the above (2)-2 was added to give a total volume of 150 μL, followed by reaction at 37° C. for 2 hours. A cell proliferation reagent WST-1 (manufactured by Roche) (15 μL each) was added to each well, followed by reaction at 37° C. for 4 hours or more, and absorbance at 450 nm (OD450, depending upon living cell numbers) was measured. Absorbance data of the background were obtained using the IMDM-(5) medium, instead of the target cell solution and the antibody solution, and absorption data using the IMDM-(5) medium, instead of an antibody solution (antibody concentration: 0 μg/mL) were obtained as cytotoxic activity at 0%. CDC activity was calculated by the following formula.

CDC Activity (%)=([Absorption data at antibody concentration of 0 μg/mL]−[Absorption data of the sample])/[Absorption data at antibody concentration of 0 μg/mL]×100

Figure 16:
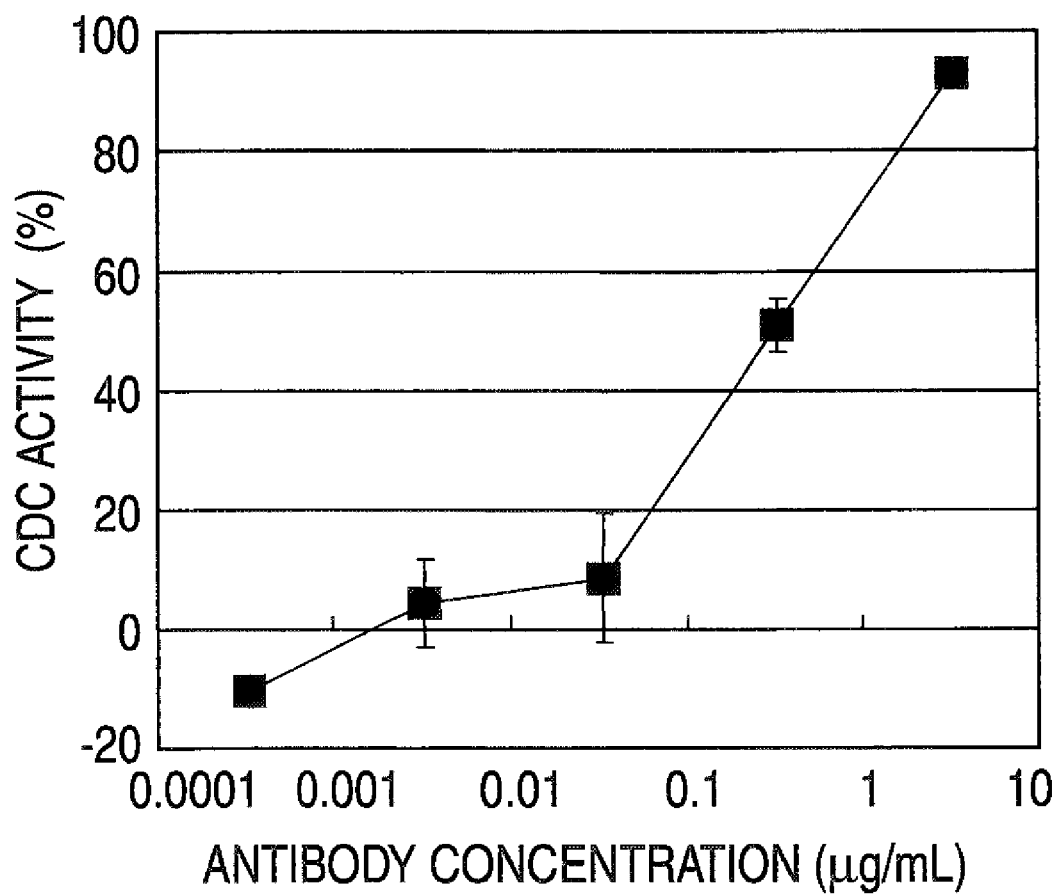
FIG. 16 shows CDC activity of anti-PERP chimeric antibody KM3481 to PERP/CHO cells. The ordinate and the abscissa show cytotoxic activity (%) and an antibody concentration, respectively.

The result is shown in FIG. 16. The anti-PERP chimeric antibody KM3481 showed CDC activity to the PERP/CHO cells in concentration-dependent manner and the activity was dependent on the concentration of the antibody.

(3) ADCC Activity of Anti-PERP Chimeric Antibody

ADCC activity of the anti-PERP chimeric antibody KM3481 prepared in Example 7 was measured as follows. As target cells, 4 different cell lines in which expression of polypeptide encoded by the PERP gene was confirmed, i.e., PC9, NCI-1169, Capan-2 and BxPC-3 cell lines used in (1) of this Example and PERP/CHO cells were used as a positive control and CHO/DG44 cell line in which the polypeptide was not expressed was used as a negative control, and lymphoprep (manufactured by NYCOMED) was used for preparation of an effector cell solution.

(3)-1 Preparation of Target Cell Solution

In the case of PERP/CHO cells, each cell line was cultured using the IMDM-(10) medium, and in the case of other cancer cell lines, each cell line was cultured using an RPMI 1640-FCS(10) medium [an RPMI 1640 medium containing 10% of FCS (manufactured by Invitrogen)], the cells were washed with a medium for supernatent of ADCC activity RPMI 1640-FCS(5) [an RPMI 1640 medium containing 5% FCS (manufactured by Invitrogen)] by centrifugation and suspension and then the cell concentration was adjusted to $2\times10^5$ cells/mL with a medium for measurement of ADCC activity to prepare a target cell solution.

(3)-2 Preparation of Effector Cell Solution

Intravenous blood (50 mL) of healthy person was collected and 0.5 mL of heparin sodium (manufactured by Shimizu Seiyaku) was added, followed by gentle stirring. From it, a monocyte (PBMC) fraction was separated by using Lymphoprep (manufactured by NYCOMED) according to the manufacture's instructions attached thereto. The separated PBMC fraction was washed with a medium for measurement of ADCC activity by centrifugation 3 times and then appropriately suspended to give an effector cell solution.

(3)-3 Measurement of ADCC Activity

The target cell solution prepared in the above (3)-1 (50 μL) ($1\times10^4$ cells/well) was dispensed into a 96-well U-shaped bottom plate. Then, 50 μL of the effector cell solution prepared in (3)-2 (when PERP/CHO cells were used as a target, dilution was carried out to adjust the ratio of the effector cells to the target cells to 15:1 and, in other cases, to adjust the ratio to 20:1) was added thereto. Furthermore, the anti-PERP chimeric antibody was diluted by a medium for measurement of ADCC activity and added thereto to give a final concentration of 0.001 to 10 μg/ml each and to make the total volume of 150 μL, followed by reaction at 37° C. for 4 hours. After the reaction, the plate was centrifuged and lactic acid dehydrogenase (LDH) activity in the supernatant was measured by obtaining absorbance data using CycoTox 96 Non-Radioactive Cytotoxicity Assay (manufactured by Promega) according to the manufacture's instructions attached thereto. Absorbance data of spontaneous release of the target cell were obtained using a medium for measurement of ADCC activity in place of the effector cell solution and the antibody solution, and absorbance data of spontaneous release of the effector cell were obtained using a medium for measurement of ADCC activity in place of the target cell solution and the antibody solution, followed by carrying out the same operation as above. Absorbance data of total release of the target cell were obtained using a medium for measurement of ADCC activity in place of the antibody solution and the effector cell solution, by adding 15 μL of 9% Triton X-100 solution at 45 minutes before completion of the reaction and carrying out the same operation as above. ADCC activity was determined by the following formula.

ADCC activity (%)={(absorbance of sample−absorbance of spontaneous release of effector cell−absorbance of spontaneous release of target cell)/(absorbance of total release of target cell absorbance of spontaneous release of target cell)}×100    (Formula)

Figure 17:
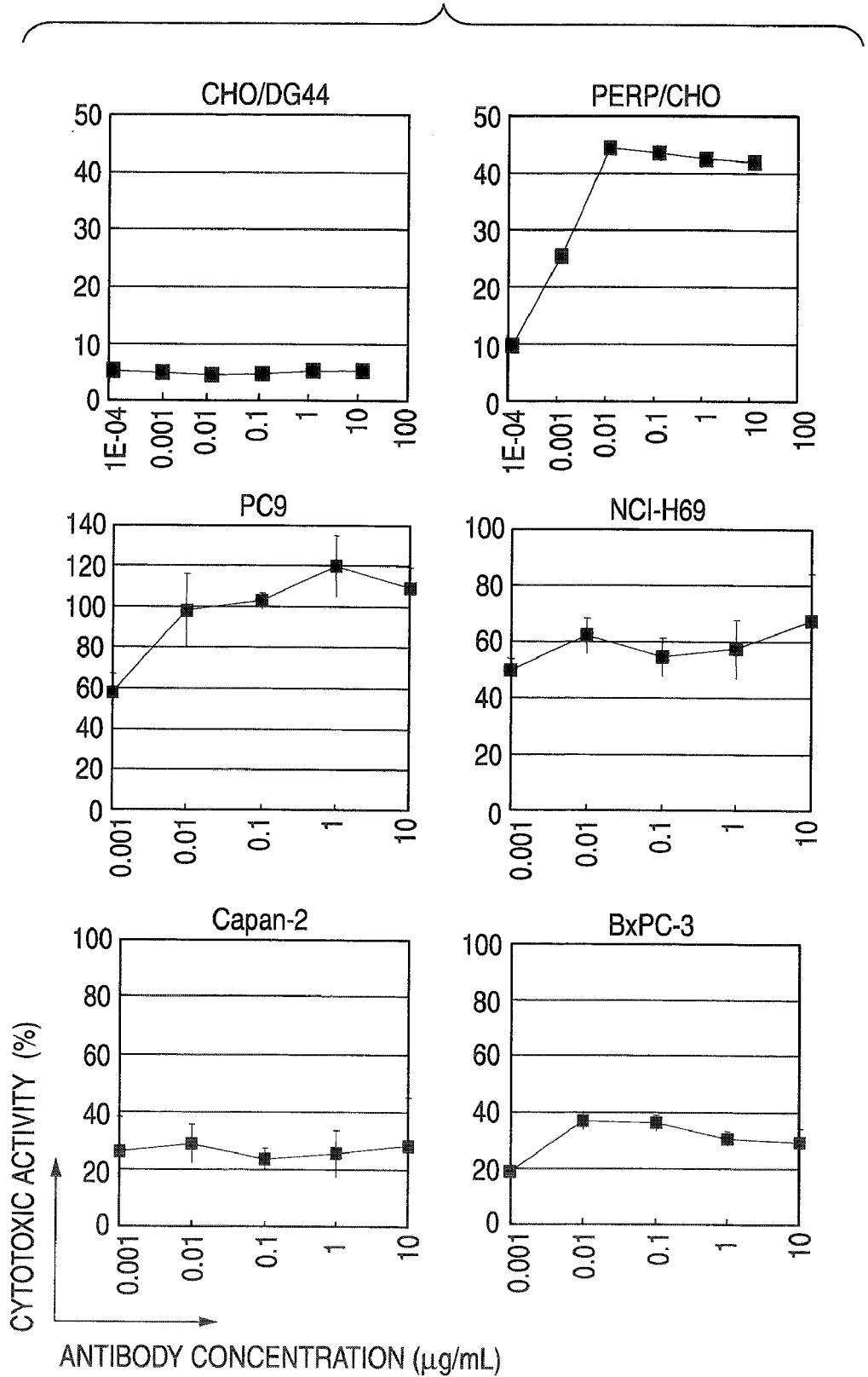
FIG. 17 shows ADCC activity of anti-PERP chimeric antibody KM3481 to each cell line. The ordinate and the abscissa show cytotoxic activity (%) and an antibody concentration, respectively.

The result is shown in FIG. 17. The anti-PERP chimeric antibody KM3481 had ADCC activity to PERP/CHO, PC9, NCI-H69, Capan-2 and BxPC-3 cell lines which were confirmed to express a polypeptide encoded by the PERP gene among the total cell lines used as target cells. On the other hands the anti-PERP chimeric antibody KM3481 had no ADCC activity to CHO/DG44 cells used as a negative control.

Example 9

In Vivo Test for Pharmaceutical Effect of the Anti-PERP Chimeric Antibody

With regard to lung cancer and pancreatic cancer, an in vivo test for pharmaceutical effect of the anti-PERP chimeric antibody was examined in a mouse xenograft initial cancer model as follows.

On the day before the transplantation of cancer cells, body weight of each SCID mice (CLEA Japan, Inc., male, 6 weeks old) was measured and divided into four groups (6 mice per each group), i.e., a group to which no antibody was administered and three groups to which 0.1, 1 or 1.0 mg/kg of the antibody was administered. PERP-positive lung cancer cell line PC-9 or PERP-positive pancreatic cancer cell line BxPC-3 cultured by a usual method in $5\times10^7$ cells/mL was suspended in RPMI 1640 medium (manufactured by Invitrogen) and each 100 μL thereof was transplanted into right flank skin of the mouse. Cell numbers for each mouse were $5×10^6$ cells. Starting from the transplanted day, the anti-PERP chimeric antibody KM3481 diluted with a citrate buffer (10 mmol/L citric acid and 150 mmol/L sodium chloride; pH 6) was intravenously administered at 100 μL for twice a week, 8 times in total. Only the citrate buffer was administered to the group to which no antibody was added.

The date on which the tumor was transplanted was defined as 0 day, and tumor diameter was measured using vernier calipers with lapse of days. Tumor volume was calculated using the following formula.

Tumor volume=Minor axis×Minor axis×Major axis× 0.5

Figure 18:
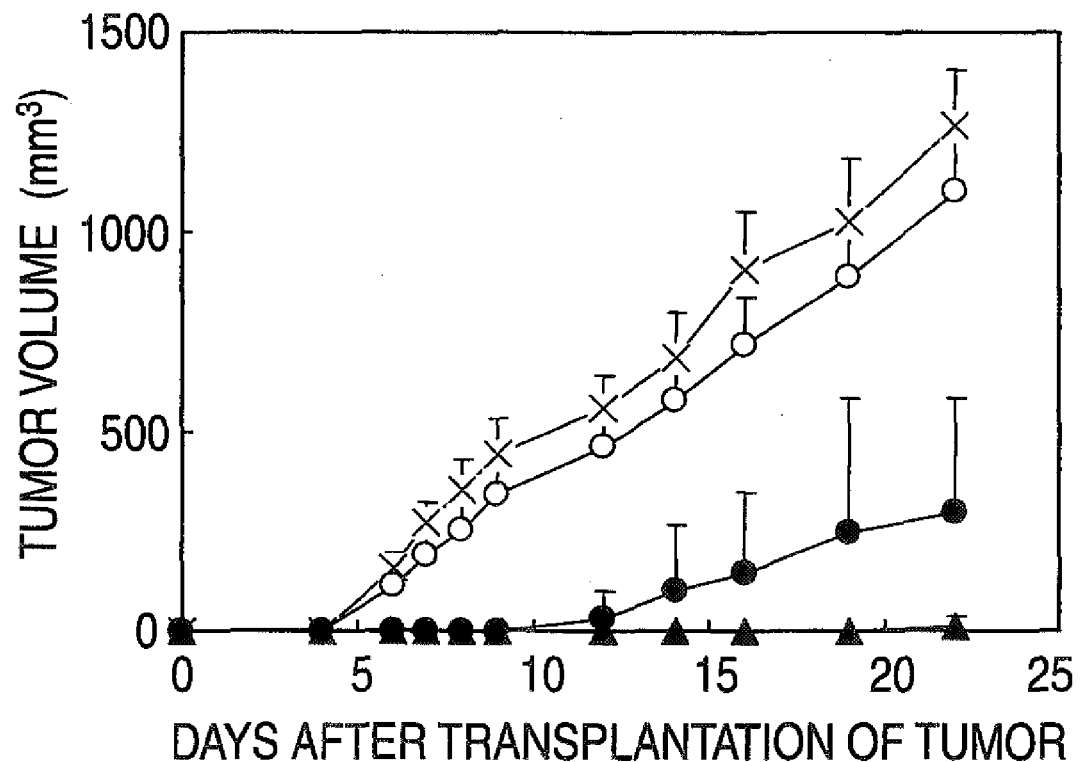
FIG. 18 shows changes with lapse of days for a mean value of tumor volumes in an administered group when anti-PERP chimeric antibody KM3481 was administered to a mouse to which lung cancer cell line PC-9 was intradermally transplanted. The abscissa and the ordinate show days after transplantation of tumor and the tumor volume, respectively. In the drawing, x shows a group to which no antibody was administered; ○ shows a group to which 0.1 mg/kg of anti-PERP chimeric antibody KM3481 was administered; ● shows a group to which 1 mg/kg of anti-PERP chimeric antibody KM3481 was administered; and ▲ shows a group to which 10 mg/kg of anti-PERP chimeric antibody KM3481 was administered. Bar shows a standard deviation.
Figure 19:
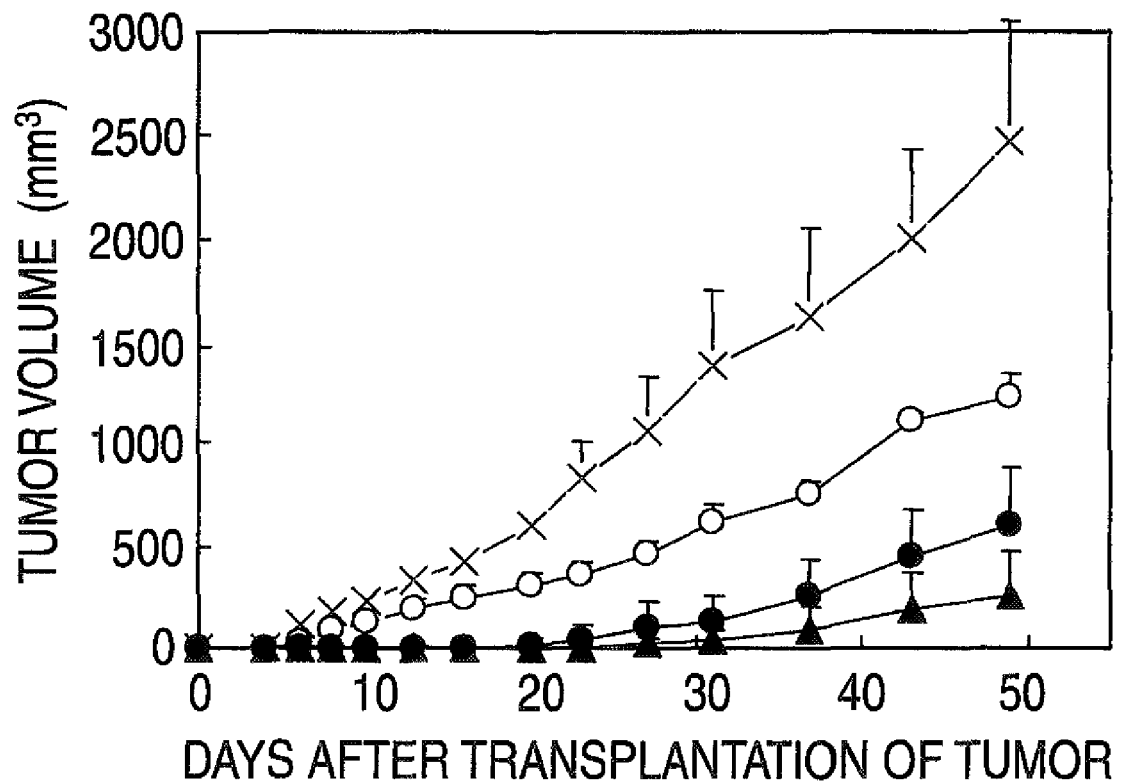
FIG. 19 shows changes with lapse of days for a mean value of tumor volumes in an administered group when anti-PERP chimeric antibody KM3481 was administered to mouse to which pancreatic cancer cell line BxPC-3 was intradermally transplanted. The abscissa and the ordinate show days after transplantation of tumor and the tumor volume, respectively. In the drawing, x shows a group to which no antibody was administered; ○ shows a group to which 0.1 mg/kg of anti-PERP chimeric antibody KM3481 was administered; ● shows a group to which 1 mg/kg of anti-PERP chimeric antibody KM3481 was administered; and ▲ shows a group to which 10 mg/kg of anti-PERP chimeric antibody KM3481 was administered. Bar shows a standard deviation.

Changes in the mean value of tumor volume of each group in lung cancer and pancreatic cancer models with lapse of days are shown in FIG. 18 and FIG. 19, respectively.

In a lung cancer model as shown in FIG. 18, death of the mice to which no antibody was administered started on the 22nd day and thereafter and, therefore, evaluation of the tumor volume was finished on the 22nd day.

In a lung cancer model in which 1 or 10 mg/kg of the anti-PERP chimeric antibody KM3481 was administered, significant effects for inhibition of tumor adhesion and suppression of tumor growth as compared with the group to which no antibody was administered were found.

In the pancreatic cancer model as shown in FIG. 19, significant effects for inhibition of tumor adhesion and suppression of tumor growth were found in the group to which 1 and 10 mg/kg was administered, and a significant inhibitory effect was also found in the group to which 0.1 mg/kg was administered.

From the above, it is now apparent that, in the models of initial cancers using lung cancer and pancreatic cancer as targets, the anti-PERP chimeric antibody KM3481 has antitumor effect.

Example 10

Preparation of Anti-PERP Human CDR-Grafted Antibody (1) Design of Amino Acid Sequence of VH and VL of Anti-PERP Human CDR-Grafted Antibody Firstly, an amino acid sequence of VH of human CDR-grafted antibody to PERP (hereinafter referred to as "anti-PERP CDR-grafted antibody") was designed as follows.

An amino acid sequence of FR of VH of human antibody for grafting an amino acid sequence of CDRs of VH of anti-PERP mouse antibody KM3411 identified in (1)-3 of Example 7 was selected, Kabat, et al., classified various known VH of human antibody into 3 kinds of subgroups (HSG I to III) in view of homology of amino acid sequences thereof and reported the common sequence for each group [*Sequences of Protein of Immunological Interested*, U.S. Dept. Health and Human Services (1991)]. Since there is a possibility that immunogenicity of the common sequence is further decreased in human, it was decided to design the amino acid sequence of VH of anti-PERP CDR-grafted antibody based on such a common sequence. In order to prepare an anti-PERP CDR-grafted antibody having higher binding activity, an amino acid sequence of FR having the highest homology to the amino acid sequence of FR of VH of KM3411 was selected for design among amino acid sequences of FR of the common sequence of the 3 kinds of subgroups of VH of human antibody. Table 4 shows the result of homology search. As shown in Table 4, the amino acid sequence of FR of VH region of KM3411 has the highest homology to the subgroup II.

TABLE 4

| Homology between amino acid sequence of FR of common sequence of each subgroup of VH of human antibody and amino acid sequence of FR of VH of KM3411 |||
| --- | --- | --- |
| HSG I | HSG II | HSG III |
| 54.0% | 74.7% | 60.9% |

From the above result, amino acid sequences of CDRs of VH of the anti-PERP mouse antibody KM3411 were grafted to appropriate positions in the amino acid sequence of FR of the common sequence of subgroup II of VH of human antibody. Although Ile at position 47, Ile at position 86, Gln at position 100, Glu at position 107 and Thr at position 111 in the amino acid sequence of VH of KM3411 represented by SEQ ID NO:12 were not the amino acid residues having the highest frequency in usage in the corresponding site of the amino acid sequence of the human antibody FR described in Kabat, et al., they were amino acids which were used in rather high frequency and, therefore, the amino acid residue found in the above amino acid sequence of KM3411 were used. Thus, the amino acid sequence HV0 of VH of anti-PERP CDR-grafted antibody represented by SEQ ID NO:25 was designed.

Then, an amino acid sequence of VL of the anti-PERP CDR-grafted antibody was designed as follows.

An amino acid of FR of VL of human antibody for grafting amino acid sequences of CDRs of VL of the anti-PERP mouse antibody KM3411 identified in (1)-3 of Example 7 was selected. Kabat, et al. classified VL of various known human antibodies into 4 kinds of subgroups (HSG I to IV) in view of homology of amino acid sequences thereof and further reported the common sequence for each subgroup [*Sequences of Protein of Immunological Interested*, U.S. Dept. Health and Human Services (1991)]. Accordingly, in the same manner as in the case of VH, an amino acid sequence of FR having the highest homology to the amino acid sequence of FR of VL of KM3411 was selected from the amino acid sequences of FR of the common sequence of the 4 kinds of subgroups of VL of human antibody. Table 5 shows the result of the homology search. As shown in Table 5, the amino acid sequence of FR of VL of KM3411 showed the highest homology to the subgroup I.

TABLE 5

| Homology between amino acid sequence of FR of common sequence of each subgroup of VL of human antibody and amino acid sequence of FR of VL of KM3411 ||||
| --- | --- | --- | --- |
| HSG I | HSG II | HSG III | HSG IV |
| 67.5% | 62.5% | 66.2% | 65.0% |

From the above result, amino acid sequences of CDRs of VL of the anti-PERP mouse antibody KM3411 were grafted to appropriate positions in the amino acid sequence of FR of the common sequence of subgroup I of VL of human antibody, and the amino acid sequence LV0 of VL of the anti-PERP CDR-grafted antibody described in SEQ ID NO:26 was designed.

The amino acid sequence HV0 of VH of the anti-PERP CDR-grafted antibody designed hereinabove and the amino acid sequence LV0 of VL thereof are sequences in which only amino acid sequences of CDRs of the anti-PERP mouse antibody KM3411 are grafted to the amino acid sequence of FR of the selected human antibody but, in general, in the preparation of human CDR-grafted antibody, there are many cases where the binding activity is lowered by merely grafting the amino acid sequences of CDRs of a mouse antibody to FR of a human antibody. In order to avoid the lowering of the binding activity, it has been carried out that, in the amino acid residues of FR being different between a human antibody and a mouse antibody, an amino acid residue which is believed to affect the binding activity is modified together with grafting amino acid sequences of CDRs. Accordingly, in the present Example, amino acid residues of FR which are believed to affect the binding activity were also modified as follows.

Firstly, a three-dimensional structure of an antibody V region (HV0 LV0) comprising the amino acid sequence HV0 of VL of the anti-PERP CDR-grafted antibody designed above and the amino acid sequence LV0 of VL thereof was constructed by computer modeling. The preparation of the ordinate of three-dimensional structure was carried out according to the manufacture's instructions attached thereto by using the software AbM (manufactured by Oxford Molecular). The display of the three dimensional structure was carried out according to the manufacture's instructions attached thereto by using the software Pro-Explore (manufactured by Oxford Molecular) or Viewer Lite (manufactured by Accelrys). A computer model of three dimensional structure of V region of the anti-PERP mouse monoclonal antibody KM3411 was also constructed in similar manner. Furthermore, similarly, a three dimensional structure model comprising an amino acid sequence where, in amino acid sequences of FR of VH and VL of HV0 LV0, the amino acid residue being different from the anti-PERP mouse antibody KM3411 is successively modified to the amino acid residue found in the corresponding position of the anti-PERP mouse antibody KM3411 was constructed, and then the three dimensional structures of V region of anti-PERP mouse antibody KM3411, HV0 LV0 and the modified antibody were compared.

As a result, as the amino acid residues which are believed to change the three dimensional structure of the antigen binding site and to affect the binding activity of the antibody in the amino acid residues of FR of HV0 LV0, Gly at position 27, Ser at position 30, Pro at position 41, Lys at position 44, Gly at position 45, Val at position 72 and Ala at position 97 were selected in HV0, and Gln at position 3, Thr at position 5, Tyr at position 35, Ala at position 42, Leu at position 46, Phe at position 70 and Leu at position 77 were selected in LV0. Among those amino acid residues selected, at least one amino acid sequence was modified to an amino acid residue existing in the same site of the mouse antibody KM3411 and VH and VL of human CDR-grafted antibody having various modifications were designed.

(2) Construction of cDNA Encoding VH of the Anti-PERP Human CDR-Grafted Antibody cDNA encoding the amino acid sequence HV0 of VH of the anti-PERP human CDR-grafted antibody designed in the Example (1) was constructed using PCR as follows.

Firstly, the designed amino acid sequence was ligated with a secretory signal sequence of H chain of the anti-PERP mouse antibody KM3411 represented by positions 1 to 18 of SEQ ID NO:12 to give a complete antibody amino acid sequence. Then, the amino acid sequence was converted to genetic codons. When plural genetic codons were present in one amino acid residue, the corresponding codon was decided by taking the frequency in usage found in the nucleotide sequence of a gene encoding an antibody [*Sequences of Proteins of Immunological Interest*, U.S. Dept. Health and Human Services (1991)] into consideration. The decided genetic codons were ligated to design a nucleotide sequence of cDNA encoding the amino acid sequence of the complete antibody V region and binding nucleotide sequences of primers for amplification in PCR (including a restriction enzyme recognizing sequence for cloning to vector for humanized antibody expression) were further added to 5'-terminal and 3'-terminal. The designed nucleotide sequence was divided into 6 nucleotide sequences each comprising about 100 bases from the 5'-terminal side (in the adjacent nucleotide sequences, overlap sequences of about 20 bases were to be formed at terminals thereof) and synthetic oligonucleotides were synthesized by arranging them in the order of a sense chain and an antisense chain.

Each oligonucleotide was added to 50 μL of the reaction solution to give a final concentration of 0.1 μmol/L, and PCR was carried out using 0.5 μmol/L of M13 primer RV (manufactured by Takara Shuzo), 0.5 μmol/L of M13 primer M4 (manufactured by Takara Shuzo) and 1 unit of KOD polymerase (manufactured by Toyobo) according to the manufacturers instructions attached to the KOD polymerase. The reaction was carried out according to the conditions described in the manufacture's instructions (30 cycles, one cycle consisting of reaction at 94° C. for 30 seconds, reaction at 50° C. for 30 seconds and reaction at 74° C. for 60 seconds). The reaction solution was precipitated with ethanol, dissolved in sterile water, subjected to appropriate restriction enzyme treatment and ligated with a plasmid pBluescript II SK(−) (manufactured by Stratagene). *Escherichia coli* DH5α was transformed using the thus obtained recombinant plasmid DNA solution, a plasmid DNA was prepared from the cell line of the transformant and the nucleotide sequence was analyzed using Big Dye Terminator Cycle Sequencing FS Ready Reaction Kit (manufactured by Applied Biosystems) to give a plasmid having the desired nucleotide sequence.

Then, the amino acid residue of FR designed in (1) of the Example was modified either by such a manner that a synthetic oligonucleotide having modification was prepared and then the above-described PCR was carried out or by such a manner that the above-prepared plasmid DNA containing cDNA encoding HV0 prepared above is used as a template and PCR was carried out using synthetic DNA having modification as a primer to isolate the amplified fragment. For the genetic codons of the amino acid residues after modification, the modification was carried out to give genetic codons found in the anti-PERP mouse antibody KM3411.

(3) Construction of cDNA Encoding VL of the Anti-PERP Human CDR-Grafted Antibody cDNA encoding the amino acid sequence LV0 of VL of the anti-PERP human CDR-grafted antibody designed in (1) of the Example was constructed using PCR as follows.

Firstly, the designed amino acid sequence was ligated with a secretory signal sequence of L chain of the anti-PERP mouse antibody KM3411 represented by positions 1 to 22 in the amino acid sequence represented by SEQ ID NO:14 to give a complete antibody amino acid sequence. Then, the amino acid sequence was converted to genetic codons. When plural genetic codons were present in one amino acid residue, the corresponding codon was decided by taking the frequency in usage found in the nucleotide sequence of a gene encoding an antibody [*Sequences of Proteins of Immunological Interest*, U.S. Dept. Health and Human Services (1991)] into consideration. The decided genetic codons were ligated to design a nucleotide sequence of cDNA encoding the amino acid sequence of the complete antibody V region and, further, binding nucleotide sequences of primers for amplification in PCR (including a restriction enzyme recognizing sequence for cloning to vector for humanized antibody expression) were added to 5'-terminal and 3'-terminal. The designed nucleotide sequence was divided into 6 nucleotide sequences each comprising about 100 bases from the 5'-terminal side (in the adjacent nucleotide sequences, overlap sequences of about 20 bases were to be formed at terminals thereof) and, by arranging them in the order of an sense chain and an antisense chain, synthetic oligonucleotides were synthesized.

Each oligonucleotide was added to 50 μL of the reaction solution to give a final concentration of 0.1 μmol/L and PCR was carried out using 0.5 μmol/L of M13 primer RV (manufactured by Takara Shuzo), 0.5 μmol/L of M13 primer M4 (manufactured by Takara Shuzo) and 1 unit of KOD polymerase (manufactured by Toyobo) according to the manufacture's instructions attached to the KOD polymerase by the same manner as in the above (3). The reaction solution was precipitated with ethanol, dissolved in sterile water, subjected to appropriate restriction enzyme treatment and ligated with a plasmid pBluescript II SK(−) (manufactured by Stratagene). *Escherichia coli* DH5α was transformed using the thus obtained recombinant plasmid DNA solution, a plasmid DNA was prepared from the cell line of the transformant and the nucleotide sequence was analyzed using Big Dye Terminator Cycle Sequencing FS Ready Reaction Kit (manufactured by Applied Biosystems) to give a plasmid having the desired nucleotide sequence.

Then, the amino acid residue of FR designed in the Example (1) was modified either by such a manner that a synthetic oligonucleotide having modification was prepared and then the above-described PCR was carried out or by such a manner that the above-prepared plasmid DNA containing cDNA encoding LV0 prepared above was used as a template and PCR was carried out using a synthetic DNA having modification as a primer to isolate the amplified fragment. The genetic codons of the amino acid residues after modification were altered to give genetic codons found in the anti-PERP mouse antibody KM3411.

(4) Construction of Expression Vector for Anti-PERP Human CDR-Grafted Antibody cDNA encoding HV0 and LV0 each prepared in (2) and (3) of this Example or cDNA encoding a modified product thereof was inserted into an appropriate position of vector for humanized antibody expression, pKANTEX93, described in WO97/10354 to construct a vector for expression of various kinds of anti-PERP human CDR-grafted antibodies.

(5) Stable Expression Using Animal Cells of the Anti-PERP Human CDR-Grafted Antibody and Obtaining Purified Antibody Stable expression using animal cells of the anti-PERP human CDR-grafted antibody and purification of antibody from the culture supernatant were carried out by a method similar to that described in 7(2)-2 and (3) of Example 7.

INDUSTRIAL APPLICABILITY

The present invention provides an antibody which specifically recognizes three-dimensional structure of an extracellular region of a polypeptide encoded by PERP gene and binds to the extracellular region or the antibody fragment thereof. The antibody or the antibody fragment can be used in a method for immunologically detecting a polypeptide encoded by the PERP gene and an agent for the detection, a method for immunological detection or immunoassay of a cell expressing the polypeptide and an agent for the detection or determination, and an agent for diagnosing or treating a disease related to a polypeptide encoded by the PERP gene.

Free Text of Sequence Listings
SEQ ID NO:3-Description of artificial sequence: Synthetic DNA
SEQ ID NO:4-Description of artificial sequence: Synthetic DNA
SEQ ID NO:5-Description of artificial sequence: Synthetic DNA
SEQ ID NO:6-Description of artificial sequence: Synthetic DNA
SEQ ID NO:7-Description of artificial sequence: Synthetic DNA
SEQ ID NO:8-Description of artificial sequence: Synthetic DNA
SEQ ID NO: 9-Description of artificial sequence: Synthetic DNA
SEQ ID NO: 10-Description of artificial sequence: Synthetic DNA
SEQ ID NO:21-Description of artificial sequence: Synthetic DNA
SEQ ID NO:22-Description of artificial sequence: Synthetic DNA
SEQ ID NO:23-Description of artificial sequence: Synthetic DNA
SEQ ID NO:24-Description of artificial sequence: Synthetic DNA
SEQ ID NO:25-Description of artificial sequence: Synthetic peptide
SEQ ID NO:26-Description of artificial sequence: Synthetic peptide

The invention claimed is:

1. An isolated antibody, or antigen-binding fragment thereof, wherein said antibody or antigen-binding fragment thereof specifically binds a three-dimensional structure of an extracellular region of a polypeptide encoded by the PERP gene, and wherein said antibody or antigen-binding fragment thereof specifically binds to an epitope bound by a monoclonal antibody produced by hybridoma KM3411 (FERM BP-8643).

2. The antibody or antigen-binding fragment thereof according to claim 1, wherein the extracellular region is represented by residues 35 to 75 and residues 130 to 154 of SEQ ID NO: 2.

3. The antibody or antigen-binding fragment thereof according to claim 1, wherein the antibody or antigen-binding fragment is monoclonal.

4. The antibody or antigen-binding fragment thereof according to claim 3, wherein said antibody or antigen-binding fragment thereof is a monoclonal antibody produced by hybridoma KM3411 (FERM BP-8643).

5. A hybridoma which produces the monoclonal antibody of claim 3.

6. The hybridoma according to claim 5, wherein said hybridoma is hybridoma KM3411 (FERM BP-8643).

7. The antibody or antigen-binding fragment thereof according to claim 3, wherein said antibody or antigen-binding fragment thereof is a recombinant antibody.

8. The antibody or antigen-binding fragment thereof according to claim 7, wherein said antibody or antigen-binding fragment thereof is a humanized antibody or a human antibody.

9. The antibody or antigen-binding fragment thereof according to claim 8, wherein said humanized antibody is a human chimeric antibody or human complimentarity determining region (CDR)-grafted antibody, or an antigen-binding fragment thereof.

10. The human chimeric antibody or antigen-binding fragment thereof according to claim 9, wherein said human chimeric antibody or antigen-binding fragment thereof comprises a heavy chain (H chain) variable region (V region) and a light chain (L chain) V region of a non-human antibody.

11. The human chimeric antibody or antigen-binding fragment thereof according to claim 10, wherein said human chimeric antibody or antigen-binding fragment thereof further comprises an H chain constant region (C region) and an L chain C region of a human antibody.

12. The human chimeric antibody or antigen-binding fragment thereof according to claim 10, wherein the VH of the antibody comprises the amino acid sequence of residues 19 to 130 of SEQ ID NO: 12.

13. The human chimeric antibody or antigen-binding fragment thereof according to claim 10, wherein the VL of the antibody comprises the amino acid sequence of residues 23 to 128 of SEQ ID NO: 14.

14. The human chimeric antibody or antigen-binding fragment thereof according to claim 10, wherein the VH of the antibody comprises the amino acid sequence of residues 19 to 130 of SEQ ID NO: 12, and the VL of the antibody comprises the amino acid sequence of residues 23 to 128 of SEQ ID NO: 14.

15. The human CDR-grafted antibody or antigen-binding fragment thereof according to claim 9, wherein the framework regions of the VH and VL are from a human antibody.

16. The human CDR-grafted antibody or antigen-binding fragment thereof according to claim 15, wherein said human CDR-grafted antibody or antigen-binding fragment thereof further comprises an H chain C region and an L chain C region of a human antibody.

17. The human CDR-grafted antibody or antigen-binding fragment thereof according to claim 15, wherein CDR1, CDR2 and CDR3 of VH of the antibody or antigen-binding fragment thereof comprise the amino acid sequences of SEQ ID NOs: 15, 16 and 17, respectively, and CDR1, CDR2 and CDR3 of VL of the antibody comprise the amino acid sequences of SEQ ID NOs: 18, 19 and 20, respectively.

18. The human CDR-grafted antibody or antigen-binding fragment thereof according to claim 15, wherein VH of the antibody comprises the amino acid sequence of SEQ ID NO:25, or the amino acid sequence of SEQ ID NO:25 in which at least one amino acid is substituted, wherein the substituted amino acid is selected from the group consisting of Gly at position 27, Ser at position 30, Pro at position 41, Lys at position 44, Gly at position 45, Val at position 72 and Ala at position 97.

19. The human CDR-grafted antibody or antigen-binding fragment thereof according to claim 15, wherein VL of the antibody comprises the amino acid sequence of SEQ ID NO:26 or the amino acid sequence of SEQ ID NO: 26 in which at least one amino acid is substituted, wherein the substituted amino acid is selected from the group consisting of Gln at position 3, Thr at position 5, Tyr at position 35, Ala at position 42, Leu at position 46, Phe at position 70 and Leu at position 77.

20. The human CDR-grafted antibody or antigen-binding fragment thereof according to claim 15,
wherein VH of the antibody comprises the amino acid sequence of SEQ ID NO: 25 or the amino acid sequence of SEQ ID NO: 25 in which at least one amino acid is substituted, wherein the substituted amino acid is selected from the group consisting of Gly at position 27, Ser at position 30, Pro at position 41, Lys at position 44, Gly at position 45, Val at position 72 and Ala at position 97, and wherein VL of the antibody comprises the amino acid sequence of SEQ ID NO: 26, or the amino acid sequence of SEQ ID NO: 26 in which at least one amino acid is substituted, wherein the substituted amino acid is selected from the group consisting of Gln at position 3, Thr at position 5, Tyr at position 35, Ala at position 42, Leu at position 46, Phe at position 70 and Leu at position 77.

21. The antibody fragment according to claim 1, wherein the antibody fragment is an antibody fragment selected from the group consisting of Fab, Fab', F(ab')$_2$, a single chain antibody (scFv), a dimerized V region (diabody), a disulfide stabilized V region (dsFv) and a peptide comprising CDR.

22. An agent for detecting or assaying human PERP protein, wherein said agent comprises the antibody or antigen-binding fragment thereof of claim 1.

23. An agent for diagnosing a disease related to human PERP protein, wherein said agent comprises the antibody or antigen-binding fragment thereof of claim 1.

24. The diagnostic agent according to claim 23, wherein the disease is cancer.

25. A therapeutic agent for treating a disease related to human PERP protein, wherein said agent comprises the antibody or antigen-binding fragment thereof of claim 1 as an active ingredient.

26. The therapeutic agent according to claim 25, wherein the disease is cancer.

27. A process for producing the antibody or the antibody fragment described in any one of claims 1-4, 7-14, 15, 16 and 17-21, which comprises culturing the hybridoma described in claim 6 or 7 in a medium to form and accumulate the antibody or the antibody fragment according to any one of claims 1-7, 14-15, 15, 16 and 17-21 in the culture, and recovering the antibody or the antibody fragment from the culture.

28. A method for immunological detection or immunoassay of a polypeptide encoded by the PERP gene, which comprises using the antibody or the antibody fragment described in any one of claims 1-4, 7-14, 15, 16 and 17-21.

29. The method according to claim 28, wherein the method for immunological detection or immunoassay is an immunoprecipitation method.

30. A method for immunological detection or immunoassay of a cell expressing a polypeptide encoded by the PERP gene, which comprises using the antibody or the antibody fragment described in any one of claims 1-4, 7-14, 15, 16 and 17-21.

31. The method according to claim 30, wherein the method for immunological detection or immunoassay method is a fluorescent cell staining method.

32. A method for diagnosing a PERP expressing cancer related to a polypeptide encoded by the PERP gene, which comprises detecting or determining a cell expressing a polypeptide encoded by the PERP gene using the antibody or the antibody fragment described in any one of claims 1-4, 7-14, 15, 16 and 17-21.

33. A method for diagnosing a PERP expressing cancer related to a polypeptide encoded by the PERP gene, which comprises detecting or assaying a polypeptide encoded by the PERP gene using the antibody or the antibody fragment according to any one of claims 1-4, 7-14, 15, 16 and 17-21.

* * * * *

SEQUENCE LISTING

```
<160> NUMBER OF SEQ ID NOS: 26

<210> SEQ ID NO 1
<211> LENGTH: 1941
<212> TYPE: DNA
<213> ORGANISM: Homo sapiens

<400> SEQUENCE: 1
gcttttgtgg cggcgcccgc gctcgcaggc cactctctgc tgtcgcccgt cccgcgcgct      60
cctccgaccc gctccgctcc gctccgctcg gcccgcgcc gcccgtcaac atgatccgct     120
gcggcctggc ctgcgagcgc tgccgctgga tcctgccccct gctcctactc agcgccatcg    180
```

```
ccttcgacat catcgcgctg gccggccgcg gctggttgca gtctagcgac cacggccaga    240
cgtcctcgct gtggtggaaa tgctcccaag agggcggcgg cagcgggtcc tacgaggagg    300
gctgtcagag cctcatggag tacgcgtggg gtagagcagc ggctgccatg ctcttctgtg    360
gcttcatcat cctggtgatc tgtttcatcc tctccttctt cgccctctgt ggaccccaga    420
tgcttgtctt cctgagagtg attggaggtc tccttgcctt ggctgctgtg ttccagatca    480
tctccctggt aatttacccc gtgaagtaca cccagacctt cacccttcat gccaaccctg    540
ctgtcactta catctataac tgggcctacg gctttgggtg ggcagccacg attatcctga    600
ttggctgtgc cttcttcttc tgctgcctcc ccaactacga agatgacctt ctgggcaatg    660
ccaagcccag gtacttctac acatctgcct aacttgggaa tgaatgtggg agaaaatcgc    720
tgctgctgag atggactcca gaagaagaaa ctgtttctcc aggcgacttt gaacccattt    780
tttggcagtg ttcatattat taaactagtc aaaaatgcta aaataatttg ggagaaaata    840
tttttttaagt agtgttatag tttcatgttt atctttatt atgttttgtg aagttgtgtc    900
ttttcactaa ttacctatac tatgccaata tttcctatct atccataaca tttatactac    960
atttgtaaga gaatatgcac gtgaaactta acactttata aggtaaaaat gaggtttcca   1020
agatttaata atctgatcaa gttcttgtta tttccaaata gaatggactc ggtctgttaa   1080
gggctaagga gaagaggaag ataaggttaa aagttgttaa tgaccaaaca ttctaaaaga   1140
aatgcaaaaa aaaagtttat tttcaagcct tcgaactatt taaggaaagc aaaatcattt   1200
cctaaatgca tatcatttgt gagaatttct cattaatatc ctgaatcatt cattttagct   1260
aaggcttcat gttgactcga tatgtcatct aggaaagtac tatttcatgg tccaaacctg   1320
ttgccatagt tggtaaggct ttcctttaag tgtgaaatat ttagatgaaa ttttctcttt   1380
taaagttctt tatagggtta gggtgtggga aaatgctata ttaataaatc tgtagtgttt   1440
tgtgtttata tgttcagaac cagagtagac tggattgaaa gatggactgg gtctaattta   1500
tcatgactga tagatctgtt aagttgtgta gtaaagcatt aggagggtca ttcttgtcac   1560
aaaagtgcca ctaaaacagc ctcaggagaa taaatgactt gcttttctaa atctcaggtt   1620
tatctgggct ctatcatata gacaggcttc tgatagtttg caactgtaag cagaaaccta   1680
catatagtta aaatcctggt ctttcttggt aaacagattt taaatgtctg atataaaaca   1740
tgccacagga gaattcgggg atttgagttt ctctgaatag catatatatg atgcatcgga   1800
taggtcatta tgattttta ccatttcgac ttacataatg aaaaccaatt cattttaaat   1860
atcagattat tattttgtaa gttgtggaaa aagctaattg tagttttcat tatgaagttt   1920
tcccaataaa ccaggtattc t                                             1941

<210> SEQ ID NO 2
<211> LENGTH: 193
<212> TYPE: PRT
<213> ORGANISM: Homo sapiens

<400> SEQUENCE: 2

Met Ile Arg Cys Gly Leu Ala Cys Glu Arg Cys Arg Trp Ile Leu Pro
1               5                   10                  15

Leu Leu Leu Leu Ser Ala Ile Ala Phe Asp Ile Ile Ala Leu Ala Gly
            20                  25                  30

Arg Gly Trp Leu Gln Ser Ser Asp His Gly Gln Thr Ser Ser Leu Trp
        35                  40                  45

Trp Lys Cys Ser Gln Glu Gly Gly Gly Ser Gly Ser Tyr Glu Glu Gly
    50                  55                  60
```

```
Cys Gln Ser Leu Met Glu Tyr Ala Trp Gly Arg Ala Ala Ala Met
 65                  70                  75                  80

Leu Phe Cys Gly Phe Ile Ile Leu Val Ile Cys Phe Ile Leu Ser Phe
                 85                  90                  95

Phe Ala Leu Cys Gly Pro Gln Met Leu Val Phe Leu Arg Val Ile Gly
            100                 105                 110

Gly Leu Leu Ala Leu Ala Ala Val Phe Gln Ile Ile Ser Leu Val Ile
            115                 120                 125

Tyr Pro Val Lys Tyr Thr Gln Thr Phe Thr Leu His Ala Asn Pro Ala
130                 135                 140

Val Thr Tyr Ile Tyr Asn Trp Ala Tyr Gly Phe Gly Trp Ala Ala Thr
145                 150                 155                 160

Ile Ile Leu Ile Gly Cys Ala Phe Phe Phe Cys Cys Leu Leu Asn Tyr
                165                 170                 175

Glu Asp Asp Leu Leu Gly Asn Ala Lys Pro Arg Tyr Phe Tyr Thr Ser
            180                 185                 190

Ala

<210> SEQ ID NO 3
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 3
tgtcagagcc tcatggagta cgc                                           23

<210> SEQ ID NO 4
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 4
tggagtccat ctcagcagca gc                                            22

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 5
ccatcgcctt cgacatcatc gc                                            22

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 6
tgcccaccca aagccgtagg                                               20

<210> SEQ ID NO 7
<211> LENGTH: 33
<212> TYPE: DNA
<213> ORGANISM: Artificial Sequence
<220> FEATURE:
```

<223> OTHER INFORMATION: Synthetic oligonucleotide primer

<400> SEQUENCE: 7
ccggaattcg ccaccatgat ccgctgcggc ctg        33

<210> SEQ ID NO 8
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 8
cccaagcttg ggcagatgtg tagaagta        28

<210> SEQ ID NO 9
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 9
ccagggtcac catggagtta gtttgggcag        30

<210> SEQ ID NO 10
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 10
gaagcacacg actgaggcac ctccagatgt        30

<210> SEQ ID NO 11
<211> LENGTH: 390
<212> TYPE: DNA
<213> ORGANISM: Mus musculus
<220> FEATURE:
<221> NAME/KEY: CDS
<222> LOCATION: (1)..(390)

<400> SEQUENCE: 11

```
atg aga gtg ctg att ctt ttg tgg ctg ttc aca gcc ttt cct ggt atc       48
Met Arg Val Leu Ile Leu Leu Trp Leu Phe Thr Ala Phe Pro Gly Ile
 1               5                  10                  15 ctg tct gat gtg cag ctt cag gag tcg gga cct ggc ctg gtg aaa cct       96
Leu Ser Asp Val Gln Leu Gln Glu Ser Gly Pro Gly Leu Val Lys Pro
             20                  25                  30 tct cag tct ctg tcc ctc acc tgc act gtc act ggc ttc tca atc acc      144
Ser Gln Ser Leu Ser Leu Thr Cys Thr Val Thr Gly Phe Ser Ile Thr
         35                  40                  45 act gaa tat gcc tgg aac tgg atc cgg cag ttt cca gga aac aga ctg      192
Thr Glu Tyr Ala Trp Asn Trp Ile Arg Gln Phe Pro Gly Asn Arg Leu
     50                  55                  60 gag tgg atg ggc tat ata ggc tac act ggt aga act aac tac agc cca      240
Glu Trp Met Gly Tyr Ile Gly Tyr Thr Gly Arg Thr Asn Tyr Ser Pro
 65                  70                  75                  80 tct ctc aaa agt cga atc tct atc act cga gac act tcc aag aac cag      288
Ser Leu Lys Ser Arg Ile Ser Ile Thr Arg Asp Thr Ser Lys Asn Gln
                 85                  90                  95 ttc ttc ctg cag ttg aat tct gtg act act gag gac aca gcc aca tat      336
Phe Phe Leu Gln Leu Asn Ser Val Thr Thr Glu Asp Thr Ala Thr Tyr
            100                 105                 110
```

```
tac tgt aca agg atg gac tac tgg ggt caa gga acc tca gtc acc gtc      384
Tyr Cys Thr Arg Met Asp Tyr Trp Gly Gln Gly Thr Ser Val Thr Val
        115                 120                 125 tcc tca                                                              390
Ser Ser
    130

<210> SEQ ID NO 12
<211> LENGTH: 130
<212> TYPE: PRT
<213> ORGANISM: Mus musculus

<400> SEQUENCE: 12

Met Arg Val Leu Ile Leu Leu Trp Leu Phe Thr Ala Phe Pro Gly Ile
 1               5                  10                  15

Leu Ser Asp Val Gln Leu Gln Glu Ser Gly Pro Gly Leu Val Lys Pro
                20                  25                  30

Ser Gln Ser Leu Ser Leu Thr Cys Thr Val Thr Gly Phe Ser Ile Thr
            35                  40                  45

Thr Glu Tyr Ala Trp Asn Trp Ile Arg Gln Phe Pro Gly Asn Arg Leu
    50                  55                  60

Glu Trp Met Gly Tyr Ile Gly Tyr Thr Gly Arg Thr Asn Tyr Ser Pro
 65                 70                  75                  80

Ser Leu Lys Ser Arg Ile Ser Ile Thr Arg Asp Thr Ser Lys Asn Gln
                85                  90                  95

Phe Phe Leu Gln Leu Asn Ser Val Thr Thr Glu Asp Thr Ala Thr Tyr
            100                 105                 110

Tyr Cys Thr Arg Met Asp Tyr Trp Gly Gln Gly Thr Ser Val Thr Val
        115                 120                 125

Ser Ser
130

<210> SEQ ID NO 13
<211> LENGTH: 384
<212> TYPE: DNA
<213> ORGANISM: Mus musculus
<220> FEATURE:
<221> NAME/KEY: CDS
<222> LOCATION: (1)..(384)

<400> SEQUENCE: 13 atg cat ttt caa gtg cag att ttc agc ttc ctg cta atc agt gcc tca       48
Met His Phe Gln Val Gln Ile Phe Ser Phe Leu Leu Ile Ser Ala Ser
 1               5                  10                  15 gtc ata atg tcc aga gga caa att gtt ctc ata cag tct cca gta atc       96
Val Ile Met Ser Arg Gly Gln Ile Val Leu Ile Gln Ser Pro Val Ile
                20                  25                  30 atg tct gca tct cca ggg gag aag gtc act ata acc tgc agt gcc agt      144
Met Ser Ala Ser Pro Gly Glu Lys Val Thr Ile Thr Cys Ser Ala Ser
            35                  40                  45 tca agt gta agt tac atg cac tgg ttc cag cag aag cca ggc act tct      192
Ser Ser Val Ser Tyr Met His Trp Phe Gln Gln Lys Pro Gly Thr Ser
    50                  55                  60 ccc aaa ctc tgg att tat agc aca tcc aac ctg gct tct gga gtc cct      240
Pro Lys Leu Trp Ile Tyr Ser Thr Ser Asn Leu Ala Ser Gly Val Pro
 65                 70                  75                  80 gct cgc ttc agt ggc agt gga tct ggg acc tct tac tca ctc aca att      288
Ala Arg Phe Ser Gly Ser Gly Ser Gly Thr Ser Tyr Ser Leu Thr Ile
                85                  90                  95 agc cga atg gag gct gaa gat gct gcc act tat tac tgc cag caa agg      336
Ser Arg Met Glu Ala Glu Asp Ala Ala Thr Tyr Tyr Cys Gln Gln Arg
```

```
            100                 105                 110
agt tct tac cca ccc acg ttc ggt gct ggg acc aag ctg gag ctg aaa      384
Ser Ser Tyr Pro Pro Thr Phe Gly Ala Gly Thr Lys Leu Glu Leu Lys
        115                 120                 125
```

<210> SEQ ID NO 14
<211> LENGTH: 128
<212> TYPE: PRT
<213> ORGANISM: Mus musculus

<400> SEQUENCE: 14

```
Met His Phe Gln Val Gln Ile Phe Ser Phe Leu Leu Ile Ser Ala Ser
  1               5                  10                  15

Val Ile Met Ser Arg Gly Gln Ile Val Leu Ile Gln Ser Pro Val Ile
                 20                  25                  30

Met Ser Ala Ser Pro Gly Glu Lys Val Thr Ile Thr Cys Ser Ala Ser
             35                  40                  45

Ser Ser Val Ser Tyr Met His Trp Phe Gln Gln Lys Pro Gly Thr Ser
         50                  55                  60

Pro Lys Leu Trp Ile Tyr Ser Thr Ser Asn Leu Ala Ser Gly Val Pro
 65                  70                  75                  80

Ala Arg Phe Ser Gly Ser Gly Ser Gly Thr Ser Tyr Ser Leu Thr Ile
                 85                  90                  95

Ser Arg Met Glu Ala Glu Asp Ala Ala Thr Tyr Tyr Cys Gln Gln Arg
            100                 105                 110

Ser Ser Tyr Pro Pro Thr Phe Gly Ala Gly Thr Lys Leu Glu Leu Lys
        115                 120                 125
```

<210> SEQ ID NO 15
<211> LENGTH: 6
<212> TYPE: PRT
<213> ORGANISM: Mus musculus

<400> SEQUENCE: 15

```
Thr Glu Tyr Ala Trp Asn
  1               5
```

<210> SEQ ID NO 16
<211> LENGTH: 16
<212> TYPE: PRT
<213> ORGANISM: Mus musculus

<400> SEQUENCE: 16

```
Tyr Ile Gly Tyr Thr Gly Arg Thr Asn Tyr Ser Pro Ser Leu Lys Ser
  1               5                  10                  15
```

<210> SEQ ID NO 17
<211> LENGTH: 3
<212> TYPE: PRT
<213> ORGANISM: Mus musculus

<400> SEQUENCE: 17

```
Met Asp Tyr
  1
```

<210> SEQ ID NO 18
<211> LENGTH: 10
<212> TYPE: PRT
<213> ORGANISM: Mus musculus

<400> SEQUENCE: 18

```
Ser Ala Ser Ser Ser Val Ser Tyr Met His
```

```
1               5                   10
```

<210> SEQ ID NO 19
<211> LENGTH: 7
<212> TYPE: PRT
<213> ORGANISM: Mus musculus

<400> SEQUENCE: 19

Ser Thr Ser Asn Leu Ala Ser
 1               5

<210> SEQ ID NO 20
<211> LENGTH: 9
<212> TYPE: PRT
<213> ORGANISM: Mus musculus

<400> SEQUENCE: 20

Gln Gln Arg Ser Ser Tyr Pro Pro Thr
 1               5

<210> SEQ ID NO 21
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 21
aaggaaaaaa gcggccgcac atcgctctca ctggaggctg           40

<210> SEQ ID NO 22
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 22
cgatgggccc ttggtggagg ctgaggagac ggtgactgag           40

<210> SEQ ID NO 23
<211> LENGTH: 42
<212> TYPE: DNA
<213> ORGANISM: Artificial Sequence
<220> FEATURE:
<223> OTHER INFORMATION: Synthetic oligonucleotide primer

<400> SEQUENCE: 23
ccggaattca cttatgagaa tagcagtaat tagctaggga cc         42

<210> SEQ ID NO 24
<211> LENGTH: 43
<212> TYPE: DNA
<213> ORGANISM: Artificial Sequence
<220> FEATURE:
<223> OTHER INFORMATION: Synthetic oligonucleotide primer

<400> SEQUENCE: 24
agccaccgta cgtttcagct ccagcttggt cccagcaccg aac        43

<210> SEQ ID NO 25
<211> LENGTH: 112
<212> TYPE: PRT
<213> ORGANISM: Artificial Sequence
<220> FEATURE:
<223> OTHER INFORMATION: Synthetic peptide

```
<400> SEQUENCE: 25

Gln Val Gln Leu Gln Glu Ser Gly Pro Gly Leu Val Lys Pro Ser Gln
 1               5                   10                  15

Thr Leu Ser Leu Thr Cys Thr Val Ser Gly Gly Ser Ile Ser Thr Glu
             20                  25                  30

Tyr Ala Trp Asn Trp Ile Arg Gln Pro Pro Gly Lys Gly Leu Glu Trp
         35                  40                  45

Ile Gly Tyr Ile Gly Tyr Thr Gly Arg Thr Asn Tyr Ser Pro Ser Leu
     50                  55                  60

Lys Ser Arg Ile Thr Ile Ser Val Asp Thr Ser Lys Asn Gln Phe Ser
 65                  70                  75                  80

Leu Gln Leu Ser Ser Val Thr Ala Glu Asp Thr Ala Thr Tyr Tyr Cys
                 85                  90                  95

Ala Arg Met Asp Tyr Trp Gly Gln Gly Thr Leu Val Thr Val Ser Ser
            100                 105                 110

<210> SEQ ID NO 26
<211> LENGTH: 106
<212> TYPE: PRT
<213> ORGANISM: Artificial Sequence
<220> FEATURE:
<223> OTHER INFORMATION: Synthetic peptide

<400> SEQUENCE: 26

Asp Ile Gln Met Thr Gln Ser Pro Ser Ser Leu Ser Ala Ser Val Gly
 1               5                  10                  15

Asp Arg Val Thr Ile Thr Cys Ser Ala Ser Ser Ser Val Ser Tyr Met
             20                  25                  30

His Trp Tyr Gln Gln Lys Pro Gly Lys Ala Pro Lys Leu Leu Ile Tyr
         35                  40                  45

Ser Thr Ser Asn Leu Ala Ser Gly Val Pro Ser Arg Phe Ser Gly Ser
     50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Arg Ser Ser Tyr Pro Pro Thr
                 85                  90                  95

Phe Gly Gln Gly Thr Lys Val Glu Ile Lys
            100                 105
```